United States Patent
Weiler et al.

(10) Patent No.: US 11,527,320 B2
(45) Date of Patent: Dec. 13, 2022

(54) METHODS AND SYSTEMS FOR GENERATING ACCURATELY FITTING COMPRESSION GARMENTS HAVING GLOVE OR GLOVE-LIKE FEATURES FOR A PERSON IN NEED THEREOF

(71) Applicants: Michael J. Weiler, Atlanta, GA (US); Nathan Daniel Frank, Atlanta, GA (US)

(72) Inventors: Michael J. Weiler, Atlanta, GA (US); Nathan Daniel Frank, Atlanta, GA (US)

(73) Assignee: LYMPHATECH, INC., Atlanta, GA (US)

( * ) Notice: Subject to any disclaimer, the term of this patent is extended or adjusted under 35 U.S.C. 154(b) by 0 days.

(21) Appl. No.: 17/707,350

(22) Filed: Mar. 29, 2022

(65) Prior Publication Data
US 2022/0351837 A1 Nov. 3, 2022

Related U.S. Application Data

(63) Continuation-in-part of application No. 17/532,376, filed on Nov. 22, 2021, which is a continuation of (Continued)

(51) Int. Cl.
*G16H 30/40* (2018.01)
*G16H 20/30* (2018.01)
(Continued)

(52) U.S. Cl.
CPC ............. *G16H 30/40* (2018.01); *A61F 13/08* (2013.01); *G06T 7/11* (2017.01); *G06T 17/00* (2013.01);
(Continued)

(58) Field of Classification Search
CPC ........ G16H 30/40; G16H 20/30; G16H 10/60; G06T 7/11; G06T 17/00; A61F 13/08
See application file for complete search history.

(56) References Cited

U.S. PATENT DOCUMENTS

| 6,546,309 | B1 | 4/2003 | Gazzuolo |
| 9,600,856 | B2 | 3/2017 | Bzdusek |

(Continued)

FOREIGN PATENT DOCUMENTS

| EP | 3528208 A1 | 8/2019 |
| EP | 3664030 A1 | 10/2020 |

(Continued)

OTHER PUBLICATIONS

International Search Report for EP 22170833 dated Sep. 22, 2022.

*Primary Examiner* — Mia M Thomas
(74) *Attorney, Agent, or Firm* — Thomas | Horstemeyer, LLP

(57) ABSTRACT

Various examples are provided related to identification of anthropometric information for fitting of compression garments. In one example, a method of generating compression garment fit information includes acquiring images including a selected body part or body area in need of compression therapy; processing the acquired images along with a library of compression garment fit information; generating a 3D reconstruction of the selected body part/area; deriving anthropometric information for the selected body part/area from the 3D reconstruction; providing a compression value corresponding to a prescribed or intended amount of compression therapy applied to the selected body part/area; and generating compression garment fit information for the selected body part/area. In another example, a library of compression garment fit information includes anthropometric information generated for individuals in need of compression therapy; information associated with a health con- (Continued)

dition for the individuals; and compression garment fit instructions provided by a compression garment manufacturer.

20 Claims, 28 Drawing Sheets

Related U.S. Application Data application No. 17/243,971, filed on Apr. 29, 2021, now Pat. No. 11,211,162.

(51) Int. Cl.
*G16H 10/60* (2018.01)
*G06T 17/00* (2006.01)
*G06T 7/11* (2017.01)
*A61F 13/08* (2006.01)

(52) U.S. Cl.
CPC ............ *G16H 10/60* (2018.01); *G16H 20/30* (2018.01); *G06T 2200/04* (2013.01); *G06T 2207/20101* (2013.01); *G06T 2207/30196* (2013.01)

(56) References Cited

U.S. PATENT DOCUMENTS

| | | | |
|---|---|---|---|
| 9,760,690 B1 | 9/2017 | Petkov et al. | |
| 10,008,030 B2 | 6/2018 | Chang et al. | |
| 10,045,581 B2 * | 8/2018 | Weiler | G06T 7/60 |
| 10,201,203 B2 | 2/2019 | Karavaev | |
| 10,251,438 B2 | 4/2019 | Weiler et al. | |
| 10,362,812 B2 | 7/2019 | Yue | |
| 10,489,683 B1 | 11/2019 | Koh et al. | |
| 10,679,046 B1 | 6/2020 | Black et al. | |
| 10,842,680 B1 * | 11/2020 | Weiler | A61B 5/1079 |
| 11,211,162 B1 * | 12/2021 | Weiler | G16H 30/40 |
| 2009/0047645 A1 * | 2/2009 | Dibenedetto | A61B 5/0002 434/258 |
| 2009/0048044 A1 * | 2/2009 | Oleson | A43B 5/00 473/570 |
| 2009/0048070 A1 * | 2/2009 | Vincent | G06F 1/163 482/8 |
| 2014/0022164 A1 | 1/2014 | Adhikari | |
| 2014/0195605 A1 | 7/2014 | Kallayil | |
| 2016/0088284 A1 | 3/2016 | Sareen et al. | |
| 2016/0235354 A1 | 8/2016 | Weiler et al. | |
| 2016/0314576 A1 | 10/2016 | Aliverti et al. | |
| 2018/0042322 A1 * | 2/2018 | Weiler | G06T 7/55 |
| 2018/0168261 A1 * | 6/2018 | Weiler | A61H 1/008 |
| 2020/0065960 A1 | 2/2020 | Aliverti et al. | |
| 2020/0089711 A1 | 3/2020 | Akulov | |
| 2020/0174453 A1 | 6/2020 | Bertaux Hegemann | |

FOREIGN PATENT DOCUMENTS

| | | |
|---|---|---|
| WO | WO2005106087 A1 | 11/2005 |
| WO | WO2018031703 A1 | 2/2018 |

* cited by examiner

METHODS AND SYSTEMS FOR GENERATING ACCURATELY FITTING COMPRESSION GARMENTS HAVING GLOVE OR GLOVE-LIKE FEATURES FOR A PERSON IN NEED THEREOF

CROSS-REFERENCE TO RELATED APPLICATION

This application is a continuation-in-part claiming priority to, and the benefit of, U.S. non-provisional application having Ser. No. 17/532,376, filed Nov. 22, 2021, which claims priority to, and the benefit of, U.S. non-provisional application, entitled "Methods and Systems for Identifying Body Part or Body Area Anatomical Landmarks from Digital Imagery for the Fitting of Compression Garments for a Person in Need Thereof" and having Ser. No. 17/243,971, filed Apr. 29, 2021 (issued as U.S. Pat. No. 11,211,162 on Dec. 28, 2021), all of which are hereby incorporated by reference in their entireties.

FIELD OF THE DISCLOSURE

Provided herein are systems and methods to generate fit instructions for compression garments having glove or glove-like features. The compression garment fit instructions can be derived from images acquired while the hand is on a surface. Even though a palm-facing portion of the hand is not imaged, accurate measurements of the hand can be derived. Such accuracy can be facilitated by one or more of: a collection of compression garment fit instructions provided by one or more compression garment manufacturers, information associated with prior compression garment fit events, or information associated with a health condition for the person or for one or more other persons potentially or actually in need of compression therapy. The hand measurements can be used in the fitting of prefabricated or customized compression garments having glove or glove-like features, as well in fitting other garments having such features.

BACKGROUND OF THE DISCLOSURE

"Functional garments" (or "functional clothing") are designed to fit the wearer's body so that the person can move, sit, and perform intended or desired work duties or athletic activities. Functional garments can be associated with a wearer' purpose, such as protecting the person wearing the item or imparting a medical treatment to a person in need thereof. The functionality can be imparted by way of garment design (e.g., shape, intended fit characteristics at a plurality of body part locations, fabric selection, sewing techniques, etc.). As would be appreciated, if a garment type is selected to impart an intended function to a person, that intended function may not be provided if the garment is not well-fitted to the person's body at one or more relevant locations. Thus, accurate measurements of anatomical elements of the person's body part or body area for which the subject functional garment is intended to impart the intended function will be required.

A category of functional garments comprises those that are designed to impart a therapeutic or medical benefit to a person in need thereof, of which medical compression garments are a well-known garment type that are engineered to treat edema or edema-like conditions. "Edema" is the accumulation of excess fluid in a fluid compartment. This accumulation can occur in the cells (i.e., cellular edema), in the intercellular spaces within tissue (i.e., interstitial edema), or in other spaces in the body. Edema can be caused by a variety of factors, including indications associated with osmotic pressure, such as hypotonic fluid overload, which allows the movement of water into the intracellular space, or hypoproteinemia, which decreases the concentration of plasma proteins and permits the passage of fluid out of the blood vessels into the tissue spaces. Edema may arise from a variety of illnesses and conditions, including venous valvular insufficiency, post-phlebotic syndrome, post-traumatic swelling, postoperative swelling, congestive heart failure-related swelling, hypoalbuminemia-related swelling, drug induced swelling, and lymphedema. Other factors can include poor lymphatic drainage (known as "lymphedema"), conditions associated with an increased capillary pressure (e.g., excessive retention of salt and/or water), heart failure, and conditions associated with increased capillary pressure, such as inflammation.

Referring specifically to "lymphedema" (which is a well-known and commonly occurring subset of the broader class of "edema-like conditions") at an early stage, a person will experience an increase in swelling in one or more extremities and/or in a body area. This swelling, in turn, exerts pressure on proximate cells, tissues and blood vessels. As these areas are squeezed from the increase of fluid and from the natural body response to increased inflammation (as a component of "first response" to an injury), more tissues will die, more fluids are released, and the amount of edema present in the person will increase. As edema increases, there is more potential for this "cascade effect" to continue, to result in even more damage. Such damage is often irreversible. Thus, early diagnosis and regular patient monitoring when a person is diagnosed at an early stage—or who is susceptible to the occurrence of (e.g., patients with surgery affecting lymph nodes, diabetics, etc.)—can be critical to identify swelling occurring prior to the start of the "edema cascade."

It should also be noted that lymphedema—or more broadly, edema-like conditions—have multi-dimensional health and societal effects. A woman in whom early-stage lymphedema symptoms is not accurately diagnosed is likely to experience negative health effects that greatly reduce her quality of life. A previously vibrant woman may no longer be able to work and she may no longer be able to be fully engaged with her family, community, and society at least because she may be in constant pain and her mobility will often be severely limited. Of course, the costs of treating a person with a chronic illness such as lymphedema are significant, and it often happens a patient with co-morbidities (e.g., obesity, diabetes, heart disease, etc.) can begin a steep decline in overall health condition. It is therefore important to be able to proactively identify early stage—or "subclinical"—symptoms in patients who might be susceptible to lymphedema or edema-like conditions so that they can be treated with the most effective therapeutic methods indicated for their disease-state presentation. Also, and likely not surprisingly, effective treatment of early-stage lymphedema can typically be accomplished with minimally invasive and widely accessible methods such as massage and accurately fitted compression garments having the therapeutically appropriate amount of compression incorporated therein. To ensure not only early diagnosis, but also effective monitoring and treatment of a patient in need of treatment, best clinical practices for patients potentially susceptible to lymphedema diagnosis thus require observations of the patient that are not only regular, but also dependable. A patient in need of treatment for lymphedema must be fitted with a compression garment that is engineered to address her specific body part or body area shape and size and individual lymphedema presentation, as well as being monitored regularly and consistently to ensure that her condition is well-managed and does not worsen. Or, put more succinctly: if a compression garment is not functional to impart the intended or prescribed amount of compression therapy, the patient will not obtain the necessary therapeutic response.

Today, a primary impediment to providing the necessary functionality needed to populations of people who may be in need of compression therapy is the ability to generate accurate anthropometric measurements specific for that person. As would be appreciated, a prerequisite to generating a prescribed or intended amount of compression therapy is ensuring that the garment is well-fitting on the body part or body area. "Well-fitted" means not only that the garment is sized correctly, but also that the garment includes the appropriate compression level to be applied at the right location on the person when worn. For a lower leg medical/therapeutic compression garment, this means that the compression garment is sized correctly to apply the prescribed or indicated amount of compression therapy at the person's ankle, and that it will be sized appropriately above the calf so that it will not slip or ride down. Also, the garment should not be so loose as to reduce the compressive force applied at the ankle, nor should it be so tight as to pinch or bind when worn. A well-fitted compression garment should also include fit for locations along the person's leg.

Traditionally, medical/therapeutic compression garments have been fitted in person by a trained clinician who uses a standard tape measure to generate measurements at a collection of visually identified anatomic landmarks on a person's body part or body area.

Medical/therapeutic compression garments have been fitted using this method when a person is determined to be actually or potentially symptomatic of lymphedema. The tape measurement method is low cost and widely available if there is a trained clinician accessible to a patient. This is not always the case, however. Women who have undergone cancer treatments that can give rise to lymphedema may reside in locations where there is a dearth of trained clinicians, especially in areas where health care facilities are scarce, as is often the case in the US today, as well as other countries. Moreover, while accurate detection of subclinical lymphedema associated with the fitting of medical/therapeutic compression garments requires regular assessment of the patient, a patient who is recovering from or undergoing cancer treatment (e.g., surgery, chemotherapy, or radiation) may not be able to make regular trips to a convenient location where a trained clinician is present. Even women who are located in areas where healthcare facilities are prevalent may find it difficult to obtain the regular and consistent monitoring necessary to identify lymphedema at a subclinical stage due to staffing, scheduling, and/or cost restraints.

Irrespective of the ability of a patient to obtain access to a clinician on a regular basis, the tape measurement method is often not adequate to allow early-stage lymphedema to be accurately detected and, as such, the person will not be identified as being in need of compression therapy. In application, the clinician will use her training and experience along with fit instructions provided by one or more medical/therapeutic compression garment manufacturers to identity the relevant anatomic landmarks via touching/palpation of the patient's body part or body area. Even with highly trained clinicians, there is the possibility for variability due to the human element of this measurement technique. There may also be variability in measurements between patient visits, especially when different clinicians measure the same patient.

As explained by Bragança et al. (Bragança, Sara, et al. "Current state of the art and enduring issues in anthropometric data collection." *Dyna* 83.197 (2016): 22-30) "wrongly identifying a body landmark is the main cause of observer error in the collection of anthropometric data" and that "in any anthropometry-study it is extremely important to agree on the body measurements to be recorded and the common points on the body to be identified." Bragança et al. conducted an extensive review of the anatomic landmark identification literature, including emerging methodologies using 3D imaging to generate anthropometric measurements that include landmark identification. The authors of this article reviewed a number of studies attempting to use a fully hands-free method to identify anatomic landmarks for the purpose of generating anthropometric information. It was stated in this review that "poor identification of landmark locations characteristic of 3D anthropometry has a significant effect on the derived data that I used to define participant body dimensions and to effect shape analysis." (Bragança et al. p 27). The authors further identified the landmarking process as the "most problematic" aspect of generating 3D anthropometric measurements. Although not specifically directed toward imaging for lymphedema, it is understood that this reference presents the state of the art of anatomic landmark identification techniques; no relevant updates of this article (as determined by citation analysis) have been published up to March 2021.

As demonstrated by Brangaca et al., and as confirmed by the inventors herein in extensive clinical investigations, landmark identification using current measurement methods, which include currently available 3D imaging techniques, will be greatly affected by the existence of wide variability in the nature and characteristics of patients who may present with an actual or potential diagnosis of lymphedema. In this regard, larger framed patients often show greater differences from measurement to measurement, which may be easier to identify differences between measurements taken at different times using the tape measurement method. However, lymphedema is not limited to larger framed patients; it follows that smaller framed patients who may be susceptible to lymphedema may not be adequately tracked using the tape measurement method. The tape measurement method can also require the patient to keep her arm elevated or her legs separated while standing for more time than is comfortable for a patient recovering from cancer treatment or who may have other physical impediments. Measurements made by different clinicians in different visits may also give rise to inconsistencies for an individual patient. Collectively, each of these variables associated with the tape measurement method means that there is a need for improvements in methods to detect lymphedema as well as in the fitting of compression garments engineered to treat the lymphedema, especially when the condition is in a subclinical state.

In addition to therapeutic effectiveness for the treatment of lymphedema or edema-like conditions, medical/therapeutic compression garments are an increasingly popular clothing item worn by athletes and active individuals with the goal of enhancing recovery from exercise. That is, they are "functional garments" in the context of sports. While the actual mechanism of action for compression clothing remains largely unknown today, it is generally hypothesized that when compression garments are used during recovery, muscle swelling is reduced. Improvements in the perception of recovery after exercise are seen by both men and women, who can be well-trained athletes or "weekend warriors." Generally, it seems likely that compression garments can be perceived to provide greater overall benefits following higher amounts of, or greater intensities of, exercise. Recent studies indicate that whether compression garments can provide actual therapeutic effects remains to be determined, and some of the current lack of certainty is possibly due to a dearth of reliable data on how such non-medical compression garments should be fit to an individual. Of course, if the proper fit for a sports-related compression garment is not known, the presence or absence of a therapeutic effect cannot be accurately determined, nor can the intended or prescribed function be generated.

A competitive swimming garment can be "functional" to improve a swimmer's form, such as by configuring features that can support her core to enhance firing of muscles while the swimmer is in the water. Different types of form-fitting can be incorporated in the swimming garment to provide different functionality vis a vis the muscles as, for example, set out in U.S. Pat. No. 10,548,356, the disclosure of which is incorporated herein in its entirety by this reference.

An orthopedic brace can be "functional" to apply appropriate support at a joint area for functional support of the joint. Exemplary functional features in medical appliances for the knee are illustrated in U.S. Pat. Nos. 10,285,840 and 9,220,622, the disclosures of which are incorporated herein in their entireties by this reference.

Functional garments can also be engineered to protect someone from injury or harm while undertaking an inherently dangerous activity. Examples of such garments are those worn by fire fighters, police officers, soldiers, those who work in hazardous environments (e.g., nuclear power, toxic chemicals, extreme cold or heat).

Functionality in garments is also found for aesthetic reasons in the "shapewear" realm. In order to impart the intended function for which the subject garment is worn, the garment must be properly fitted in the first order.

Specifically with reference to a hand, gloves or garments with glove-like features are increasing used for augmented reality (A/R) and virtual reality (V/R) applications. While such uses have in the past primarily been in the realm of gaming and the like, it is understood that in the future A/R and V/R will likely be associated with manufacturing, medical, educational, and business use cases. A person who is working in the "metaverse" to perform a task using their hands would need to be fitted with gloves that can accurately transfer motions to a computing device with which they are interacting. Such gloves will also need to suitably transmit haptic motions. In short, to provide an A/R or V/R experience that properly substitutes for an in-person experience, it can be expected that any gloves worn by a person in such applications will have to act as a "second skin" for the person. It follows that accurately fitted gloves are needed.

There remains a need for improvements in the generation of anthropometric measurements fitting of functional garments for a person in need thereof. The present disclosure provides this and other improvements.

SUMMARY OF THE DISCLOSURE

Aspects of the present disclosure are related to generating hand measurement information which can be used in the fitting of compression garments having glove or glove-like features. In one aspect, among others, a method of generating information for the fitting of compression garments having glove or glove-like features comprises selecting, by a user or a computer, a hand of a person in need of fitting for a compression garment configured to provide a prescribed or intended amount of compression therapy to the hand when the compression garment is worn by the person; generating, from a handheld imaging device, a plurality of images of the hand; processing, by the handheld imaging device or the computer, the acquired images to generate hand measurements associated with one or more locations relevant to the fitting of a compression garment on the hand of the person; and providing, by the imaging device or the computer, the hand measurements for use in generating compression garment fit instructions for the person. During image acquisition the hand can be positioned on a surface with a palm area facing the surface; the hand can comprise a thumb, a plurality of fingers, a hand area including the palm area that is substantially not visible, a wrist area, and a hand end or forearm area; the thumb and the plurality of fingers can be arranged in a splayed configuration; and the handheld imaging device can move freely around the hand with 6 degrees of freedom unconstrained by a mount or support. The compression garment fit instructions can be associated with selection of a prefabricated compression garment from a collection of prefabricated compression garments or fabricated of a custom compression garment.

In one or more aspects, the image processing can incorporate a priori information comprising one or more of: a collection of compression garment fit instructions provided by one or more compression garment manufacturers; information associated with prior compression garment fit events for the person or for one or more other individuals potentially or actually in need of compression therapy; or information associated with a health condition for the person or for one or more other persons potentially or actually in need of compression therapy. The information associated with prior compression garment fit events can be generated from either or both of tape measurements and imaging. At least some of the information can be validated by a human prior to use of the information in processing of the acquired images. The hand measurements can be associated with some or all of one or more fingers; the thumb; the hand area including the palm area; the wrist area; and/or the hand end or forearm area. The hand measurements can include circumferences for some or all of one or more fingers; the thumb; one or more areas on the hand area including the palm area; the wrist area; and/or the hand end or forearm area. The hand measurements include information derived from web areas located between one or more of one or more fingers; the thumb: the hand area including the palm area; the wrist area; and/or the hand end or forearm area. The hand measurements include information derived from web areas located between one or more of a pinky finger and a ring finger; the ring finger and a middle finger; the middle finger and an index finger; and the index finger and the thumb.

In various aspects, the method can comprise providing a compression garment associated with the generated compression garment fit instructions to the person; collecting information associated with the person's wearing of the provided compression garment from a first time to a second time; and/or incorporating the collected information into the library of compression garment fit information for use in generating additional compression garment fit information for the person or generating compression garment fit information for one or more other persons in need of compression therapy. The selected prefabricated compression garment or fabricated custom compression garment can be a glove; can incorporate a prescribed or indicated compression value of from 20 to 50 mm Hg: and/or can be configured to apply the prescribed or indicated compression value when the compression garment is worn by the person. The selected prefabricated compression garment or fabricated custom compression garment can be a gauntlet; can incorporate a prescribed or indicated compression value of from 20 to 50 mm Hg; and/or can be configured to apply the prescribed or indicated compression value when the compression garment is worn by the person. The selected prefabricated compression garment or fabricated custom compression garment can be an arm sleeve; can incorporate a prescribed or indicated compression value of from 20 to 50 mm Hg; and/or can be configured to apply the prescribed or indicated compression value when the compression garment is worn by the person. During image acquisition a user can be provided with information associated with a need to acquire additional images in one or more locations of the hand.

In another aspect, a method of generating information for associated with a difference in hand measurement information for a person at a first time and a second time comprises selecting, by a user or a computer, a hand of a person in need of fitting for a compression garment configured to provide a prescribed or intended amount of compression therapy to the hand when the compression garment is worn by the person; generating, by a handheld imaging device; at a first time and at a second time a plurality of images of the hand; processing, by the imaging device or the computer, the images acquired at the first time and the second time to generate first and second hand measurements, wherein each of the hand measurements are each, independently, associated with one or more locations relevant to the fitting of a compression garment on the hand; and generating, by the handheld imaging device or the computer, first and second compression garment fit instructions for the person. During each image acquisition the hand can be positioned on a surface with a palm area facing the surface; the hand can comprise a thumb, a plurality of fingers, a hand area including the palm area that is substantially not visible, a wrist; and a hand end or forearm area; the thumb and the plurality of fingers can be arranged in a splayed configuration; and/or the handheld imaging device can move freely around the hand with 6 degrees of freedom unconstrained by a mount or support. The compression garment fit instructions can be associated with selection of a first or a second prefabricated compression garment from a collection of prefabricated compression garments or fabrication of a first or a second custom compression garment.

In one or more aspects, the method can comprise comparing, by the handheld imaging device or the computer, the first and second hand measurements; and generating, by the handheld imaging device or the computer, information about a presence or absence of a change between the first and second hand measurements. The method can comprise, when there is a change between the first and second hand measurements, generating information associated with a health condition for the person. The image processing can incorporate a priori information comprising one or more of a collection of compression garment fit instructions provided by one or more compression garment manufacturers; information associated with prior compression garment fit events for the person or for one or more other individuals potentially or actually in need of compression therapy, wherein the information is generated from either or both of tape measurements and imaging and/or at least some of the information is validated by a human prior to use of the information in processing of the acquired images; and/or information associated with a health condition for the person or for one or more other persons potentially or actually in need of compression therapy.

In various aspects, each of the first and second hand measurements can be associated with some or all of one or more fingers; the thumb; the hand area including the palm area; the wrist area; and/or the hand end or forearm area. Some of the first and second hand measurements can be derived from information generated from web areas located between one or more of a pinky finger and a ring finger; the ring finger and a middle finger; the middle finger and an index finger; and/or the index finger and the thumb. The first and second hand measurements can include circumferences for some or all of one or more fingers; the thumb; one or more areas on the hand area including the palm area; the wrist area; and/or the hand end or forearm area. The selected prefabricated compression garment or fabricated custom compression garment can be configured as a glove, gauntlet, or an arm sleeve; can incorporate a prescribed or indicated compression value of from 20 to 50 mm Hg; and/or can be configured to apply the prescribed or indicated compression value when the compression garment is worn by the person. During image acquisition a user can be provided with information associated with a need to acquire additional images in one or more locations of the hand.

The identified embodiments and aspects are exemplary only and are therefore non-limiting. The details of one or more non-limiting embodiments of the disclosure are set forth in the accompanying drawings and the descriptions below. Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

DETAILED DESCRIPTION OF THE DISCLOSURE

Figure 1:
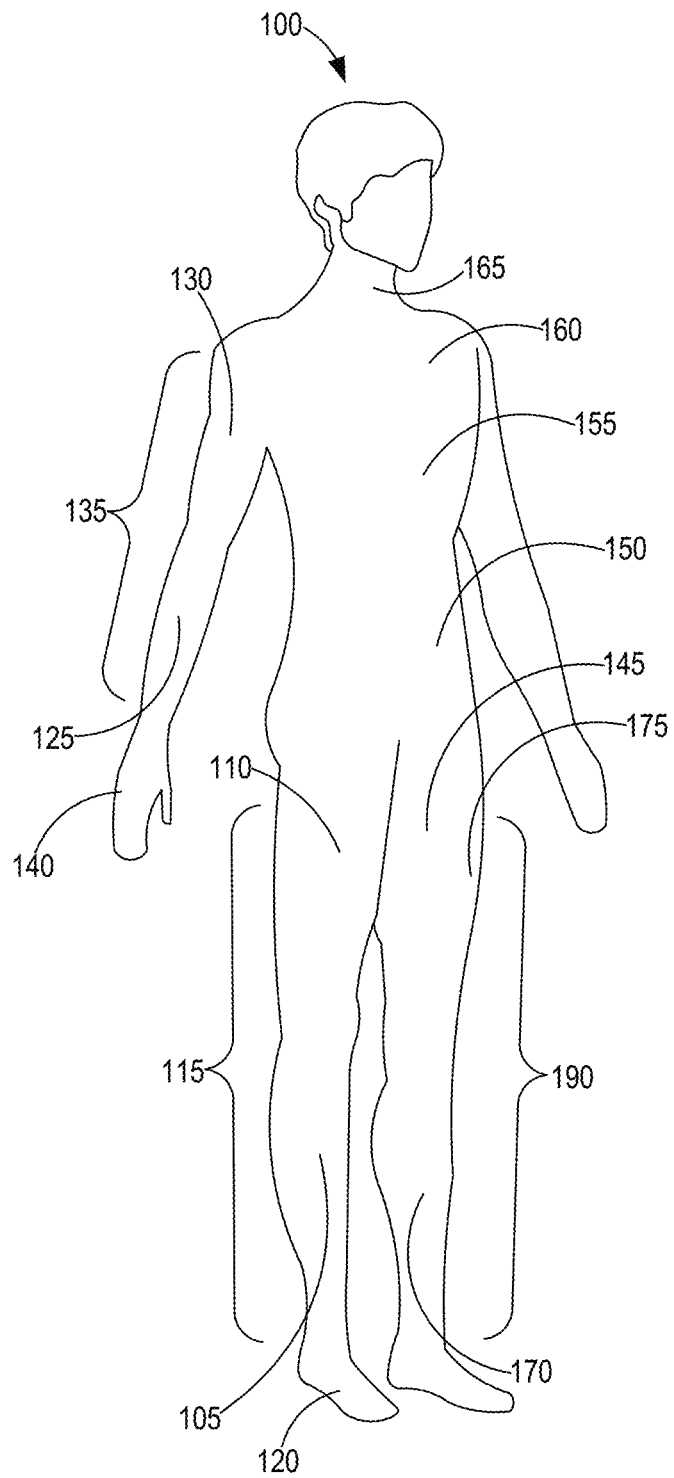
FIG. 1 illustrates examples of body parts or body areas in a generic human figure, in accordance with various embodiments of the present disclosure.

In the following detailed description, reference is made to the accompanying drawings, which form a part hereof, and within which are shown by way of illustration certain embodiments by which the subject matter of this disclosure may be practiced. It is to be understood that other embodiments may be utilized, and structural changes may be made without departing from the scope of the disclosure. In other words, illustrative embodiments and aspects are described below. But it will of course be appreciated that in the development of any such actual embodiment, numerous implementation-specific decisions must be made to achieve the developers' specific goals, such as compliance with system-related and business-related constraints, which may vary from one implementation to another. Moreover, it will be appreciated that such development effort might be complex and time-consuming but would nevertheless be a routine undertaking for those of ordinary skill in the art having the benefit of this disclosure.

Unless defined otherwise, all technical and scientific terms used herein have the same meaning as is commonly understood by one of ordinary skill in the art to which this disclosure belongs. If there is a plurality of definitions for a term herein, those in this section prevail unless stated otherwise.

Wherever the phrases "for example," "such as," "including" and the like are used herein, the phrase "and without limitation" is understood to follow unless explicitly stated otherwise.

The terms "comprising" and "including" and "involving" (and similarly "comprises" and "includes" and "involves") are used interchangeably and mean the same thing. Specifically, each of the terms is defined consistent with the common United States patent law definition of "comprising" and is therefore interpreted to be an open term meaning "at least the following" and is also interpreted not to exclude additional features, limitations, aspects, etc.

The term "consisting essentially of" is meant to exclude any features that would change the basic and novel characteristics of the present disclosure, as claimed.

The term "about" is meant to account for variations due to experimental error. All measurements or numbers are implicitly understood to be modified by the word about, even if the measurement or number is not explicitly modified by the word about.

The term "substantially" (or alternatively "effectively") is meant to permit deviations from the descriptive term that do not negatively impact the intended purpose. Descriptive terms are implicitly understood to be modified by the word substantially, even if the term is not explicitly modified by the word substantially.

"Anthropometry" means the measurement of the size and proportions of the human body. "Anthropometric measurements" are measurements that comprise information regarding the contour, volume, overall size and other relevant information for the subject body part or body area, where such measurements have relevance to the fitting of functional garments that are specifically sized for a person in need of fitting for such garments. In a specific, but non-limiting example, anthropometric measurements can be used to generate specifications for the fitting of medical/therapeutic compression garments for a person in need thereof, where such specifications—or "compression garment fit information"—has utility in the selection of prefabricated compression garments for a person or in the fabrication of custom compression garments for that person. Anthropometric measurements can also be utilized to provide information about the presence or absence of a medical or physical condition of interest. In the context of lymphedema (or an edema-like condition), the anthropometric measurements generated herein can be useful to identity the presence of body part or body area features associated with the accumulation (or absence thereof) of lymph fluid below a person's skin surface. Anthropometric measurements generated over time—that is, in a plurality of imaging events occurring at different times from which the anthropometric measurements can be derived therefrom—can also be used to generate information about a change in the physical condition of a person, such as in the gain or loss of muscle tone or weight loss that may (or may not) be associated with the person's wearing of a compression garment. Changes in the performance of a functional garment over time can also be determined, at least in part, from anthropometric measurements generated at different times for a person who has been wearing that garment.

The anthropometric measurements including one or more anatomic landmark locations obtained for an individual according to the methodology herein are, in implementations, "accurate." In the art of anthropometric measurements, "accurate" means the closeness of the measurements to a true value for the corresponding body part or body area for the subject individual. That is, if a first circumference of a first arm location on an individual has a true value of x centimeters as measured by an industry-accepted gold standard measuring technique, a circumference derived from a 3D reconstruction of the first arm at the first location will also be x centimeters, where the 3D reconstruction is derived from images acquired of that arm in a first-person imaging event. Put another way, the physically measured arm location circumference will be the same as the arm circumference derived from a 3D reconstruction of that arm at the same location. With regard to the accuracy of each of the one or more anatomic landmark locations, each of the landmark locations identified for an individual is substantially identical to the location of the corresponding anatomic landmark on the person's body part or body area in real life where that landmark location would be identified by palpation of the individual's body part by a highly trained clinician or other relevant person.

"Precision" in anthropometric measurements is associated with the variability between repeated measures by the same measurer (intra-measurer precision) or by different measurers (inter-measurer precision). "Reliability" refers to the consistency or repeatability of measurements, measurers, or instruments. "Dependability" is a function of physiological variation, such as biological factors, that may influence the reproducibility of the measure even if the technique used is exactly replicated each time. As would be appreciated, if there is not both good agreement between a plurality of anthropometric measurements for a patient, measurements and associated diagnoses and clinical observations for that patient over time cannot be assured to be "dependable."

In some implementations, anthropometric measurements including one or more anatomic landmark locations generated according to the methodology herein may not be accurate but may otherwise generate useful information because they are precise amongst a plurality of generated anthropometric measurements for a person that are generated in different imaging events for that person. That is, in some implementations, relative differences between different anthropometric measurements derived from 3D body part or body area reconstructions that may not be accurate vis a vis an actual physical measurement thereof can nonetheless be utilized. For example, arm circumferences derived from a plurality of 3D arm reconstructions generated for an individual in a plurality of imaging events may each differ from an actual physical measurement (i.e., by a tape measurement method) of that same arm at the same location in real life can each comprise a percentage difference from the physical measurement that is the same for each of the 3D arm reconstructions. If the arm at a first location is x centimeters in circumference in real life as measured by a tape measure, each of a plurality of arm circumferences derived from a plurality of 3D arm reconstructions generated in different imaging events of that person's arm at the same location will consistently exhibit the same percentage difference amongst each other. In other words, while the derived anthropometric measurements may not be accurate relative to a real-life measured arm circumference, each of the derived arm circumferences will be precise between and among each other, thus allowing changes to be seen objectively and reliably between a number of imaging events for a single person.

"Functional garments" or "functional clothing" for which the anthropometric measurements and other information generated herein can be used for the fitting can include one or more of:

Medical-functional clothing: includes functionalities like absorbency, air permeability and durability based on the wearer and requirements. This category includes functional garments used for healthcare or hygiene, surgical clothing, therapeutic clothing and intelligent functional clothing. "Medical-functional clothing" also includes medical/therapeutic compression garments, joint-braces, etc.

Protective clothing: functional garments that can provide the wearer protection from one or more hazards. This category can include protection against mechanical impact, physical injury (cuts, bites, perforation and abrasion), drowning, heat/fire, extreme cold, rain, electric shock, radiation, invisibility and dangerous substances and infective agents.

Sports-functional clothing: functional garments that can be used to enhance the functionality of sportspersons by providing a high level of breathability, moisture/vapor transfer, improve muscle activity, heat insulation, wind-proofing, waterproofing, and/or UV protection depending upon the sport and environment requirements.

Clothing for special needs: functional garments used to improve the quality or ease of life for people with disabilities or special needs, like wheelchair users, paraplegics, arthritis sufferers, people with restricted movement or stroke victims. These garments are mostly made-to-measure to ensure individual need fulfillment and comfort for the wearer.

Clothing for aesthetic enhancements: designed to sculpt and shape a wearer's body to achieve a desired aesthetic effect, by incorporating elastic, seams, or other features into a garment. Functionality can be incorporated into outerwear (e.g., intentionally constructed dresses, pants, etc.) or in undergarments (e.g., bras, girdles, etc.)

"Compression garment" in the medical/therapeutic- or sports-functional context means garments that are constructed from elastic material and that are intended to apply pressure to the body area when stretched over the skin while being worn. Such compression garments are worn over areas of the body where a therapeutic response (e.g., for treatment of lymphedema or swelling post-surgery, to address limb swelling, etc.) or, when used in sports-related applications, during or after exercise (e.g., for injury prevention or enhanced recovery of a person after athletic exertion). Medical/therapeutic- or sports-functional compression garments can be distinguished from garments that generate compression for aesthetic purposes (e.g., shapewear), however, all such garments are appropriate for fitting using anthropometric measurements for the subject person at least because for the intended purpose to be effective, the garment must fit the person's body part or body area correctly.

For medical/therapeutic or sports use cases where compression therapy is indicated or prescribed to address body part or body area swelling, application of compression is affected by addressing the function of a person's underlying lymph and vascular system. The lymph system is located below the skin surface, and to impart the appropriate functional compression on a person's lymph system as prescribed or intended, the location for appropriate fitting for a specific person will be inferred from outer locations on the person using traditional garment fitting methods. Such outer locations are associated with anatomic landmarks that are known to be relevant to the functional aspects of a person's lymph system. For example, for a leg compression garment, a primary therapeutic goal is to reduce the propensity of lymph fluid to accumulate at the lower leg area for a person who is symptomatic of lymphedema (or other edema-like conditions) in a subject leg when a person's lymph system is not functioning properly as a result of damage, injury, illness, etc.

As an example, a medical leg compression garment that is properly sized and that incorporates a correct amount of compression will help maintain the functionality of the lymph system vis a vis the subject body part or body area for a specific person by assisting in the regulation of lymph fluid therein. The intended function of a medical/therapeutic compression garment will be to appropriately act on the person's lymph system to impart the intended or prescribed therapeutic amount of compression to the person to reduce or eliminate the propensity of that person to accumulate fluid in that leg, and to prevent the negative medical and other effects that occur when the person becomes debilitated with edema/lymphedema. To impart this intended function, a medical/therapeutic leg compression garment for the treatment of edema-like conditions will be fitted from a distal body part location to a proximal location, wherein "proximal" is in relation to the trunk, with more compression being applied at the distal location, for example, from the ankle to the knee or groin. A higher amount of compression will be incorporated in the distal end of this medical compression garment to enhance the ability of the person's lymph system to transport lymph fluid from a distal end of an extremity to the trunk area. The circumference of a medical/therapeutic compression garment—for both medical and sports-related compression—will be configured to be smaller than the outer circumference of the body part or body area on which the garment will be worn, such that the garment has a circumference that is different from that of the body part or body area that is not under compression. When worn, the compression garment will be stretched to a circumference that allows the garment to fit the larger real-life circumference of the associated body part or body area, thus applying compression thereto in the prescribed or indicated amount. The resulting level of compression applied to the body part or body area is therefore associated with each of the garment size, the amount of stretching capability incorporated into the fabric, the level of compression incorporated in each of a plurality of locations in the garment, and how the garment is arranged on the person's body part or body area when the garment is worn. Fabrics for compression garments are typically engineered with a stretchable composition that incorporates elastomeric material to achieve both suitable stretch and desired compression.

The words "patient," "person," and "individual" may be used interchangeably herein to describe someone who is indicated for wearing of a functional garment, such as a compression garment, according to the methodology of the disclosure. Where relevant, the difference between a "patient," "person," and "individual" will be understood in context. For example, for a compression garment, a "patient" will be someone who is being treated for a medical condition by a doctor, clinician, or the like and for whom compression therapy will be medically indicated, whereas a "person" is someone who may wear a compression garment for comfort or sports performance, such as an athlete. When a specific "patient" or "person" is being described, the word "individual" may also be used herein.

"Edema" is the accumulation of excess fluid in a fluid compartment. This accumulation can occur in the cells (i.e., cellular edema), in the intercellular spaces within tissue (i.e., interstitial edema), or in other spaces in the body. Edema can be caused by a variety of factors, including indications associated with osmotic pressure, such as hypotonic fluid overload, which allows the movement of water into the intracellular space, or hypoproteinemia, which decreases the concentration of plasma proteins and permits the passage of fluid out of the blood vessels into the tissue spaces. Other factors can include poor lymphatic drainage (known as "lymphedema"), conditions associated with an increased capillary pressure (e.g., excessive retention of salt and/or water), heart failure, and conditions associated with increased capillary pressure, such as inflammation (e.g., burns or other trauma).

The term "lymphedema" may include either primary or secondary lymphedema, the latter of which might also be term "acquired" lymphedema. Some forms of lymphedema can occur in morbidly obese patients, such as the condition known clinically as "Massively Localized Lymphedema." Lymphedema is a category of edema, although it is also characterized as a separately treatable indication, such as when it is a complication of breast cancer treatments in which lymph activity in patients is affected. As would be recognized, primary lymphedema is caused by abnormal development of the lymph system. Symptoms can be present at birth or may appear later in life. Secondary lymphedema is caused by damage to the lymphatic system. The lymphatic system may be disrupted, damaged, or blocked by infection, injury, cancer, removal of lymph nodes, radiation to the affected area or scar tissue from radiation therapy or surgery. In some aspects, the present disclosure provides methods of detection of lymphedema that occurs because of removal or damage to lymph nodes that occurs after treatment of a patient for breast cancer. In this disclosure, the term "lymphedema" is a sub-set of "edema-like conditions." It is to be understood that even though a discussion may specifically discuss "lymphedema," the broader class of "edema-like conditions" is also applicable to that discussion unless the context implies otherwise.

In broad constructs, the disclosure herein provides systems and methods for generating accurate anthropometric measurements including one or more anatomic landmark locations for one or more body parts or body areas of interest for an individual (e.g., a patient, person, etc.) that are specific to fitting a particular type of functional garment for the individual's body part(s) or body area(s). The type of functional garment includes one or more functional fit characteristics that are associated with the functionality of the garment when worn by the person. These fit characteristics will, in turn, direct dictate the anthropometric measurements, which will include one or more anatomic landmark locations—necessary for appropriate fitting the garment for the individual so that the intended functionality is imparted to the person when the person is appropriately wearing the garment. The anthropometric measurements including one or more anatomic landmark locations for a body part or body area are derived from a 3D reconstruction of the body part or body area, where the 3D reconstruction is obtained from the processing of digital images of the individual. The body part or body area 3D reconstruction can be isolated or segmented from a 3D reconstruction obtained that incorporates a plurality of body parts or body areas for the individual. The anthropometric measurements including one or more anatomic landmark locations derived from each 3D reconstruction for a body part or body area of interest can include: 1) at least one anatomic landmark specific to proper fit of the chosen garment on the individual's body part(s) or body area(s); 2) a circumference for each of the anatomic landmark locations; and 3) length information. The anthropometric measurements including one or more anatomic landmark locations derived from the body part or body area 3D reconstruction are accurate vis a vis a corresponding one or more body part or body area on the individual in real life. In implementations, the derived anthropometric measurements including one or more anatomic landmark locations are directly derivable from the segmented or isolated body part or body area 3D reconstructions substantially without human supervision. The derived anthropometric measurements including one or more anatomic landmark locations can be suitable for the generation of fit instructions useful for the fitting of functional garments on one or more body parts or body areas for a person in need thereof.

As would be understood, to properly fit a functional garment, the garment must fit appropriately on the subject body part or body area so as to be able to effectively provide the function intended to be imparted by that garment. The inventors herein have developed a method to allow the at least partially automated detection of one or more anatomic landmark locations that are relevant to the fitting of a medical/therapeutic compression garment for a person in need thereof. More broadly, the methodology can be used to identify anatomic landmark locations and other pertinent measurements for fitting of functional garments where such anatomic landmark location identification is relevant to the fitting of such garments. Such at least partially automatic anatomic landmark location identification for garment fitting is an improvement over prior art methodologies that require anatomic landmark locations to be identified visually and/or by palpitation of the patient's skin to identify anatomic features on the patient that may not be visible from the patient's skin surface. In this regard, the present methodology provides for contact-less anatomic landmark location identification. Moreover, the present methodology allows anatomic landmark locations, and other body part or body area measurements, to be obtained directly from images of a person in need of fitting for functional garments.

In the context of the non-limiting example of a medical/therapeutic compression garment, the effectiveness of the compression therapy is highly associated with the proper placement of the compression garment relative to the physiology of the patient's underlying lymph and vascular system. It follows that for the correct application of compression therapy to a patient in need thereof, compression garment fit information necessitates generating outer circumference information for at least the relevant anatomic landmark locations. Identification of those anatomic landmark locations associated with imparting the prescribed or intended amount of compression therapy is therefore a pre-requisite for proper fitting of the compression garment.

In one non-limiting aspect, the anthropometric measurements that include one or more anatomic landmark locations associated with the fitting of a functional garment are generated from body part or body area 3D reconstructions generated according to methodology implementing an imaging technique as disclosed in U.S. Pat. Nos. 10,045,581 and 10,251,438, the disclosures of which are incorporated herein in their entireties by this reference (the "'581 and '438 Patents"). To summarize that methodology, a hand-held imaging device is used to acquire a plurality of images of each area of interest for one or more body parts or body areas where the imaging device is moved around the body part or body area with six degrees of freedom, unconstrained by a mounting or support. The plurality of images acquired in the imaging event are processed to generate a 3D reconstruction of all or part of the body of that person. The inventors have determined that this technique can be useful to obtain body part or body area 3D reconstructions from which the anthropometric measurements including one or more anatomic landmark locations can be derived, at least because the body part or body area 3D reconstructions so obtained comprise mathematically accurate information—that is, each generated 3D reconstruction comprises geometric information that matches the real-life shape of the actual body parts or body areas. Circumference information for the subject body part or body area are directly derivable therefrom, as is length information, using that prior art methodology.

As discussed further hereinafter, the imaging method whereby a handheld imaging device is moved around a hand with 6 degrees of freedom unconstrained by a mounting or a support can be used to generate measurements of an entirety of a hand, including one more circumferences of each finger and the thumb, circumference of one or more palm areas, the wrist, and a forearm area. Lengths of each finger and thumb and of other areas can be derived from the acquired images. Such methodology can provide accurate measurements of a hand even though a palm-facing portion of the hand is not included in the images.

The body part or body area 3D reconstruction obtained from the referenced methodology substantially matches the body part or body area as it exists in real life and that is substantially identical to the body part or body area for the actual patient; that is, the subject methodology provides a mathematically accurate 3D reconstruction of the person's body part or body area. The inventors have described this 3D reconstruction in the '581 and '438 Patents as a "shape description," to contrast it from a "shape representation" that replicates the shape of the body part or body area but not the geometric or mathematical information of the body part or body area. Methodology developed by the inventors herein to accurately identify the one or more landmark locations using such shape descriptions is discussed hereinafter.

While the shape description methodology described in the "'581 and '438 Patents has been found to be highly suitable to achieve the improvements herein, the disclosure is not limited to 3D reconstructions generated by this method. To the contrary, body part or body area 3D reconstructions can be generated via a vertical full 3D reconstruction of a person. The 3D reconstructions can further be generated from images generated from a handheld scanner that is moved around the patient using a fixed axis upon which the scanner rotates around each body part or body area. In another implementation, the images can be generated from a person who is standing in a scanning booth configured as a plurality of cameras, as disclosed in U.S. Pat. No. 10,628,666, the disclosure of which is incorporated herein in its entirety by this reference. Still further, the 3D reconstructions can be generated from a scanning method in which a stationary imaging device acquires images of a patient who is rotating on a turntable, as is disclosed in U.S. Pat. No. 10,628,729, the disclosure of which is incorporated herein in its entirety by this reference, can also provide 3D reconstructions from which anthropometric measurements including one or more anatomic landmark locations can be generated.

In some implementations, the body part or body area 3D reconstructions generated from an imaging event may not be mathematically accurate vis a vis the actual real-life body part or body area for the individual. That is, they may be "shape representations," rather than "shape description." Such body part or body area 3D reconstructions in the form of shape representation can be made mathematically accurate—that is, they can be transformed into shape descriptions—by using a reference scale to align a generated 3D reconstruction with the dimensions of the subject body part or body area in real life.

Digital imaging techniques that are suitably used to generate 3D reconstructions of an individual body part or body area, such as that used in the '581 and '438 Patents, can be stitched together to generate a collection of 3D reconstructions of a larger body section or even for the full body. This collection of 3D reconstructions can allow a more holistic viewing of a patient, such as in the patient digital twin application discussed hereinafter, while still providing accurate 3D reconstructions of each body part or body area of interest, such as would be more appropriate in healthcare implementations than generating a full 3D reconstruction that may not allow the individual aspects of each body part to be fully resolved.

An improvement to the prior art obtained from the methodology herein is the previously unrealized ability to automatically derive one or more anatomic landmark locations associated with proper functional garment fitting from each of the 3D reconstructions for the subject body part or body area, where such one or more anatomic landmark locations are accurately placed vis a vis the person's real-life body part or body area. As noted, such proper anatomic landmark locations are relevant to imparting the intended functionality from the garment when the garment is worn by the person in an intended use scenario. In the course of their extensive clinical work with patients who are or potentially are symptomatic of lymphedema, the inventors have discovered that accuracy of medical/therapeutic compression garment fitting derived from digital imaging of the person cannot be assured unless the anatomic landmark locations relevant to imparting the function of the compression on the subject body part can be accurately identified for a person in need of fitting. Moreover, in comparing compression garment fitting results obtained from the subject body part or body area 3D reconstructions according to the disclosed methodology with tape measurement fittings made according to the prior art, the inventors surprisingly found that it is common for even trained clinicians to incorrectly identify anatomic landmark locations on some people. In fact, clinical testing conducted by the inventors herein has shown that the inter-operator variability of landmark location identification is reduced by about 75% with the disclosed methodology anthropometric measurement methodology comprising at least one anatomic landmark location as compared to trained clinicians with a tape measure, and the disclosed methodology resulted in a significantly improved garment fit compared to manually fit garments from trained clinicians. Notably, these results were even more pronounced among those persons who are obese and/or who present with non-standard body shapes (e.g., lobes, nodes, or folds). Such persons are often those who are most in need of properly fitted compression garments; thus, inaccurate compression garment fitting can be more significant with such persons and the present methodology is capable of providing substantial improvement to the patients with the greatest need for therapy. Through extensive research, data collection, and analysis, the inventors herein have discovered that it is possible to generate anatomic landmark location information directly from body part or body area 3D reconstructions generated from an imaging event for a first person. This discovery has been found to enable not only improvements in the fitting of compression garments for a person in need of compression therapy, but also for the fitting of the broader class of "functional garments." This approach has a distinct advantage over some digital imagery and 3D scanning techniques in the prior art in that it does not require markers to be placed on the body, it does not require an external reference scale, and it is not dependent upon a specific body position or pose, which makes the approach easier to execute and more accommodating of individual differences among subjects.

Because the methodology of the present disclosure substantially removes the human element from the generation of anatomic landmark location information, outer circumference, and length information for an individual, functional garments, for example, therapeutic/medical compression garments, can be generated substantially without the need for a human to touch a person to obtain accurate anthropometric measurements of a person. Thus, the method can allow anthropometric measurements including one or more anatomic landmark locations to be generated from several feet away, or even in a virtual environment, such as when the imaging device is operated remotely.

Further, the methodology provides significant improvements over prior measurement methodology in which substantial variability can be found between different measurement events for a single individual and between multiple individuals, especially when each measurement is made by different individuals. By way of example, a first clinician may have generated a personal methodology that identifies for each of her measurements a location for an anatomic landmark that is slightly different than that which a second clinician generates a landmark for that same individual. It follows that, as between measurements for the same individual conducted by different clinicians, generated anthropometric measurements for that individual may differ due to the fact that the measurements have been conducted by different clinicians using slightly different techniques and not because the subject body part or body area actually exhibits a difference in anthropometric measurements for that individual. By substantially eliminating the inter-clinician variability in the generation of anthropometric measurements for a single individual, single time point measurements are more precise, and any differences seen in an individual over time (e.g., in a first and second measurement event) can be more accurately attributed to real differences in the body part or body area of interest.

Still further, the use of a methodology that substantially eliminates the human element from the generation of anthropometric measurements used for functional garment fitting can allow measurements for each of a plurality of individuals to be appropriately compared in an objective fashion. For example, anthropometric measurements including one or more anatomic landmark locations for a first person and a second person can be compared along with other relevant information to assess the effectiveness (or lack thereof) of therapeutic treatments, lifestyle, personal events, etc. Still further, by generating a collection of anthropometric measurements including one or more anatomic landmark locations for a plurality of individuals where the measurements are both accurate and precise, such anthropometric information can be configured for use as anthropometric information for use in subsequent anthropometric measurement events, as well as for other purposes, as discussed further hereinafter.

The inventors have recognized that generation of anthropometric measurements including one or more anatomic landmark locations that are accurate for an individual and among a plurality of individuals can be facilitated, at least in part, by use of standardized or normalized body part or body area models that can allow the identification of one or more anatomic landmark locations relevant to the fitting of functional garments from 3D reconstructions of body part or body areas of interest according to the methodology herein. Notably, the inventors have determined that as long as images that include the body part or body area of interest can be rendered into 3D reconstruction of the body part or body area of interest that is accurate vis a vis the real-life body part or body area for a person, anatomic landmark locations relevant to the fitting of a type of functional clothing can be accurately derived therefrom. In conjunction with outer circumference and length measurements that are also relevant for a specific functional garment type that were previously obtainable from digital imaging as described in the '581 and '438 Patents, one or more anatomic landmark locations associated with the fitting of a functional garment can be generated from the improvements described herein.

The inventors have determined that use of an invariant scale methodology described herein can allow anatomic landmark locations for an individual to be accurately resolved from a body part or body area 3D reconstruction for an individual substantially independently of the shape, size, or configuration of the subject one or more body parts or body areas with which an individual presents. The inventors have determined that use of an invariant scale methodology that normalizes each body part or body area for different people substantially independently of a person's size and shape presentation can allow anatomic landmarks of interest, and therefore the locations thereof on an individual's corresponding body part or body area in real life, to be accurately derived from a generated body part or body area 3D reconstruction. When combined with other measurements derivable from the 3D reconstruction the derivation of anthropometric measurements useful in fitting of functional garments, such as compression garments, for the specific individual can be generated. For example, anatomic leg landmark locations relevant to the fit of a functional garment will manifest differently on a subject with long legs as compared to short legs and on a subject with lean legs as compared to obese legs. The methodology herein enables an image-based protocol for relevant functional garment anatomic landmark location identification for application to all individuals in need of fitting thereof regardless of body shape and size.

The identification of each of the anatomic landmark locations of interest for an individual will be consistent from person to person at least because the methodology does not incorporate the error or variability inherent with human measurement techniques. It follows that such objective and consistent anatomic landmark location identification can provide useful information for the fitting of garments that are intended to be fitted for one or more purposes, that is, for functional garment fitting. Moreover, such objective and consistent anatomic landmark location identification can allow differences in a single person to be detected from 3D imaging longitudinally, and for a plurality of persons in comparison with each other at a single time or longitudinally from images generated from the person or persons and comparison thereof. The ability to accurately identify anatomic landmark locations is therefore an improvement over prior art methodologies, as would be appreciated.

By way of explanation, through their extensive clinical research in imaging persons and generating compression garment fitting measurements therefrom, the inventors have recognized that, while people may possess highly varied body part and body area shapes, the process used to identify each person's anatomic landmark locations that dictate the fit of a garment that is engineered to be worn to impart a particular function can be made to be consistent amongst different people using the methodology herein. That is, and as a non-limiting example, therapeutic/medical compression garments can be engineered to enhance the ability of the wearer's lymph system to transfer fluid away from an extremity toward the person's trunk area. To impart this functionality, a lower leg compression garment can be engineered to impart a higher amount of compression at the distal end of the garment and to impart a lower compression at the proximal end of the garment. Conventionally, a lower leg compression garment will be fitted at least based upon an identified landmark location at the distal end of the garment in the ankle region and an anatomic landmark location at the proximal end of the compression garment in the calf or popliteal region. A tall person and a short person will each have an ankle landmark location and a popliteal landmark location, as will a thin person and an obese person. To accurately fit each of these people with a compression garment, as well as any other person, the anthropometric measurements used must be able to accurately identify the anatomic landmark locations relevant to the proper fitting of the compression garment on the subject's body region. To this end, the present methodology generates one or more body part or body area 3D reconstruction segments for a person, where the body part or body area 3D reconstruction segment is referenced to the location of identified anatomic reference landmarks discussed elsewhere herein and the segmented/isolated reconstructions can be normalized based upon the position of the reference anatomic landmarks thereon to transform the body part or body area segment into a scale invariant version. Each scale invariant 3D reconstruction can be further processed to derive additional anatomic landmark locations appropriate for proper garment fitting from each body part or body area in need of fitting with a functional garment.

In a significant implementation, the present disclosure comprises a multi-step process that derives an individual's anatomic shape characteristics relevant to functional garment fitting—or "anthropometric measurements including one or more anatomic landmark locations"—for one or more body parts or body areas of interest from a 3D reconstruction of one or more body parts or body areas of interest for an individual.

In a first step of the process, the methodology identifies or isolates one or more body regions from a 3D reconstruction derived from digital images or a 3D scan of a first person, where the 3D reconstruction can be generated from each of one or more imaging methods as described elsewhere herein. The inventors have found that as long as a 3D reconstruction is of reasonably high quality—either as generated in the first order from the imaging or by way of correction or augmentation using known methods—the sources of the 3D reconstruction from which a body part or body area 3D reconstruction is derived can be numerous.

In a non-limiting example, the system can be configured to isolate or segment a generated 3D reconstruction of all or part of a person's body to provide a body part or body area 3D reconstruction for a body part or body area of interest on the person. For example, a 3D reconstruction for substantially all of the first person can be processed to select (or "segment" or "isolate") legs, trunk, arms, head, hands, etc. for that person as separate 3D reconstructions that include only a single body part or body area.

In a non-limiting example where the generated images include a lower body region, a 3D reconstruction can be generated from image processing to position the first person on a floor area while standing when information indicates that the images were generated when the person was standing on a floor. In this case, the foot/floor boundary will comprise a first end of a body region or area of interest on a leg. A body area or region of interest can also be identified while the person is sitting, if appropriate, and information associated with a 3D reconstruction generated from a seated position can be used therewith. A proximal boundary of a leg segment can be determined as appropriate for the application as the leg/trunk boundary in the gluteal fold region, the thigh region, or the knee region, among others. In some implementations, information derivable from a library of information comprising validated information about leg shape, foot, or knee location, etc. generated from previous image processing events can be used in the processing of images for a first person.

For a body part or body area 3D reconstruction that is an arm region, the distal end of the arm region can be isolated from a 3D reconstruction by identifying an end of one or more of the fingers on the hand, as the hand/wrist boundary, by differences in shape or size at a distal region of an arm, or by any other suitable method. A proximal boundary of an arm segment can be determined as appropriate for the application as the armpit or axilla region, the deltoid region, or the elbow region, among others. In some implementations, information derivable from a library of information comprising validated information about arm shape, hand location, etc. generated from previous image processing events for the person or a plurality of persons can be used in the processing of images for a first person.

In some implementations, information derivable from a library of information comprising validated information about previous imaging events for a plurality of persons can be used in the processing of images for a first person, for example, holes or missing areas from the processing of the images can be filled in using a priori information associated with previous imaging and anthropometric measurements generated for that individual or from a collection of information generated from a plurality of imaging events for a plurality of persons. Such a priori information can be included in a library of information for application herein. For example, for images that do not show clear separation between individual body parts or body areas (e.g., between the legs or at the armpit region), the images can be processed to allow isolation or segmentation of the 3D reconstruction as an individual body part or body area. As would be appreciated, the use of previously validated a priori information present in libraries of information can improve the accuracy of, and confidence levels for, generated 3D reconstructions for a body part or body area generated from imaging events. As would be appreciated, use of such validated information can provide ground truth information from which subsequent anthropometric measurements including one or more anatomic landmark locations for a person of interest for fitting with compression garments can be derived. In turn, anthropometric measurements including one or more anatomic landmark locations derivable therefrom can also be generated with a higher level of confidence in the accuracy thereof at least because the previously generated information can be used to generate training sets used to derive subsequent measurements. Such training sets can be used to allow the automated generation of anthropometric measurements including one or more anatomic landmark locations.

Referring to a generic human figure in FIG. 1, one or more body parts or body areas of interest for a patient 100 can be isolated or segmented from the generated 3D reconstructions as a number of body parts or body areas such as:

Lower right leg 105
Upper right leg 110
Entire right leg 115
Right foot 120
Lower right arm 125
Upper right arm 130
Entire right arm 135
Right hand 140
Crotch region 145
Abdomen region 150
Chest/bust region 155
Shoulder region 160
Neck region 165
Lower left leg 170
Upper left leg 175
Entire left leg 180

Once the first person's body part or body areas are segmented or isolated as individual 3D reconstructions for the first person each generated 3D reconstruction can be translated, rotated, and otherwise manipulated as appropriate to be aligned to a universal coordinate system. In this regard, the inventors have determined that alignment of each segmented/isolated body part or body area 3D reconstruction to a universal coordinate system substantially reduces variability related to stance and body position, thus enabling consistent, repeatable analysis between and among a plurality of individuals.

Once aligned with this uniform 3D body part or body area coordinate system, the first-person body part or body area 3D reconstruction can be processed to identify one or more anatomic landmark locations for the first person on that body part or body area, where the identified anatomic landmark locations are associated with a functional garment intended for fitting on the subject person. In a non-limiting example where a body part or body area of interest is the first person's leg, the at least two identified anatomic landmark locations identified from the 3D reconstruction on the leg can be each of the ankle, top of the thigh, and/or the knee as anatomic landmarks. In a non-limiting example, the ankle location for the individual can be identified as the location of the smallest circumference above the foot derivable from the leg-area 3D reconstruction, where the bottom of the foot is located adjacent to a floor location. For some persons, a clear difference may exist for the circumference of an ankle area, so that the ankle can be derived directly from that person's leg area 3D reconstruction. Any direct identification can be confirmed against a priori information derived from a population of people which could, in implementations, include previous imaging of and/or garment fitting for that individual. For other people, there may not be a clear circumference distinction at the ankle area, such as when a person is obese and/or is symptomatic of lymphedema. In such a case, the 3D reconstruction of the person's leg area can be processed according to one or more methods as discussed hereinafter, including with a priori information derived from a plurality of individuals.

Moving along the leg, the knee anatomic landmark location can be identified from a curvature derivable from the 3D reconstruction at the knee crease, with or without use of a priori information indicating where the knee anatomic landmark location is known to be for a population of people having characteristics that are the same or different from the person. The top of the thigh location for the person can be identified from a curvature at a location in the 3D reconstruction that is observable directly from the 3D reconstruction, also with or without use of a priori information to be at a location where the gluteal fold anatomic landmark is located.

As discussed, each functional garment will comprise a plurality of fit characteristics that are associated with an intended function associated with the subject garment when it is worn by a person. In the context of a therapeutic/medical compression garment configured to impart a prescribed or intended amount of compression therapy to a person in need thereof, compression is applied to the underlying lymph and vascular system in the person when the garment is worn as indicated. When the subject compression garment is a leg compression garment that is worn below the knee, the relevant anatomic landmarks to impart the intended functionality when worn by a person are at least the ankle and the calf and/or popliteal area, where a first amount of compression will be included at the ankle (or distal) location a second amount of compression will be included at or above the ankle (or proximal) location, for example at or below the popliteal region. Thus, when anthropometric measurements including one or more anatomic landmarks are derived from a leg 3D reconstruction for use in the fitting of a medical/therapeutic compression garment, at least the locations of the ankle and popliteal anatomic landmarks will be derived therefrom, along with circumferences for each of these anatomic landmark locations, as well as other locations in between as appropriate for fitting of the garment on the person's lower leg and at least a length of the distance between the distal and proximal anatomic landmark locations.

In further implementations, identified regional anatomic landmark locations for the first person can be further analyzed to generate additional regional anatomic landmarks associated with the fitting of a functional garment of interest. For a functional garment that is a medical/therapeutic compression garment that is intended for fitting on a person's leg, additional anatomic landmark locations in between the distal and proximal anatomic landmark locations can be identified from the segmented/isolated leg 3D reconstruction, such one or more areas along the calf, for example, the widest area, which can be relevant to ensuring that the subject compression garment is comfortable when worn. For example, a person with a very wide calf area may need a compression garment configured with a larger sized calf area than would normally be present in a standard-sized leg compression garment. For a full leg compression garment, at least two anatomic landmark locations above the knee can include the thigh and gluteal fold, again being configured to enhance not only efficacy of compression therapy for that person's body part or body area, but also to better ensure that the garment is comfortable for the person.

The methodology can incorporate a step of analyzing an isolated/segmented 3D reconstruction of a person's body part or body area of interest to identify a processing method from which one or more anatomic landmark locations can be derived from the 3D reconstruction. This process can implicate one or more calculation techniques as appropriate to a specific shape of the person, where such calculation techniques have been developed by the inventors after extensive clinical research and that have been incorporated herein. In this regard, the inventors herein have determined that while the population of individuals that can be imaged so as to obtain anthropometric measurement including one or more anatomic landmark locations and, optionally, associated functional garment fitting information may be very different in body part or body area shape, there is a discrete set of analysis techniques from which the information can be systematically derived.

A body part or body area 3D reconstruction processing method suitable to generate accurate anatomic landmark location information for proper garment fitting from an isolated/segmented 3D reconstruction for a first person can be selected by use of a priori knowledge of the identity and location of anatomic landmark locations for persons who have such body part or body area characteristics. Such a priori knowledge can include fit instructions provided by manufacturers of functional garments. Such fit instructions will indicate where anatomic landmarks relevant to the intended function of the garment are to be located vis a vis the subject garment. For example, for a medical/therapeutic compression garment, a manufacturer's fit instructions that direct a clinician to collect the plurality of measurements to be generated in real life by the tape measurement method provides useful information for use in determining the anatomic landmark locations from the present methodology. Such instructions, along with any additional garment-specific measuring or sizing protocols can be used to seed the anatomic landmark location identification system for use in automated or at least partially automated measurement functional garment fitting events. Other information, such as anatomical reference data used in medical training materials, can also be included to seed the fitting process. Moreover, as the libraries of information generated in the present methodology are populated with validated body part or body area measurement derived from actual patients obtained in previous measurement and/or functional garment fitting events, such information can be used to confirm the accuracy of a subsequent anatomic landmark location identification by comparing the validated library information with the result returned by the system for a patient. Engineering and wear characteristics of fabrics, materials, etc. can also be included in as a priori information to better ensure that a subject functional garment will fit appropriately when worn by the person. Once the pertinent garment fit landmarks are determined for the particular garment, the relevant body regions of the individual necessary for landmark identification can be defined, and the process of determining the location of the anatomic landmarks on the individual and generating the functional garment fit information for a person in need of fitting therewith can occur.

For example, the locations of an ankle region and a knee region may be identifiable from a 3D leg reconstruction using the methodology herein, at least because a person having a known height will likely have an ankle region and knee region within a certain range of values. Such range of values can be derived from fit information provided by one or more compression garment manufacturers, for example. The leg 3D reconstruction for a person can be searched within this range of values to identify the unique shape characteristics of the individual that are most likely to be associated with the person's ankle and knee location, where the likelihood is derivable from a priori information. That is, the previously identified anatomic landmark locations can serve as reference landmarks for the identification of other anatomic landmarks specific for a functional garment to be fitted on that person.

In the example of a medical/therapeutic lower leg compression garment, the location of the popliteal landmark can be resolved from the identification of the person's knee and ankle locations based partially upon the known location of the popliteal relative to these anatomic locations in a generic person—the identity of which is facilitated by the use of the invariant scale (the universal coordinate system) as discussed elsewhere herein. This methodology allows anatomic landmark locations to be derivable from the 3D reconstructions even when the person has minimal contour on her body part or body area.

The characteristics of each body part or body area shape as present in the 3D reconstruction can be compared to previously collected body shape information for which anatomic landmark information has previously been identified for that person or for a plurality of persons. Such a priori body part or body area shape information can inform the type of processing needed to derive accurate anatomic landmark information from a specific person's isolated/segmented 3D reconstruction. At least one method can be selected for the processing of the person's isolated/segmented body part or body area 3D reconstruction, where the method is selected to generate an anatomic landmark location identification having a high degree of confidence in the accuracy thereof. In further implementations, each of a plurality of body part or body area 3D reconstruction processing techniques can be used to better ensure that each anatomic landmark location identification for each person is, in fact, accurately determined. In this regard, at least two or more processing techniques can be used to generate the relevant anatomic landmark locations for each isolated/segmented body part or body area 3D reconstruction.

As a first processing step for the generation of anthropometric measurements including one or more anatomic landmark locations from each body part or body area 3D reconstruction, a plurality of stacked sections can be provided. The number of stacked sections generated from the body part or body area 3D reconstruction can vary, with a minimum being at least 5 along a leg area, for example. As would be appreciated, a larger number of stacked sections can provide enhanced resolution of a body part or body area to allow characteristics therein to be identified. However, depending on the characteristics of the subject body part or body area, improved resolution can also obscure differences along the length of the body part or body area, where such differences may be relevant to the fitting of the functional garment. In an implementation, the subject body part or body area reconstruction can be analyzed to determine the number of stacked sections needed to accurately identify the relevant anatomic landmark locations for a subject functional garment.

In one exemplary processing methodology that can be used for persons with pronounced body part or body area contour in real-life, at least some anatomic landmark location information can be directly derivable from the 3D reconstruction of that person's leg. For such highly contoured body parts or body areas, anatomic landmark location information for a body part or body area of interest can be derived from the body part or body area 3D reconstruction using a combination of circumference measurements along a length of such body part or body area to provide a plurality of stacked sections. At least some anatomic landmark information can be generated from an analysis of the generated shape of the stacked sections as present in 3D reconstruction. For example, for the purpose of identifying landmarks for proper lower leg compression garment fit, a minimum circumference at the distal area of the leg could be identified as an ankle landmark, a largest circumference below the knee could be identified as a mid-calf landmark, and a minimum circumference below the knee and above the mid-calf could be the popliteal landmark. In this example, the functional advantage of defining the ankle landmark as the location with the smallest circumference and the calf landmark as the location with the largest circumference is that it sets the upper and lower circumference bounds for the determination of the pressure gradient within the garment. Furthermore, defining the popliteal landmark as the location with the local minimum circumference between the calf and the knee serves to set the upper boundary of the garment in an anatomic region in which the elastic of the garment will anchor on the leg, thus holding the garment in place and preventing the garment from falling down.

As would be appreciated, the "sharper" the differentiations in the areas of a subject body part or body area, the fewer cross-sectional outer circumference slices that may need to be generated to define distinctions between relevant anatomic landmark locations thereon. However, use of a 3D reconstruction to generate the information can allow any number of cross-sectional slices to be generated for plotting thereof as the first derivative.

Figure 2B:
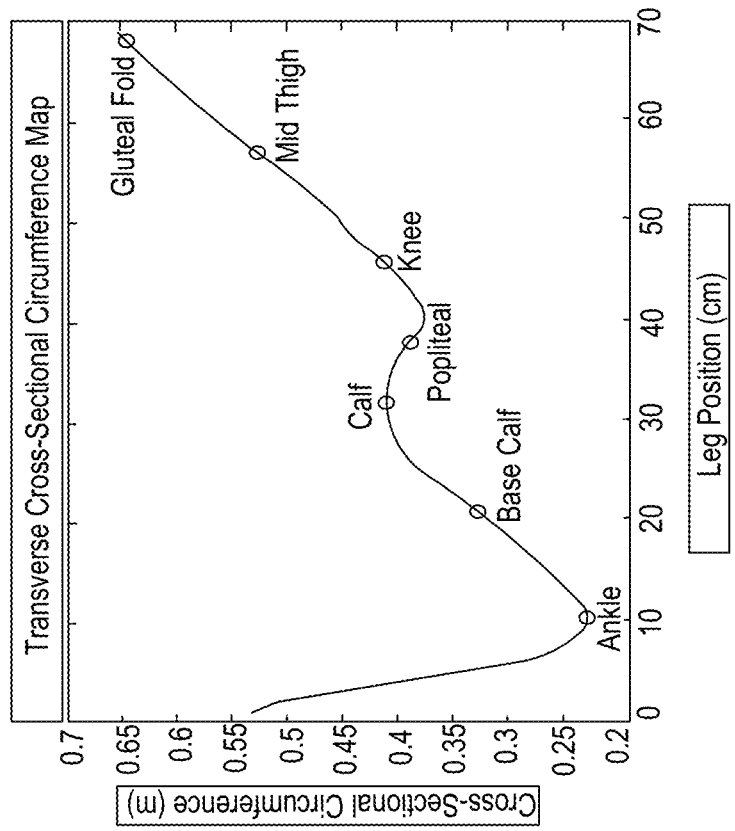
FIGS. 2B, 3B and 4B illustrate examples of cross-sectional circumferences of the 3D reconstructions of FIGS. 2A, 3A and 4A, respectively, in accordance with various embodiments of the present disclosure.
Figure 3B:
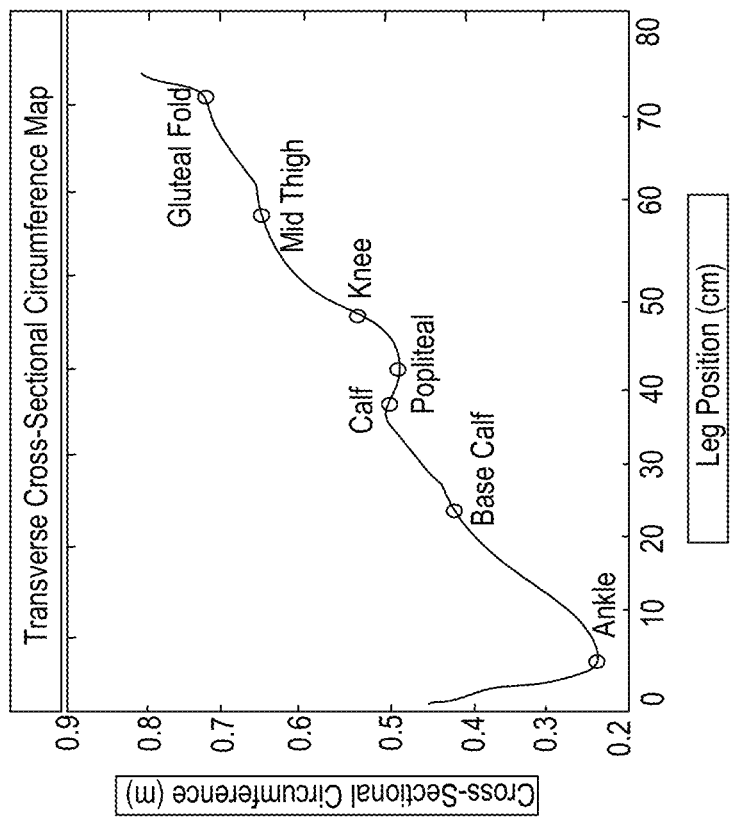
Figure 3A:
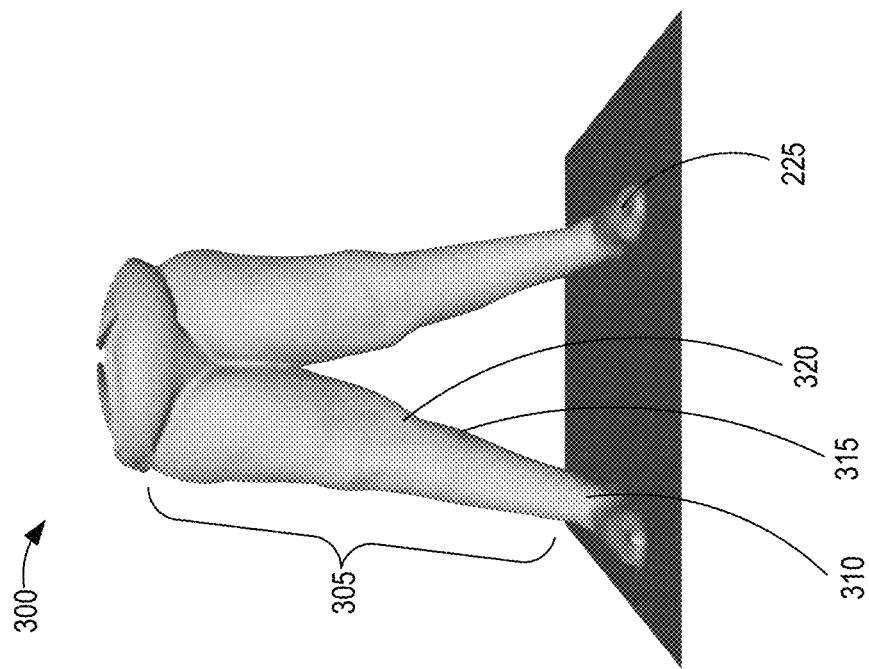
Figure 4B:
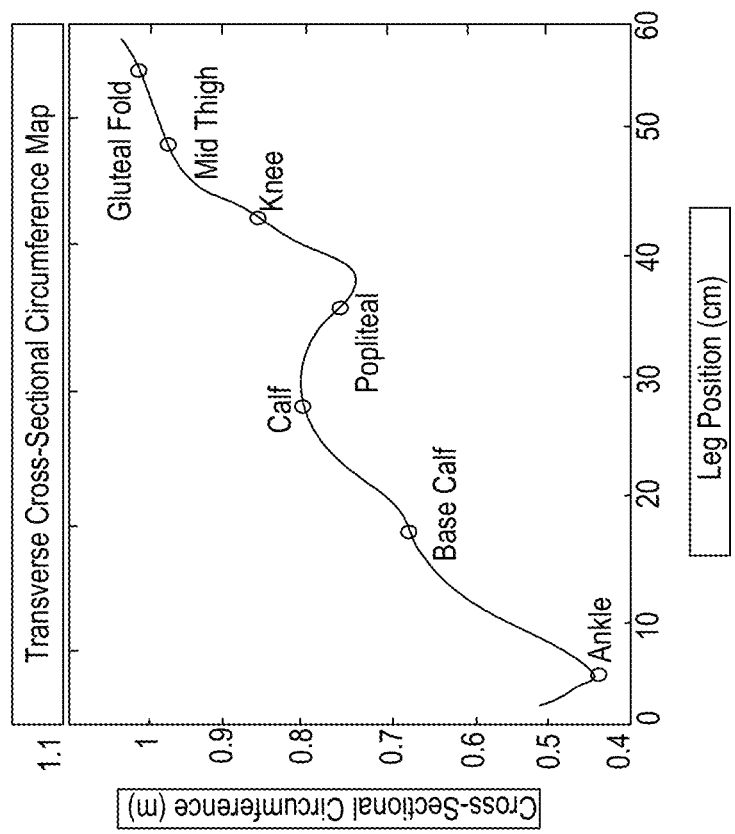

For persons without pronounced contour along the subject body part or body area—the presence or absence thereof can be determined by processing of the 3D reconstruction—a surface derivative profile can be generated from the surface profile obtained from the stacked sections derived from the isolated/segmented body part or body area 3D reconstruction. In this example, the plurality of circumferences arranged as stacked sections are processed to refine the differences using higher order mathematical calculations such as first and second circumference derivatives, two-dimensional and three-dimensional surface profilometry, and multi-dimensional contour derivatives, among others. As shown for the 3D reconstructions of FIGS. 2A, 3A, and 4A, relevant anatomic landmark locations for a lower leg medical/therapeutic compression garment can be identified from individuals 200, 300, and 400 as derivatives generated from leg 3D reconstructions 205, 305, and 405 in FIGS. 2A, 3A, and 4A, respectively: ankle (210, 310, 410), mid-calf (215, 315, 415), knee (220, 320, 420). Floor 225 is shown as a lower reference for each of 3D leg reconstructions 205, 305, and 405. (As would be appreciated, the circumferences shown in FIGS. 2B, 3B, and 4B are for the legs 205, 305, and 405.)

Figure 2A:
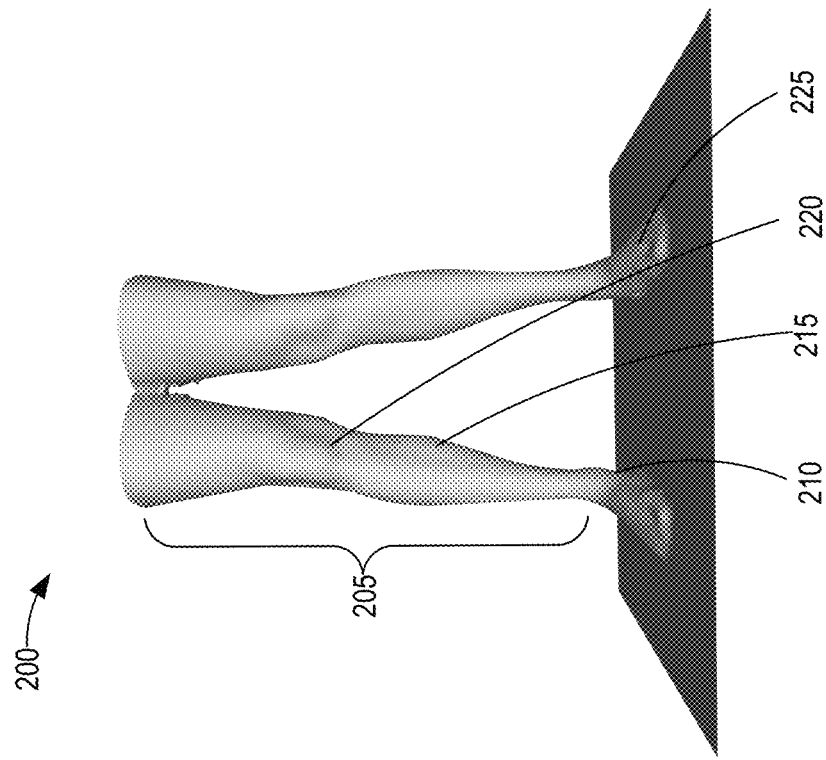
FIGS. 2A, 3A and 4A illustrate examples of 3D reconstructions of three leg morphologies, in accordance with various embodiments of the present disclosure.

For some 3D body part resolutions, transverse differences in outer circumference measurements along the length of the limb can allow anatomic landmark locations to be resolved directly therefrom, such as for patients who present with well-defined body part or body areas, such as with the individual associated with the leg 3D reconstruction in FIG. 2A. However, the inventors have determined that anatomic landmark locations can be resolved even more distinctly when outer cross-sectional circumferences are analyzed as first or second derivatives, especially in combination with surface contour profiles, which can be mapped along the anterior, posterior, medial, and lateral surfaces as appropriate for each landmark of interest. Moreover, for some individuals, the simultaneous or sequential combination of one or more processing techniques can facilitate accurate resolution of the at least two anatomic landmark locations therefrom.

Figure 4A:
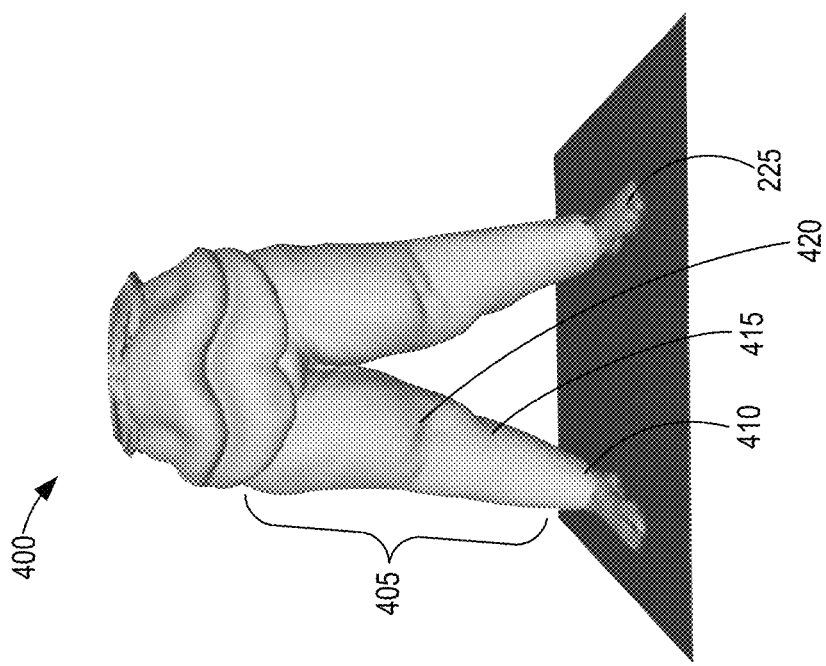

The inventors have recognized that even for the most distorted body part or body area— such as in a body part or body area having "complex morphology" such as nodes, lobes, or folds as shown in FIG. 4A as 3D reconstruction 405—a first or second derivative of outer circumferences of a body part or body area of interest, especially in combination with surface profile mapping and axial contour derivatives, can allow resolution of the relevant anatomic landmark locations thereof in many cases. The inventors herein have also determined that the objectivity enabled by the methodology herein can allow even small differences in body part or body area shape or contour to be identified over imaging events taken over a period of time. This can be a very useful benefit in the context of functional garments, such as to be able to see whether a body part or body area of interest is experiencing a change that is relevant to the health or function thereof. For example, for a person who is actually or potentially symptomatic of lymphedema, the ability to measure small changes in a body part or body area over time can allow the disease cascade process to be better managed, such as by modifying a compression therapy prescription for a person as a result of the measured changes. A collection of information for a plurality of persons can also be used to generate improvements in treatment and disease management, as discussed in more detail hereinafter.

Body regions can be analyzed in relation to the fit requirements of the garment and the anthropometric shape characteristics of the subject in order to generate anatomic landmark location identifications specific to fitting the particular garment. Several analysis and calculation techniques can be used simultaneously or sequentially as appropriate in context based upon the body part or body area shape characteristics of the subject. The process incorporates a hierarchy of analysis techniques that increase in complexity until a landmark location can be confidently identified for an individual. The hierarchy of analysis techniques for garment landmark location identification can be a unique compilation of calculations dictated by the specific fit requirements and landmark location identifications for the particular garment. The compilation of the hierarchy of analysis techniques for the garment identification can further be informed by a priori knowledge of the particular garment or an assessment of the garment characteristics.

In addition to analysis of the contour of the body part or body area either directly or as the first derivatives of a plurality of circumferences along the length thereof, other processing methods for the body part or body area 3D reconstruction can be useful. For some persons, the surface contour profiles of a plurality of locations on the body part or body area can be analyzed at one or more locations on the body part or body area, for example, the medial, lateral, anterior, and posterior at a body part or body area location and compared to known anatomic landmark locations identified from a collection of body part or body area information generated from previous measurement and functional garment fitting events. In other implementations, the cross-sectional shape, cross-sectional area, and the volume of a body part or body area 3D reconstruction can also be calculated and mapped along the length of the limb, which serves to further characterize the shape and geometry of the limb, which is especially helpful in identifying landmark locations for subjects with unusual geometry and/or complex morphology. As an example, volumetric analysis of the lower leg of a severe lymphedema patient may be needed to help identify the proper placement of the proximal boundary of a knee-high or thigh-high garment in cases in which the morphology is sufficiently complex that surface-based analysis techniques would not lead to adequate landmark location identification. Position and geometric ratios can also be used to help derive an anatomic landmark location, especially when compared against a collection of a priori garment fit information. For example, in some persons, the gluteal fold will not be visibly present in images if a person is very thin. However, the gluteal fold can be approximated by use of information about the individual (e.g., height) in comparison with the position of other known landmarks and a priori information generated from a plurality of persons (e.g., library information derived from other imaged persons who had more pronounced gluteal fold regions).

In further implementations, the at least two anatomic landmark locations can be generated for an arm 3D reconstruction for a person. In illustrative examples, anatomic landmark locations can be identified for the wrist and elbow when the subject functional garment is a therapeutic/medical compression lower arm sleeve, or for the wrist, elbow, and top of upper arm, when the subject functional garment is a full arm sleeve. At least one method can be selected for the processing of the person's arm 3D reconstruction, where the method is selected to generate an anatomic landmark location identification having a high degree of confidence. In each of these example functional garments, the wrist anatomic landmark location can be derived from the smallest circumference proximal to the hand as found in the arm 3D reconstruction. The elbow anatomic landmark location can be derived from the elbow crease curvature found for the arm 3D reconstruction, and the top of the upper arm can be derived from the axilla curvature. The mid-forearm can be derived from the anterior contour derivative and the mid-upper arm can be derived from the largest contour derivative above the elbow and below the top of the upper arm. Identification of the various anatomic landmark locations from the arm 3D reconstruction can be generated from a priori information. Volume and/or geometric information can also be used.

Yet further, at least two anatomic landmark locations for a body part or body area that is the first person's trunk area or region can be identified as hips, waist, and chest using the processing methodology herein. In an example identification, the hips can be derived from a 3D trunk area reconstruction as the largest circumference above an upper leg boundary, the waist as the smallest circumference above the hip anatomic landmark location, and the chest as the circumference that is in-line with identified arm pit regions. Anatomic landmark locations relevant to a functional garment for fitting on the trunk area of the first person can be identified by analysis of the processed 3D reconstruction of the trunk in conjunction with a priori information for other persons that is present in a collection of garment fit information.

From the identification of the body part or body area anatomic landmark locations from the 3D reconstruction of a body part or body area, regional body part or body area anatomic landmark locations can be generated as follows:

Foot/heel—below ankle
Lower leg—ankle to knee
Upper leg—knee to top of thigh
Lower trunk—top of thigh to waist
Upper trunk—waist to chest
Hand—distal finger(s) to wrist
Forearm—wrist to elbow
Upper arm—elbow to top of arm In significant implementations, the outer circumferences derived from the 3D reconstructions, the identified anatomic landmark locations and the other relevant garment fit measurements that are derived therefrom are substantially identical to the measurements of the corresponding body part or body area measurement for the subject patient in real life, at least because the body part or body area 3D reconstructions are associated with accurate mathematical information. For example, when the processing of a first leg 3D reconstruction returns an outer diameter measurement of a patient's ankle as being about 8 inches, measurement of that patient's ankle will also be about 8 inches when measured by a trained clinician using the tape measurement method. The location of the ankle as an identified anatomic landmark on the patient's leg as derived from the 3D reconstruction and as identified by the trained clinician palpating the patient's leg in real life will also be substantially identical. Still further, the derived outer circumferences, anatomic landmark locations on the subject body part or body area, distances between anatomic landmarks on the subject body part or body area, and body part or body area lengths will be within about 5% or within about 2% or within about 1% of the real-life body part or body area measurements as taken by a trained clinician using the tape measurement method. Moreover, the anthropometric measurements obtained for a first person in a first measurement event and in a second measurement event will include only differences (if any) that are associated with changes in the person's subject body part or body area occurring between the measurement events, and therefore will not be an artifact of the measurement technique.

As would be appreciated, for anthropometric measurements including one or more anatomic landmark locations generated for an individual that are derived from a body part or body area 3D reconstruction to be "substantially identical" to the measurements obtained for that same individual in real life as measured by a trained clinician, the relevant anatomic landmark locations for that person must be accurately identified by the clinician. While this might not be the case in real-life measurements taken by a clinician for the reasons discussed previously, for the purposes of accuracy of the anthropometric measurements including one or more anatomic landmark locations derived herein vis a vis the real-life measurements of a subject body part or body area, it is assumed that any real-life measurements will be "ideal."

The methodology herein is configured to allow identification of the relevant anatomic landmark locations directly from a body part or body area 3D reconstruction as generated from digital images obtained by an imaging method. The anthropometric measurements including one or more anatomic landmark locations can be generated substantially without human supervision. In other implementations, anatomic landmark identification from a body part or body area 3D reconstruction can be assisted by a human supervisor via review of the body part or body area 3D reconstruction, optionally with suggestions of anatomic landmark locations generated by the computer for selection by a human reviewer. For example, analysis of the body part or body area 3D reconstruction by the computer can generate a proposed or suggested automatic identification of at least two anatomic landmark locations for a patient in need of fitting with a compression garment and the human supervisor (or "user") can confirm or modify those automatic landmark location identifications. A workflow can be provided to the user to assist in her processing of the suggestions.

A confidence level can be provided for the automated anatomic landmark location identification, with a low confidence determination being elevated to a human reviewer for review, in some implementations. The methodology can further include the generation of one or more confidence levels associated with the generated anatomic landmark location information. For example, a confidence level of about 0.90, or 0.95, or 0.99 can be generated for each identified anatomic landmark location. If the identified anatomic landmark location is returned with a confidence level that is less than a selected level, the generated result can be flagged for review by a human reviewer. In some implementations, an identified anatomic landmark location identification can be validated against a human-generated anatomic landmark identification or another method (e.g., medical imaging).

As would be appreciated, human validation can improve the confidence in the validity of the information that is included in a collection of anthropometric and functional garment fitting events that is deployable for use. In further implementations, an automated landmark location detection can be presented to a user from time to time independently of a generated confidence level. The need for human validation may become less necessary as more body part or body area anthropometric measurements and associated information is developed and associated feature sets and libraries are more robust; however, it can be useful to present at least some anatomic landmark location identification to a human for validation from time to time.

The plurality of digital images from which the functional garment fitting information is derived can be generated in a first location for a first patient imaging event where a trained fitter (e.g., a compression garment measurement clinician) may not be present. It follows that the present disclosure can enhance access of individuals to more accurate functional garment fitting operations. In some implementations, the digital images from which the body part or body area 3D reconstructions can be generated at a first location according to instructions provided to a user. Image acquisition instructions can better ensure that the digital images generated for the wearer will comprise a sufficient amount of wearer body part or body area information from which accurate anthropometric measurements including one or more anatomic landmark locations can be obtained.

Figure 5A:
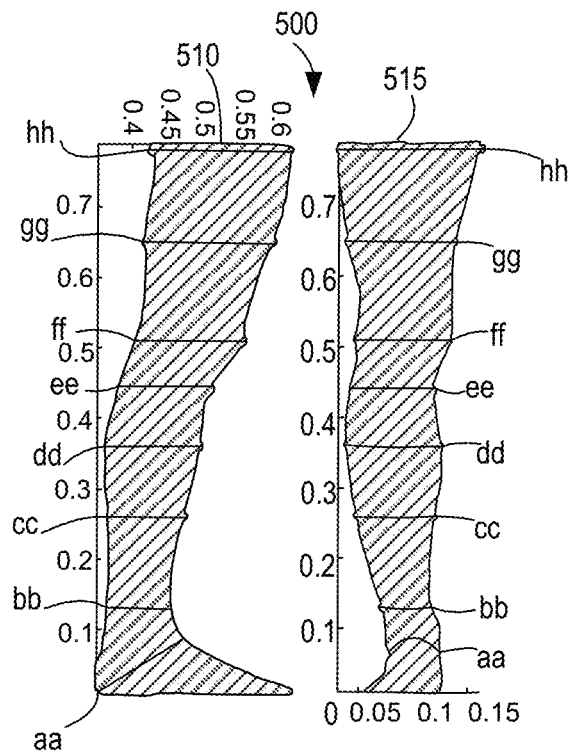
FIGS. 5A and 5B illustrate examples of anatomic landmark locations for legs, in accordance with various embodiments of the present disclosure.
Figure 5B:
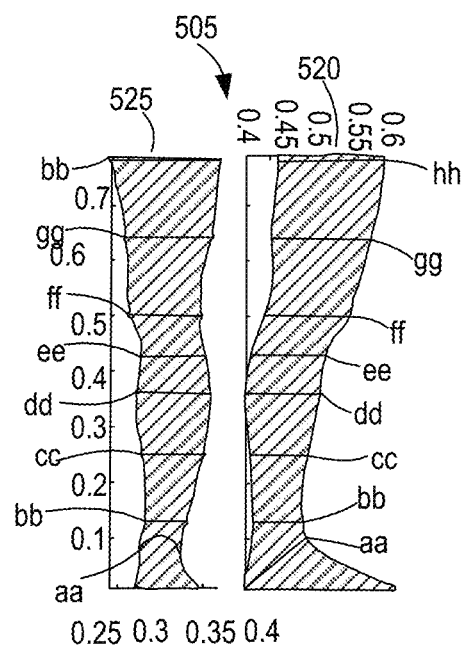

In a non-limiting example for a leg, anatomic landmark locations can be generated are illustrated in FIGS. 5A and 5B for the various identified anatomic landmarks relevant to fitting with a leg compression garment for leg view pair 500 having leg views 510 and 515, and leg view pair 505 having leg views 525 and 520. Lengths between a first and a second identified anatomic landmark location can be generated for use in functional garment fit information. At least some of the following leg anatomic landmark locations can be derivable from a leg 3D reconstruction:

i. a location proximate to a heel bottom and a bottom of an ankle (aa);
  ii. a location proximate to the ankle (bb);
  iii. a location proximate to ½ of a distance from the area proximate to the heel bottom and a location proximate to a popliteal region, i.e., the lower calf (cc);
  iv. a location proximate to ¾ of a distance from the area proximate to the ankle and the location proximate to the popliteal region, i.e., the mid-point of the calf (dd);
  v. a location proximate to the popliteal region (ee);
  vi. a location proximate to the knee region (ff);
  vii. a location proximate to ½ of a distance from the location proximate to the knee region and a location proximate to a gluteal region, i.e., the mid-thigh (gg); and
  viii. a location proximate to the gluteal region (hh).

Although not illustrated, various arm anatomic landmark locations can be identified from a 3D reconstruction as follows:

i. a location proximate to the palm at a base of the thumb; or
  ii. a location proximate to the wrist region;
  iii. a location proximate to ½ of the distance from the area proximate to the wrist and an area proximate to an elbow region i.e., the midpoint of the forearm;
  iv. a location proximate to the elbow region;

v. a location proximate to ½ of the distance from the location proximate to the elbow region and the area proximate to an armpit region, i.e., the midpoint of the upper arm; and vi. the area proximate to the axilla region.

Anatomic landmark locations on a trunk area can also be identified from a 3D reconstruction using the methodology herein where the relevant landmarks are appropriate in the context of the subject functional garment. For example, for swimsuits, the various anatomic landmark locations will be a function of the intended action imparted to the swimmer by the engineered components of the garment. Such locations will vary according to the category of garment and any specific garment falling within the category.

Figure 6:
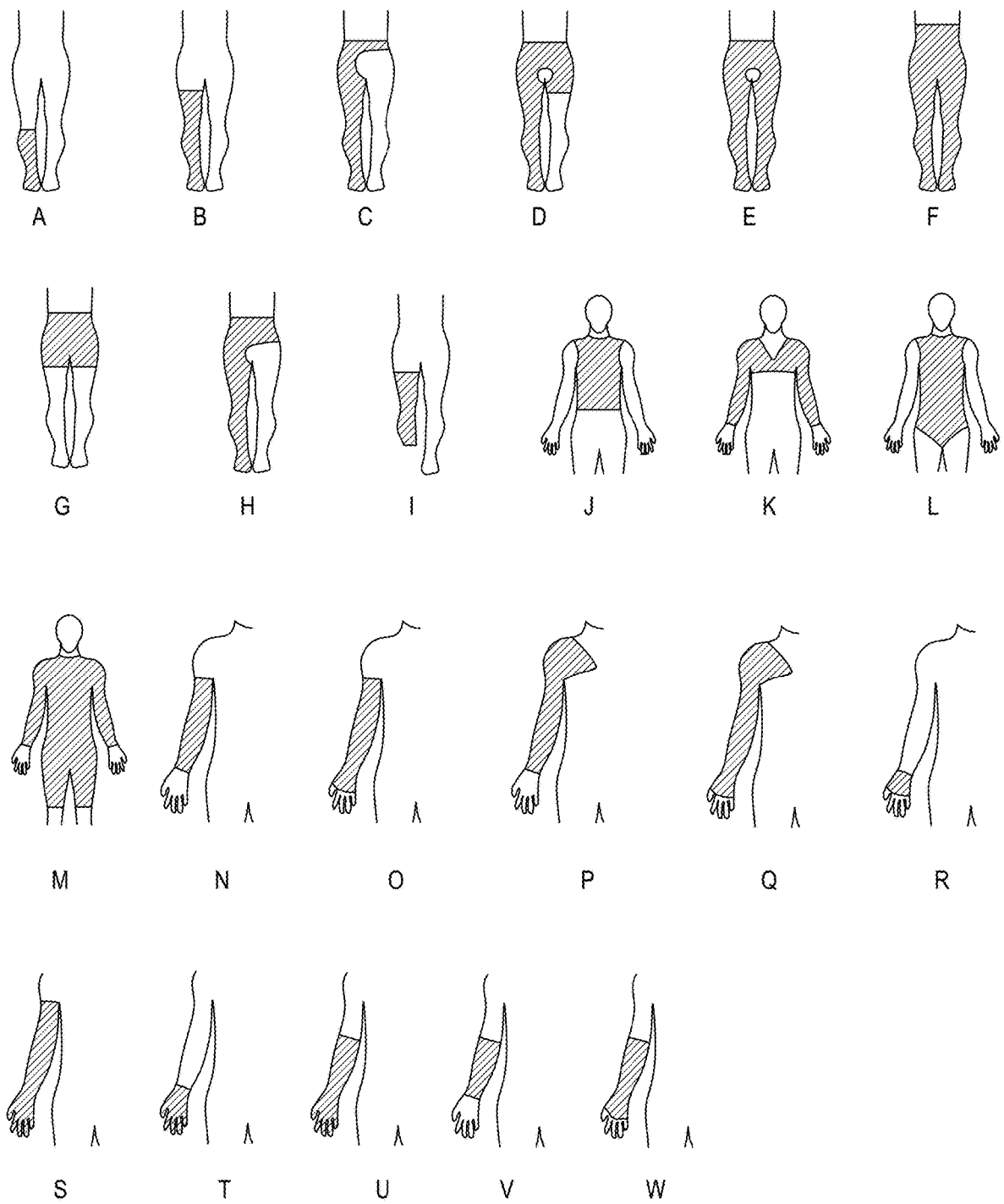
FIG. 6 illustrates examples of compression garments for various body areas, in accordance with various embodiments of the present disclosure.

For medical/therapeutic compression garment fitting, the relevant anatomic landmark locations can be associated with the areas that are associated with each of the compression garments illustrated in FIG. 6. A compression garment that is in the form of stockings can include all anatomic leg landmark locations plus anatomic landmark locations associated with the crotch and abdominal areas, for example, the pubic bone, the hip bones, and the waist, such as for D, E, and F. The outer circumference of a woman's bust as a first anatomic landmark location and the outer circumference of a waist as a second anatomic landmark location, and the distance of each of these landmark locations from each other on a 3D reconstruction of a patient trunk can be of interest in the fitting of a compression garment that is configured as a shirt, such as by J, L, and M.

In further implementations, functional garment selections can be facilitated therefrom using information provided by the manufacturers of such garments. Since functional garments are engineered to impart one or more effects to a person when worn properly, information associated with such engineering will be incorporated as standardized features or characteristics. For example, medical/therapeutic compression garment manufacturers provide fit information that is relevant to each company's product lines and individual garment specifications.

Medical/therapeutic compression garment manufacturers provide anatomic landmark location information for deployment by clinicians in an in-person compression garment fitting scenario. Using the tape measurement method, the clinician can be instructed that an individual's ankle should be measured just above the malleolus, which is typically located between about 6 to about 12 centimeters above the floor. While not always accurate and/or precise, a clinician who is generating measurements for a body part or body area for the purpose of fitting compression garments can use her expertise and subjective judgment to identify a specific location on an individual's ankle within the designated range of locations defined by the manufacturer. Of course, such expertise and associated subjective judgment is not available when a computer, without more, is configured to process digital imagery for the purpose of identifying anatomic landmark locations relevant to the fitting of medical/therapeutic compression garments therefrom. The methodology herein imparts the ability to generate anthropometric measurements including one or more anatomic landmark locations for use in generating compression garment fit instructions that meet or exceed the degree of accuracy available from in-person measurements by trained clinicians and/or compression garment fitters.

A priori body part length information can be appropriately incorporated into the anatomic landmark location identification from a body part or body area 3D reconstruction. For example, a lower leg length (e.g., from bottom of foot to bottom of knee region) that is determined to be 40 centimeters will provide area region for the ankle that is from about 8 to about 15 centimeters from the floor in most people as such landmark location information is provided by compression garment manufacturer fit instruction information, among other sources. The popliteal area will be located from about 5 to about 10 centimeters from the midpoint of the knee crease in most people or, from another direction, between about 30 to about 45 centimeters from the floor as the range of values for a lower leg length in a population of persons. Thus, when searching for these respective anatomic landmark locations in a leg 3D reconstruction derived from the patient's digital imagery, the system can be configured to focus on these areas so as to identify the location within this range along the leg. By reducing the search space on the subject leg 3D reconstruction, anatomic landmark location identification can be enhanced. Moreover, the collection of anatomic landmark identifications generated from a population of patients that are known to be accurate can enrich existing information to enrich the libraries of information used in the detection of landmarks in other persons. Over time it is expected that the system will be able to identify the anatomic landmark locations in persons with varied body part or body areas types with higher confidences.

Referring to FIGS. 5A and 5B, because compression values for a patient are selected to provide compression therapy to improve lymph or vascular flow in the lower leg of a person, at least one anatomic landmark location for the application of compression therapy can be at a lower or distal location on the patient body part can be derived from the 3D reconstruction of the first person's lower leg. This lower or distal location can be the ankle location (i.e., bb) or, for some patients, the location that spans the bottom of the foot to the bottom of the ankle location (i.e., aa). For leg compression therapy, compression garment fit information can be generated so that the lower portion of the compression garment (e.g., aa or bb) will suitably apply a compression value that is from about 20 mm Hg to about 50 mm Hg as applied by the compression garment via the elasticity incorporated therein when the garment is worn for the patient.

While the distal or lower area of a lower leg compression garment generates the majority of the function of affecting the flow of fluid in the person's lymph system, the top of a medical/therapeutic compression garment configured for a lower leg of a person garment needs to be placed in a region where it will not slip down or ride up. The unique surface contour of an individual patient can determine the ideal location to place the upper boundary of the garment to ensure it remains in place to the maximum extent possible and ensuring that the garment remains in place as much as possible ensures that the pressure of the garment is applied as correctly as possible. The popliteal landmark (ee), therefore, may be less associated with a functional application of compression to the person's underlying lymph systems and more related to the local surface contour that will allow the upper band of the compression garment to remain fixed in place. Identifying the popliteal landmark (and thus the upper boundary of a lower leg compression garment) too low may cause the garment to fall down the calf (similar to the slip of dress socks during the course of a day) and placing the landmark too high will cause it to bunch up in the flexion of the knee. As such, the popliteal is a relevant anatomic landmark for the fitting of this type of functional garment in that without appropriate identification thereof will likely reduce the effectiveness of the compression garment for the person.

Also, the garment should not be so loose as to ameliorate the compressive force applied at the ankle, nor should it be so tight as to pinch or bind when worn. This means that the function of this medical/therapeutic compression garment can also be affected by the fit of the garment along the person's leg, which will be associated with the person's unique lower leg size, shape, and contour. Using the lower leg medical/therapeutic compression garment as an example, in some implementations, the anthropometric measurements including one or more anatomic landmark locations can include the identification of other locations on the person's leg from the 3D leg reconstruction, such as the mid-calf (i.e., the widest area on the calf (dd)), or any other location selected as relevant in context. The methodology herein provides a notable improvement over prior art garment fitting techniques that rely, at least in part, on the subjective identification of anatomic landmark locations, whether by palpitation or from digital imagery. That is, the present disclosure enables landmark location identification to be derived automatically from digital imagery of a body part or body area through application of methodology that creates a standardized processing methodology that is consistent amongst a plurality of individuals. By standardizing anatomic landmark location determination for a plurality of individuals, garments can be fitted to an anatomic landmark location as present on a single person. This is an improvement over manual anatomic landmark location techniques at least because, for example, the true location of the widest calf can be generated for that person using the objective visualization techniques provided by automated processing of the digital images of the leg. This objective methodology thus informs the specific anatomic landmark location—here the lower leg—to better ensure the compression garment not only is correctly fit, but also will generate a prescribed or indicated amount of compression therapy when the subject compression garment is worn by a person in need of such compression therapy.

Functional garment fit when the garment is worn by a person can be enhanced with the addition of body part or body area shape or contour information that is generated from a plurality of outer circumferences along the length thereof. Thus, it can be useful to include a plurality of outer circumferences for the subject body part or body area in the garment fit information in addition to the outer circumference generated for each of the at least two anatomic landmark locations. Using the medical/therapeutic compression garment example, the body part length information can be used to select an appropriately sized prefabricated compression garment for the patient, such as short, regular, long, and extra-long, or the like. While a prefabricated garment may not be exactly matched to the specific shape or contour of an individual patient, the shape or contour of her body part or body area can be useful to compare with the shape of a prefabricated compression garment to confirm that an identified prefabricated compression garment will exhibit a good fit and thus will provide the prescribed or indicated amount of compression therapy when worn by the patient. Such plurality of outer circumferences can also provide notable benefits for the fabrication of custom compression garments, as would be appreciated.

An exact or nearly exact length of each portion of the body part or body area can be incorporated into functional garment fit information. Length can be measured as straight-line length and/or contoured length along the surface. Lengths can also be measured along several different surfaces as appropriate (e.g. medial, lateral, posterior, etc.)

When the functional garment is a medical/therapeutic compression garment, tensioned circumference can also be relevant to the accurate fitting thereof. Methods of generating tensioned circumference are disclosed in U.S. Pat. No. 10,842,680 (the "'680 Patent"), for example, the disclosure of which is incorporated herein in its entirety by this reference. To summarize the tensioned circumference generation method, some patients can have a degree of body part or body area distortion that can affect the amount of compression applied from the compression garment to the body part or body area, as discussed further herein. Such body part or body area distortion can be an indication of a patient being symptomatic for edema/lymphedema and/or due to excess adipose tissue being present. Such limb distortion will typically result in the body part or body area presenting with more compressible tissue when a tape measurement method of fitting compression garments is utilized. Thus, for some patient body parts in need of compression therapy, the amount of pressure intended to be applied by the compression garment is not fully transmitted to the patient's lymph or vascular system. In short, such compressible tissue may "absorb" or dissipate (e.g., will be less likely to transfer an applied force) at least some of the applied compression, and the applied compression may not effectively act on the underlying lymph or vascular system. The methodology disclosed in the '680 Patent details how such tensioned circumferences can be derived and, to the extent necessary, that disclosure is incorporated herein. In some implementations, the tensioned circumferences can be generated at each of the generated anatomic landmark locations. Further, one or more tensioned circumferences can be generated along a length of a body part or body area.

To generate appropriate medical/therapeutic compression garment fit information for other locations along the body part or body, additional tissue compressibility and outer circumference information can be derived. For example, tissue compressibility and outer circumference information can be generated for at least two additional leg locations, where a topmost leg location on which the compression garment is fit is one of the additional body part locations. Referring to FIGS. 5A and 5B, a medical/therapeutic compression garment in the form of a sock may only be worn up to the upper calf location, which is the location that is approximately ¾ of the distance between the ankle location (bb) and the popliteal (ee) on the patient's leg. A full leg compression garment may extend from the location below the ankle (aa) to the groin region (hh), with other body part locations in between those locations potentially being relevant to the compression garment fit information such that tissue compressibility and outer circumference information is generated for at least one location in between the first and second ends of the compression garment as it is to be worn on the body part of the patient. As would be appreciated, at least 3 sets of tissue compressibility and outer circumference information, which will include at least two anatomic landmark locations at each of a distal and proximate location, can allow the generation of both outer circumference and tissue compressibility characterizations for each body part. In some implementations, such information can be generated for 3 or more locations on the body part. Compression garment fit information used in the fabrication of custom garments can include more circumference measurements, whereas compression garment fit information for use with prefabricated compression garments may not benefit from more than about 3 or 4 outer circumference values.

Figure 20A:
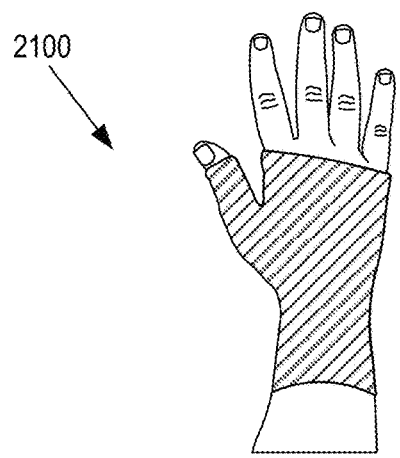
FIGS. 20A, 20B and 20C illustrate examples of a hand gauntlet, glove and arm sleeve gauntlet, in accordance with various embodiments of the present disclosure.
Figure 20B:
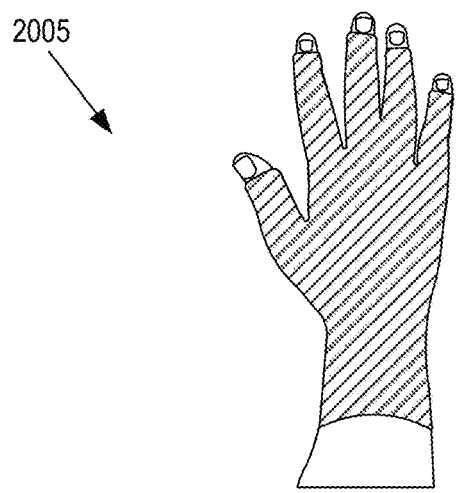

For an ankle to groin medical/therapeutic compression garment, additional anatomic landmark locations as incorporated in compression garment fit instructions can be used to identify the relevant anatomic landmarks from the leg 3D reconstruction within the defined areas developed from this standardized compression garment fit instructions as set out by the various compression garment manufacturers. Similar search area frameworks can be used for other body part or body areas and associated compression garments (e.g. partial arm sleeves, full arm sleeves, gloves, pantyhose, socks, shirts). Examples of compression garments that can be fitted with the methodology of the present disclosure are shown in FIG. 6 and in FIG. 20.

The disclosure further provides a method of at least partially automatically identifying at least one compression value indicated for a patient for a medical/therapeutic compression garment to be worn by the patient in need of compression therapy where a defined, prescribed, or selected, compression level is applied to the patient when the garment is worn on the subject body part or body area. The compression value prescribed or indicated for an individual patient can be derived from a collection of compression garment fit and usage information obtained by the imaging and treatment of a plurality/population of patients.

For example, existing medical/therapeutic compression garment fit instructions provide that a person with a disproportionate body part or body area (e.g., the individual pictured in FIG. 3A) may be better treated by custom compression garment, as opposed to a prefabricated one. Thus, the system can be configured to analyze the generated 3D reconstruction of the subject body part or body area to determine whether one or more disproportionate areas are present. An example of a "disproportionate area" would be a knob, lobe, or fold on the body part or body area. A "disproportionate area" can also be an area having a morphology that substantially differs from an average body part or body area shape. In this regard, some or all of the body part or body area 3D reconstruction data can be analyzed to determine a distribution of shapes for a body part or body area. The body part or body area of interest can be considered to have a "complex morphology" if that shape is determined to fall outside of the normal distribution, for example below the 20th percentile and above the 80th percentile. Alternatively, the subject body part or body area can be analyzed to generate a probability that the shape thereof is likely to have a complex morphology. If the subject body part or body area is determined to comprise one or more disproportionate areas and/or a complex morphology, the system can automatically default to a custom compression garment as the appropriate selection for that patient. Information needed to generate custom compression garments can be automatically generated for inclusion in compression garment fabrication instructions.

On the other hand, if the system determines that the subject body part or body area does not include any disproportionate areas or complex morphology, the system can be configured to perform an analysis to determine whether a prefabricated medical/therapeutic compression garment is indicated for the patient and, if so, what garment (size/dimensions, manufacturer) can be appropriate. In this regard, the system can be configured to determine whether the subject patient falls within the size, compression values, etc. parameters for a collection of prefabricated compression garment. For example, the system can also analyze various aspects of the body part or body area 3D reconstruction to identify features unique to that patient that may indicate one type of compression garment over another or one manufacturer over another. The patient may have a longer than average limb length as indicated by the collection of body part or body area length information, for example, a leg portion might be found to have an overall length (e.g., ankle to crotch) that is longer/shorter than average or a portion that is longer than average (bottom of foot to knee), which can indicate that a custom compression garment is a better selection for that person to ensure a good fit. Compression garment fabrication instructions can then be generated for that patient.

To understand the process of medical/therapeutic compression garment fitting for a patient in need thereof according to the present disclosure, consider the following illustrative example. A 65-year-old female patient ("Patient A") is being fit for a medical/therapeutic compression garment for the treatment of lower leg lymphedema, where the fitting is via digital imaging of her leg and processing of such images to generate a 3D reconstruction of her lower leg where the 3D reconstruction from which the anthropometric measurements including one or more anatomic landmark locations are generated is mathematically accurate vis a vis her corresponding real-life leg. As shown, the 3D reconstruction is generated as a shape description as shown in the '581 and '438 Patents, however, any other suitable 3D reconstruction generation method can be used to generate the anthropometric measurements used in the compression garment fit instructions. From this 3D reconstruction for the leg (that has been segmented or isolated from a larger 3D body reconstruction in this example), a plurality of leg outer circumferences and, optionally, tension circumferences for one or more leg circumferences can be generated, as well as length information for the lower leg. At least two anatomic landmark locations that are relevant to the fitting of the subject compression garment, here the ankle and popliteal landmarks, can be automatically identified and located on the 3D reconstruction—and therefore Patient A's actual leg—using the methodology herein. As discussed herein, the outer circumference of Patient A's ankle can be derived from the leg 3D reconstruction. Tissue compressibility information for her ankle etc. can also be generated. Optionally, a human reviewer can be prompted to validate or confirm the correct anatomic landmark location identification.

Body part or body area shape or contour information to assist in generating compression garment fit information for Patient A can also be generated, especially if she is indicated for a custom compression garment. The system can be configured to automatically generate compression values to be applied to Patient A when she wears the compression garment on her lower leg, or the compression values can be supplied by a health care provider. If the latter, the system can validate or confirm the appropriateness of the supplied values against her health and other information available to better ensure that the compression garment fit information is generated using the broadest scope of information available. Optional human validation can also be provided.

Instructions for the selection of an appropriate prefabricated compression garment or how to start the fabrication process of a customized compression garment can also be provided. If she is indicated for a prefabricated compression garment Patient A or her healthcare provider can be directed to an online order portal where the selection or ordering instructions can be provided to allow a more seamless garment procurement process. To this end, she can be directly linked with an online ordering portal that selects for her a prefabricated knee-high compression garment from Brand X and with a SKU of Model/Sizing Y/Z. Such online ordering portal can be integrated with insurance or other payment systems. If the system determines that Patient A is indicated for a custom compression garment, the generated compression garment fit instructions can be automatically provided to a compression garment manufacturer via an online ordering portal.

To further refine the anatomic landmark location search, information about an overall height of the person, BMI, etc. can be incorporated in the body part or body area 3D reconstruction processing. To this end, it can be expected that the fitting of functional garments for a specific wearer or group of wearers can be enhanced when anatomic landmark location information derived from functional garment fit instructions generated from historical information can be enriched by the purposeful collection of information associated with a person or group of persons who in need of fitting therewith. The inventors anticipate that variables that are not currently known to be relevant to the fitting of a functional garment for a person can be identified through evaluation of a broad collection of information associated with an individual and/or a population of individuals.

In accordance with the methodology herein, the generated functional garment fit instructions can be generated for each individual, and can be a function of demographic and/or personal health information available for an individual patient or a group of patients, which could include but is not limited to:

Age;
Weight;
Sex;
BMI (body mass index);
Activity level;
Medical history or diagnosed conditions; and/or
Socio-economic data.

Functional garment fit instructions for an individual can also be generated by comparing an individual's anthropometric measurements including one or more anatomic landmark locations and other relevant information with anthropometric measurements and other information generated from a population of individuals for which garment fit information was previously generated. Information associated with the actual fit of the subject functional garment when each individual was wearing the garment can also be included in the fitting of the functional garment for a subsequently performed fit instruction generation event.

Additional information relevant to the fitting and wearing of functional garments can also be used to generate garment fit information, for example, human factors information can be useful in some implementations. In the case of medical/therapeutic compression garments medical research and existing knowledge can provide useful information that can seed information used to process the generated 3D body part or body area reconstructions, such as by generating a prediction or recommendation for the appropriate compression values to apply to various patients in context.

In this regard, information about a health condition of a person or a collection of persons potentially in need of fitting with a functional garment can be useful. As used herein, "health condition" is used broadly to include medical information that may be included in a personal health record, such as medical condition or diagnosis information that would be held by a doctor, hospital, or the like. "Health condition" can also comprise information that may be associated with medical condition or diagnosis information, such as height, weight, BMI, self-reported conditions, or the like. Such information can enrich generated functional garment fitting, such as medical/therapeutic compression garment fit information, that is generated from the anthropometric measurements for an individual using the automated methodology herein. While it may be necessary for a clinician to confirm or validate the identified or suggested medical/therapeutic compression garment fit information at or near the early development stage of the system, as more information is generated for a large population of patients, the collection of information deployable in machine learning processes will become enriched to improve the accuracy of the system. In some implementations, the garment fit information can be generated substantially automatically using the processes herein. To ensure continued accuracy of the anthropometric measurements including one or more anatomic landmark locations and associated functional garment fit information, however, it can be beneficial for a clinician or other supervisor to review the generated results from time to time.

A person may be indicated from information derivable from the 3D leg reconstruction and/or from a health care provider's diagnosis as presenting with an early stage (e.g., Stage 1) lymphedema. Such a presentation could allow the person to be indicated for a prefabricated compression garment if her body part or body area does not include disproportionate areas and/or is not unusually small or large. In this case, the system can automatically identify the patient as suitably being fit with a prefabricated medical/therapeutic compression garment, unless there is another reason to indicate or prescribe a custom compression garment for the patient, such as if there is an optional selection or over-ride that allows a different selection to be made for the individual. For example, the patient may have a specific fashion-related specification (e.g., color, seamless). Since many fashion-related specifications can only be accommodated in custom compression garments, the system can be configured to automatically default to custom compression garment fabrication instruction generation. Such patient-specific selections can be included in a query or workflow where patient preferences can be incorporated in the selection of a compression garment type.

In further implementations, the consistency of the anthropometric measurements including one or more anatomic landmark locations obtainable from patients according to the disclosure herein can allow generated body part or body area anthropometric measurements to be used to create training sets deployable in machine learning processes. Such collected information can, in turn, enhance the generation of subsequent anthropometric measurements including one or more anatomic landmark locations and associated functional garment fit operations. The accuracy of the objectively generated body part or body area anthropometric measurements including one or more anatomic landmark locations for each individual obtainable from the methodology herein can be used collectively to generate measurements for other individuals and, in turn, such newly created anthropometric measurements including one or more anatomic landmark locations can be added to the collected information for subsequent measurement generation. As such, the baseline accuracy enabled by the methodology herein provides notable benefits over prior art measurement techniques.

In this regard, collected information that lacks precision—whether or not it is accurate in context—will cause any information derived deployment of systems that use such collected information to also lack precision. Thus, any information derived from such faulty collected information will not be dependable, which, of course, is a problem in at least the context of medical or therapeutic applications. Also, since the subsequently imprecise information that is added to the collected information will generate a priori information that is not operational to generate correct results, any information generated from collected information that is wrong the first order will become even more imprecise over time to result in a continuously magnifying "garbage in/garbage out" scenario. The methodology herein therefore presents for the first time a way to generate useful anthropometric measurements including one or more anatomic landmark locations and functional garment fitting information for one or more individuals from 3D reconstructions of body parts or body areas that are derived from digital imagery because the information that is used to seed and enhance feature sets used in machine learning systems is accurate in the first order. That is, the anthropometric measurements including one or more anatomic landmark locations for one or more individuals are accurate for each individual over a plurality of imaging events which, in turn, enables the generation of a robust and useful collection of anthropometric measurements including one or more anatomic landmark locations and functional garment fitting information deployable for various uses as discussed herein.

Such generated anthropometric measurement information that includes relevant anatomic landmark location information can be used in the development of functional garment fit information that incorporates insights generated from a population/plurality of persons who have undergone at least one digital imaging event associated with the generation of compression garment fit information. Yet further, mathematically accurate anthropometric measurements including one or more anatomic landmark locations for body part or body areas for each of a plurality of persons can be generated to validate or modify assumptions about patient anthropometry, patient physiology, existing functional garment fit information, medical diagnosis or physical condition, and treatment effects, among other things. It is expected that by generation of a robust collection of a priori patient data, a "virtuous cycle" of cause-and-effect data can be generated using the methodology herein.

The methodology herein also has utility in the emerging area of "digital twins" as applied in a human factor and/or medical environment. As originally applied, a digital twin is the virtual representation of a physical object or system across its lifecycle. A generated digital twin uses real-time data or other sources to enable learning, reasoning, and dynamic recalibration to allow improved decision making. In the context of human factors and/or medical analysis and improvements associated with functional garment engineering and performance evaluation, the concept of "digital twin" can be applied to any person who is of interest for the evaluation of performance resulting from or associated with the wearing of a functional garment. For example, a digital twin of a patient being treated with compression therapy for lymphedema can be evaluated to provide prescriptions and direction for her to manage her own health outside of the clinical setting. A digital twin of an individual fire fighter can be evaluated to determine how that person may perform under various scenarios while wearing a protective/supportive garment engineered for her use while fighting fires. A digital twin of a swimmer can be evaluated to determine how an engineered swimsuit may affect her performance under various scenarios. As would be appreciated, information associated with hypothetical conditions that may affect the functional garment wearer's respective performance are useful in generating these simulations. Information derivable therefrom can further be incorporated into collected information deployable in subsequent examination events. Assumptions generated from the simulations can be tested, thereby allowing further improvements.

As applied in the present methodology, the functional garment wearer digital twin can provide a framework to map current wearer observations into a collection of a priori information useful to generate a predictive framework that combines inductive and deductive reasoning, as would be deployed by a person experienced in human factors analysis. Thus, a wearer digital twin does not just allow prediction generation, the concept more closely approaches the way a human will address a problem. Moreover, functional garment wearer digital twins can even be argued to be an improvement over many humans in the context of human factors analysis because a computer can handle many more pieces of data simultaneously than a human can.

When applied to the medical/therapeutic compression garment context, a patient digital twin can be defined as a set of virtual information constructs that integrates body shape characteristics (e.g., swelling, differential limb shapes) derivable from a generated body part or body area 3D reconstructions combined with other relevant physical information for the patient (whole anatomy, holistic view, skeletal system, nervous system, vascular system, etc.). In certain examples, the patient digital twin can be a reference digital twin (e.g., a digital twin referenced against a "healthy" or "normal" lymph system etc.) or a reference patient digital twin (e.g., a patient of a similar age, diagnosis, BMI, ethnicity, etc.). The reference patient digital twin can represent a prototypical or ideal model of the patient or of a particular type/category of patient, while one or more reference patient digital twins can represent particular patient categories.

The "digital twin" concept is starting to be applied in the healthcare field to enable use of integrated patient and other relevant data during the life—or relevant life stage—for a patient. Use of a digital twin for a patient allows a health care provider and/or an automated process to view and evaluate visual data for a patient and a relevant symptomology and/or diagnosis without having to move from one or more (often unrelated or disparate) datasets to the patient and back because, as noted, a computer can simultaneously handle many disparate data streams at once. With the patient digital twin reviewable in common perspective with the actual patient, physical and virtual information can be viewed together, dynamically and in real time (or substantially real time accounting for data processing, transmission, and/or storage delay). Rather than reading a report, a healthcare practitioner can view and simulate with the patient digital twin to evaluate a condition, progression, possible treatment, etc., for the patient. In certain examples, features, conditions, trends, indicators, traits, etc., can be tagged and/or otherwise labeled in the patient digital twin to allow the practitioner to quickly and easily view designated parameters, values, trends, alerts, etc.

The functional garment wearer digital twin that is rendered from one or a collection of 3D reconstructions of body parts or body areas can also be used for comparison (e.g., to the individual functional garment wearer, to a "normal", standard, or reference functional garment wearer, set of relevant use case criteria, etc.). In certain examples, the functional garment wearer digital twin for an individual can be used to measure and visualize an ideal condition state for that wearer, a margin for error or standard deviation around that value (e.g., positive and/or negative deviation from the gold standard value, etc.), an actual value, a trend of actual values, etc. A difference between the actual value or trend of actual values and the ideal wearer physical, health, performance, or other condition (e.g., that falls outside the acceptable deviation) can be visualized as an alphanumeric value, a color indication, a pattern, etc.

Further, the patient digital twin can facilitate collaboration among family, healthcare providers, etc., for the patient. Using the digital twin, conceptualization of the patient and his/her health can be shared (e.g., according to a care plan, etc.) among multiple people including care providers, family, friends, etc. People rendering diagnosis and care do not need to be in the same location as the patient, with each other, etc., and can still view, interact with, and draw conclusions from the same digital twin, for example.

Each functional garment comprises at least one defined functionality that distinguishes one category or type from another. In addition to such functionality, each functional garment fulfills requirements common to all wearers: physiological, biomechanical, ergonomic, and psychological. There is interplay between each of these categories. For example, a correctly fitted medical/therapeutic compression garment having the correct level of compression included for a person in need thereof will affect the underlying physiology of the wearer while still allowing her to move freely and with comfort thus implicating each of physiological, biomechanical, and ergonomic requirements associated with the subject garment. When this compression garment is designed with consideration of the wearer's desire for the compression garment to be unobtrusive when worn, all four requirements will be met.

The accurate anthropometric measurements including one or more anatomic landmark locations obtainable with the methodology herein can address a significant aspect of the physiological aspects of functional garment engineering by enhancing the ability to generate a fit for the wearer where the fit is associated with one or more functions of the subject garment. A further improvement with the present methodology incorporates the collection and use of information associated with the wearer of a subject functional garment where that data can be used in conjunction with the fitting of the garment for the person. Yet further, data can be generated while the garment is being worn. The collected data can be used to generate better fitting of functional garments for an individual wearer and for a population of wearers. Such information can also be used in the design of improvements in one or more functional garments.

As an illustrative example, medical/therapeutic compression garment fitting information in use today assumes that the functionality of compression garments can be universally prescribed for all persons, irrespective of the absence of actual knowledge about the characteristics of the person's lymph system below the skin surface. That is, it is assumed that a lower leg compression garment that is fitted properly at the person's ankle and at the popliteal landmarks will effectively provide the intended compression therapy. This may not necessarily be the case if a person's physiology does not comport with the expected or "normal" lymphatic response from the proper wearing of a well-fitted compression garment configured with the prescribed or indicated amount of compression therapy. The methodology herein can allow the therapeutic effectiveness of a medical/therapeutic compression garment to be evaluated over time, for example, in a first, second, third etc. digital imaging events for that person. The information can be used to generate one or more compression garment fit instructions for that patient, as well as for use in generating fit instructions for a plurality of patients in need of fitting with medical/therapeutic compression garments.

Further in the context of the collection and deployment of wearer and other relevant information in the methodology herein, the system can be configured to suitably process structured and unstructured data. As would be appreciated, "structured data" is data that comports with a pre-defined data model and therefore can be analyzed according to rules operational with that model. Structured data conforms to a tabular format with relationships between the different rows and columns. Each field of data will be independent and thus can be accessed separately or jointly along with data from other fields. Common examples of structured data are Excel files or SQL databases. Each of these have structured rows and columns that can be readily sorted. "Unstructured data" is data that either does not have a predefined data model or is not organized in a pre-defined manner. Unstructured data has internal structure but is not structured via pre-defined data models or schema. It may be textual or non-textual, and human or machine generated. It may also be stored within a non-relational database like NoSQL. Data that is complex or heterogeneous and cannot be fit into standard fields is unstructured data. Unstructured data can be stored in a data lake, which is a storage repository where a large amount of raw data is stored in its native format. Common forms of "unstructured data" in the context of the present disclosure can include clinician notes, patient observations, socioeconomic data, GPS data, images, audio recordings, videos, etc.

Methods to process structured and unstructured data to extract useful insights about individuals generated from a variety of disparate and previously siloed data sources are evolving quickly. For example, U.S. Pat. No. 10,483,003 (the "'003 Patent"), the disclosure of which is incorporated in its entirety by this reference, discloses methodology to develop clinical insights for decision support services. Such methodology is stated to enhance patient medical treatment by enabling timely contextual patient information to be obtained. Such contextual patient information includes condition risks, risk factors and relevant clinical information that are dynamically updatable. Application of a data analysis methodology such as that in the '003 Patent along with the processing of segmented/isolated body part or body area 3D reconstructions and any accompanying data available in the collected information useable as a priori information is expected to greatly improve the knowledge base associated with the fitting and use scenarios associated with functional garment engineering.

To generate wearer data on an ongoing basis, one or more devices can be configured to collect information from a person wearing a functional garment over a plurality of times for incorporation into the collected information and/or for use in a patient digital twin environment to generate insights about a single functional garment wearer or a plurality of wearers. Such information collection can be useful to test and/or validate real time assumptions made by designers of functional garments about how users feel when wearing the garment. That is, prior to the present methodology, designers of functional garments have had no real way to assess the effectiveness and comfort of their engineering assumptions when a person was wearing the subject functional garment. The association of data collection while the functional garment is being worn is expected by the inventors herein to lead to significant improvements in the design and engineering of functional garments.

Information associated with the wearer of a functional garment can be collected while a functional garment is being worn by one or more sensors. Such sensors can be worn by the wearer to measure movement via a wearable fitness monitor (e.g., FitBit®, Apple Watch®, etc.) or sensors that can detect movement of the wearer.

In the context of medical/therapeutic compression garments, exercise is known to be important for persons diagnosed with lymphedema by increasing the flow of lymph fluid, weight maintenance, promoting flexibility, and reducing stress. While clinicians can prescribe exercise, the patient may not be able to accurately confirm compliance between clinic visits. Data collected from one or more a fitness monitor, a connected scale, a connected exercise device (e.g., elliptical machine, treadmill, exercise bicycle, etc.) can be incorporated into the patient data or in a population of patient data to assess compliance with exercise recommendations.

The robustness of the anthropometric measurements including one or more anatomic landmark locations for one or a plurality of patients in need of functional garments, such as a person in need of compression therapy, included in the collected information can be enhanced with the incorporation of other relevant (or potentially relevant data) about the person or persons who are being fitted for the subject functional garment. Such wearer information can be incorporated into the collected information and can include information that could be useful to the generation of insights about the performance of the wearer(s), for example. Wearer information can include age, gender, body mass index, medical history, work injury history, training history, etc. In the context of medical/therapeutic compression garments, wearer information can also include surgical history (e.g., number of lymph nodes removed, number of prior surgeries, etc., family information (social dynamics to indicate support structure, access to exercise locations, transportation, etc.), genetic information (e.g., ancestry), economic data/demographics, treatment information (e.g., clinician notes).

The collection of wearer information can be expected to lead to improvements in the fitting and design of functional garments by the generation of longitudinal information. Especially in the context of medical/therapeutic compression garments, information can be generated about compression therapy treatment effectiveness in a patient diagnosed as being in need of compression therapy. Further, a rich database of body part or body area anthropometric measurements and information relevant thereto for a plurality or population of disparate patients is expected to allow improvements in the ability to predict whether a patient may develop symptoms of lymphedema by comparing her body part or body area characteristics via the body part or body area 3D reconstruction thereof against a large collection of patient data—imaging and otherwise—where diagnosis and treatment information has been included as feature sets. This is expected to generate new knowledge, such as identifying or evaluating treatments or sequences of patient care actions and behaviors, and providing recommendations based on such knowledge. Moreover, treatments can be adapted for each patient or class of patients during a treatment by comparing an individual patient against a large and robust patient population data set. This can be highly relevant to lymphedema treatment protocols at least because, as noted previously, a goal is to predict the likely occurrence of the "lymphedema cascade" in a patient. The large data set enabled by the methodology herein is expected to allow the identification of critical junctures in patient care that can predict and, hopefully, prevent the "cascade" event from occurring.

In this regard, information associated with the patient after a first imaging event can be collected to enrich her diagnosis and treatment information, as well as to enhance one or more subsequent compression therapy characteristics (e.g., type of compression garment, garment fit, compression value, etc.) if the patient imaging and associated data indicated that one or more first (or previously) prescribed or indicated compression therapy characteristics did not generate the expected or intended response in the patient. For example, if the patient is found not to wear her compression garment as directed, she will not obtain the intended compression therapy. It is likely that any identified lymphedema symptoms will not be well-managed by her. Information about such non-compliance can be deployed to determine why she may not be wearing her compression garment as directed. Is it too tight? Too hot? Not aesthetically acceptable? As would be appreciated, such wearer specific queries can also be more broadly applied to other categories or types of functional garments.

Such associated patient information can be used to gain insights about the patient between visits, such as to assess sleep habits or activity level by comparison with other patient data. Predictions about the patient's current and future condition can also be generated. When incorporated in the context of a patient digital twin, the health care provider can be provided with notifications between visits if real time patient data associated with a patient digital twin indicates that intervention is needed.

In some implementations, the clinician can be notified of information for a patient in between clinic visits. For example, a notification can be generated that one or more patients are not wearing their compression garments as directed. Such notifications can be presented to the health care provider as a report or in dashboard form, to allow a collection of patients to be reviewed to allow a clinician to gain an overview of a collection of patients to improve decision-making as well as diagnosis and treatment effectiveness over time.

Still further, such information can be used to gain insights into whether the wearing of a functional garment increases or decreases the propensity of the patient to exercise or to undertake a type or intensity of exercise. A baseline activity amount can be generated for a person or a group of persons and any changes associated with the wearing of a prescribed or indicated compression garment can be generated as information. In the context of medical/therapeutic compression garments used for exercise, to date data showing that compression garment wearing during exercise generating improvements in recovery time has only been primarily anecdotal. By incorporating objective information about the effect of compression garment wearing during and after one or more exercise events in a person or for a plurality of persons, improvements in the knowledge base associated with compression garment fitting and patient use thereof can be generated.

More broadly, longitudinal data collection for a plurality of wearers of functional garments can be collected in dashboard to, for example, receive insights into whether one or more persons may need intervention to prevent injury, improve performance, etc.

As would be appreciated, any device upon which wearer personal data is collected must be configured to maintain the security of such data in use, which is within the skill of a person of skill in the art. Collections of wearer data can be anonymized according to known methods to comply with applicable privacy laws (e.g., HIPAA, GDPR, CCPA, etc.).

Information associated with the wearing of a functional garment can be collected via a device that is in communications engagement with a cloud server or a local device that is in communications engagement with a data storage system (e.g., local device, onsite server, cloud storage, etc.). For example, a fitness tracker can be in communication with a smartphone that is configured with an app can be in communications engagement with a medical/therapeutic compression garment. The app can collect information on an ongoing or periodic basis. The smart phone itself be configured with functionality operational thereon, or the collected information can be uploaded to a cloud server.

A special purpose wearable device can be configured with the functionality relevant to collect data longitudinally. This device can be considered to be an IoT enabled device. Such a device can include fitness tracking, GPS, and communications capability to collect, store, and transmit the relevant information.

In a further implementation, a special purpose device can be implemented to serve as the hub for collection of wearer data. For example, a device can be configured to locally collect information associated with a patient's wearing of a medical/therapeutic compression garment, and thus will operate as a medical device associated with the patient. Such hub can be configured as a single point of collection for relevant patient data (e.g., fitness trackers, scales, exercise equipment) associated with the patient between digital imaging events.

In implementations, the data collection hub can be in communication with a cloud computing server, or each can be configured to collect information locally until that information is uploaded onto a secure server, such as at a clinician's office during a patient visit. In an implementation, the wearable device or hub can be configured to collect information without processing thereof locally, or each can be configured with edge computing functionality that can allow at least some local processing of patient data. In the latter implementation, alarms or notifications associated with patient diagnosis and treatment can be generated. In some aspects, an alarm or notification can be transmitted to a clinician with or without the associated data from the medical device or hub. Proactive notifications or alarms can reduce the possibility that a patient's condition will deteriorate quickly during clinic visits. Such information can be incorporated into the collected information for use as a priori information useful in anthropometric measurement including one or more anatomic landmark locations and functional garment fitting events or as information deployable in a digital twin environment to improve the knowledge base for other patients.

In a further aspect, the functional garment can itself incorporate IoT functionality that can provide information about whether the garment is being worn by the person as directed. In the context of a medical/therapeutic compression garment, the garment can be fabricated with GPS functionality, for example. Such GPS functionality can provide information that the person has (or has not) worn the compression garment as prescribed or indicated, especially when such information is combined with other available patient information (e.g., GPS information on a smart phone, etc.) Accelerometer functionality can also be useful in this regard.

To develop richer insights about either or both of the wearer and the functional garments, the person can be queried from time to time automatically to collect information about her experience with the garment. For example, an app associated with a person who is prescribed a medical/therapeutic compression garment can be configured to send text notifications to the patient asking "How do you feel today?," or "Are you wearing your compression garment?," or "Do you want to speak to your health care provider?" A healthcare provider can be notified of the patient's response and, if appropriate, the provider can contact the patient directly to allow any concerning responses to be addressed in a timely manner. Information provided by the patients and any information associated therewith can be included in the patient's health record and in any collected information deployable according to the processes herein. As would be appreciated, such wearer queries can be via phone or email. A list of acceptable responses can be presented for selection, or the wearer can be prompted to enter her responses via text or recorded message.

As another example, for a worker who is wearing a functional garment intended to improve or augment her work performance, relevant queries from time to time about whether and to what extent the subject garment affects her work can be generated. The information can be collected for use with other information to generate improvements in a number of dimensions.

The methodology herein can also be expected to generate more accurate functional garment fit information over time. Rather than relying on legacy assumptions about body shapes, biomechanics, ergonomics, etc. that currently underpin the engineering and fitting of functional garments, the methodology herein can enable the generation of a large and objective database of information that can have utility in driving real improvements for the broad class of garments that are considered to be "functional."

In the context of medical/therapeutic compression garments, the generated information can allow the identification of patterns of characteristics that may exist for persons who are actually or potentially in need of treatment with compression therapy. This can generate a knowledge base that can allow a better design of medical/therapeutic compression garment sizing for prefabricated garments for the group/class of persons who are more likely to need compression therapy. For example, it could be expected that a population of persons who are more likely to need compression therapy may fall into a classifiable group of persons, such as in an age range, BMI range, surgical history, etc. Rather than estimating sizes based on assumptions that are validated by sales figures and subjective estimates of population characteristics, the leveraging of actual patient data generated from the processes herein can allow the refinement of both the designs of compression garments and the allocation of manufacturing resources and inventories associated with prefabricated compression garments. Moreover, this knowledge base can serve as a framework for testing assumptions about the patients and the therapeutic effectiveness of the prefabricated compression garments that are prescribed or indicated for them according to the methodology herein.

In a further implementation, the methodology herein can be used to determine a likely effectiveness of a functional garment as worn by a patient in need thereof. Given the importance that a functional garment imparts the intended functionality to the person when worn by a person, there is a need for generating information relevant to the performance of the garment vis a vis that person over a period of time of interest. If the subject garment loses its functionality, such as by losing structural integrity through use, the intended functionality will not be imparted to the wearer as prescribed or intended. If the wearer loses or gains weight or otherwise experiences a change in measurements over time, the garment will not fit correctly, and it can be expected that a once properly fitted garment will no longer impart the prescribed or intended functionality. The methodology herein can be used to monitor the fit of a functional garment over time for a wearer and, if appropriate, new fit information can be generated for the wearer. Information associated with such updated fit information can be incorporated into the collected information library.

The information can also be used to predict a need for a new functional garment and to provide a replacement as needed for an individual. In the context of a medical/therapeutic compression garment, the information can identify a patient as being in need of a replacement compression garment, and the system can be configured to automatically select a replacement garment to send to her. Such selection can be augmented by the collection of additional images of the person from which anthropometric measurements can be derived. The information can also incorporate information generated from other sources, such as specific biometric information for the person, queries via app, etc.

Using medical/therapeutic compression garments as an example, under current conventions, such compression garments are indicated for replacement at certain intervals (e.g., 6 months, 12 months, etc.). However, existing garment replacement protocols are generated substantially without reference to the actual performance of the subject compression garment for an individual in need of compression therapy during the time and under the conditions that garment is being worn (or not worn) by that person. The methodology herein can be configured to generate a prediction of the effectiveness of a medical/therapeutic compression garment for an individual based, at least in part, upon simulated wearing of the subject garment, such as by generating a digital twin of the individual that is based on collected compression garment information generated from a population of wearers. A person who is more active may be indicated as requiring replacement of a medical/therapeutic compression garment on a more frequent basis, for example. A person who is on a weight loss regimen in conjunction with her compression therapy may need replacement of her compression garment, including with the generation of new sizing and compression amounts, that aligns with her weight loss. In conjunction with other information that might be acquired for use with the methodology herein (e.g., exercise levels, caloric intake, etc.), simulations associated with the patient's digital twin can allow a new compression garment to be selected for the individual.

In further implementations, the anthropometric measurements including one or more anatomic landmark locations generated from the 3D reconstruction for the first body part or body area can also be used to diagnose or to assist in the diagnosis of a condition of interest that is known to or that may be associated, at least in part, with the generated measurements of one or more body parts of interest person. Such determination can be made from anthropometric measurements including one or more anatomic landmark locations derivable from one or more body part or body area 3D reconstructions in a first imaging event or from anthropometric measurements derivable from a plurality of imaging events whereby a change in measurements for the person can be seen over time. For example, the anthropometric measurements including one or more anatomic landmark locations can allow or assist in the diagnosis of lymphedema or edema-like conditions when the person is symptomatic thereof and the symptoms present to be derivable as information from a body part or body area 3D reconstruction, as set out herein. Changes in a patient's measurements over a period of time can be compared with her measurements and/or with the measurements of others to identify improvements (or the lack thereof) in the first patient's condition of interest over time.

Insights for other conditions of interest relevant to or associated with a subject functional garment can also be generated. For example, a loss of muscle tone over time can provide insights into a difference in physical activity in a person between imaging events which can, in turn, provide insights into a physical or personal condition (e.g., pain, change in amount of free time, etc.) that could reduce the propensity of the person to exercise. Such information can be configured to prompt a healthcare provider to inquire about the person's situation that would generally be visible in an episodic healthcare visit.

The present methodology provides improvements in the generation of functional garment fit information over what has been available previously by creating a robust knowledge base generated from a plurality/population of wearers. In the context of medical/therapeutic compression garments this can effectively allow collection of a large dataset to better systemize the fitting of compression garments by at least partially automating health care provider expertise. It is expected that by creating standardization of garment fitting processes via the objective methodology herein variability in fitting amongst a highly diverse patient population and within a disparate group of healthcare providers can be reduced. When such variability is at least partially removed from the compression garment fitting process, attendant improvements in compression therapy application and management of the effects thereof will result.

Generation of a database of functional garment fit information that can be deployed in machine learning processes and digital twin implementations is a feature of the present disclosure. To date, no robust database of functional garment fit information has been possible, at least because each manufacturer maintains its own technical and business information as trade secret information to ensure that each company can maintain its existing competitive advantage. In the non-limiting example of medical/therapeutic compression garments, the information that manufacturers circulate to clinicians as instructions for compression garment fitting is based upon patient data that is, at least in part, based on historical collection of patient information that can be seen to have been conducted using non-systematized methods. While such compression garment fit information can be effective for individual patients who are being monitored, the absence of a large collection of patient information means that the effectiveness of compression garment fitting and measurement of therapeutic effects remains largely ad hoc. It follows that, at least for some patients, existing compression garment information fitting instructions may be suboptimal.

While the disclosure provides improvements in the generation of anthropometric measurements including one or more anatomic landmark locations having utility in the fitting of the broad class of "functional garments," the inventors have also developed methodology specifically directed toward framing the parameters for automated generation of medical/therapeutic compression garment fit instructions for a patient in need of compression therapy, as well as to enable detection of clinical indications relevant to lymphedema and the broader class of edema-like conditions. Additionally, the inventors have determined that this novel collection of information can be used with associated relevant patient data to further enrich the data available for automated analysis of 3D reconstructions of a patient body part or body area for the fitting of medical/therapeutic compression garments for a person in need of fitting thereof.

Existing medical/therapeutic compression garment fit instructions based on historical knowledge collected or developed by compression garment manufacturers, researchers, and/or clinicians can be used to seed the feature sets used to generate some or all of the information needed to generate compression garment fit instructions for the selection of a prefabricated compression garment or the fabrication of a custom compression garment for a patient. Information existing for the generation of medical/therapeutic compression garment fit information that are provided to assist in the generalized fitting of compression garments or in the fitting of a specific manufacturer's compression garments can be leveraged to confirm or validate the automatic identification of locations of various anatomic landmark locations of the patient from the isolated/segmented body part or body area 3D reconstruction corresponding to the patient body part or body area in need of fitting for compression therapy.

Broadly, the collected anthropometric measurements including one or more anatomic landmark locations and other information present in the information library can also have utility in engineering and fabricating functional garments, and such uses are contemplated herein. For example, methods for fabricating medical/therapeutic compression garments using the compression garment fit instructions are also included in the present disclosure. Such custom compression garment fabrication instructions are disclosed in detail in the '581 and '438 Patents, previously incorporated herein by reference in their entireties.

Still further, two or more body parts or body area 3D reconstructions on the same patient can be analyzed to identify visible characteristics that may be indicative of an underlying medical indication, such as fibrotic tissue in one leg, but not the other. The system can identify a relative difference between the first and second legs in a patient vis a vis each 3D reconstruction thereof, and the information library can be configured to identify a diagnosis or reason for the differences. Notably, a clinician would typically be able to identify such an indication when examining a patient in real life. In the present disclosure, automated processing of each of the 3D reconstructions of the subject body part or body area can allow an automated detection by identifying fibrotic tissue or other characteristics from the reconstructed body part or body area shape. Weakness in a patient that present as differences in limb size, such as in a person undergoing physical therapy after a stroke or in an elderly person at risk of falling can also be detected. This methodology can also be used to detect and identify reasons for difference in two body part differences that may not be directly related to medical diagnoses, such as a mismatch in training for an athlete that presents as differences in muscle formation or improper technique in the performance of a work duty.

In further implementations, the methodology can incorporate a step of analyzing a 3D reconstruction of one or more body parts or body areas to select a method from which one or more anatomic landmark locations can be derived from a body part or body area 3D reconstruction for that person. In conjunction with determining the processing method appropriate to generate body measurement information, a person's body part or body area 3D reconstruction can be analyzed to determine whether anatomic landmark location information of interest for a person's body part or body area can be derived therefrom and, if so, what processing methodology should be selected to provide such information. The body part or body area 3D reconstruction can also be processed to determine whether other relevant information for the fitting of a subject garment can be derived therefrom. By way of explanation, if the body part or body area 3D reconstruction is intended for use in fitting a leg compression garment, the reconstruction will need to provide information relevant to the application of a prescribed or intended amount of compression therapy to the leg of the person in need thereof including, for example, a plurality of body part or body area circumferences, anatomic landmark location identification, and body part or body area lengths, where such measurement information needs to have a level of accuracy appropriate to provide a prescribed or intended amount of compression therapy for the person. For a body part or body area 3D reconstruction that is intended to provide information about fitting of a knee brace to the leg of a person in need thereof, the reconstruction will need to provide information relevant to the application of a prescribed or intended about of structure/support to the person's leg, which will be associated with a plurality of circumferences, anatomic landmark location information relevant to that person's prescribed or intended amount of support, and body part length. Yet further, if the body part or body area 3D reconstruction is intended to provide information relevant to the fitting of jeans to the person, the 3D reconstruction will need to provide information relevant to a desired fit/style for the person, where a plurality of body part or body area circumferences and a body part or body area lengths will be needed, however, functional information associated with either the compression garment or the knee brace will not be needed. While a single body part or body area 3D reconstruction generated from the person could suffice for each of these use cases, the information needed for each garment may be different at least because of the different functional characteristics to be imparted by the subject garment. Therefore, a different processing method for a body part or body area 3D reconstruction can be selected from which to derive garment fit information depending on the intended function or use of a garment.

Yet further, the methodology herein can be implemented to generate anthropometric measurements for a collection of persons. The accurate generation of anatomic landmark location information from a collection of persons, which can be further associated with demographic information as set out elsewhere herein can provide consumers with enhanced insights as to whether one or more garments in a collection of garments is likely to (or not to) fit her. The system can compare the measurements generated from a first person with a collection of measurements generated in previous measurement events to identify one or more persons having substantially similar measurements. Garment fit information can be included in the library to allow the fit of one or more garments in the library to be predicted. Such prediction can be provided to a consumer or a retailer to enhance selection of a garment for a person. Yet further, the information for a collection of persons can be used by a garment manufacturer in the design and manufacture of garments.

Figure 7A:
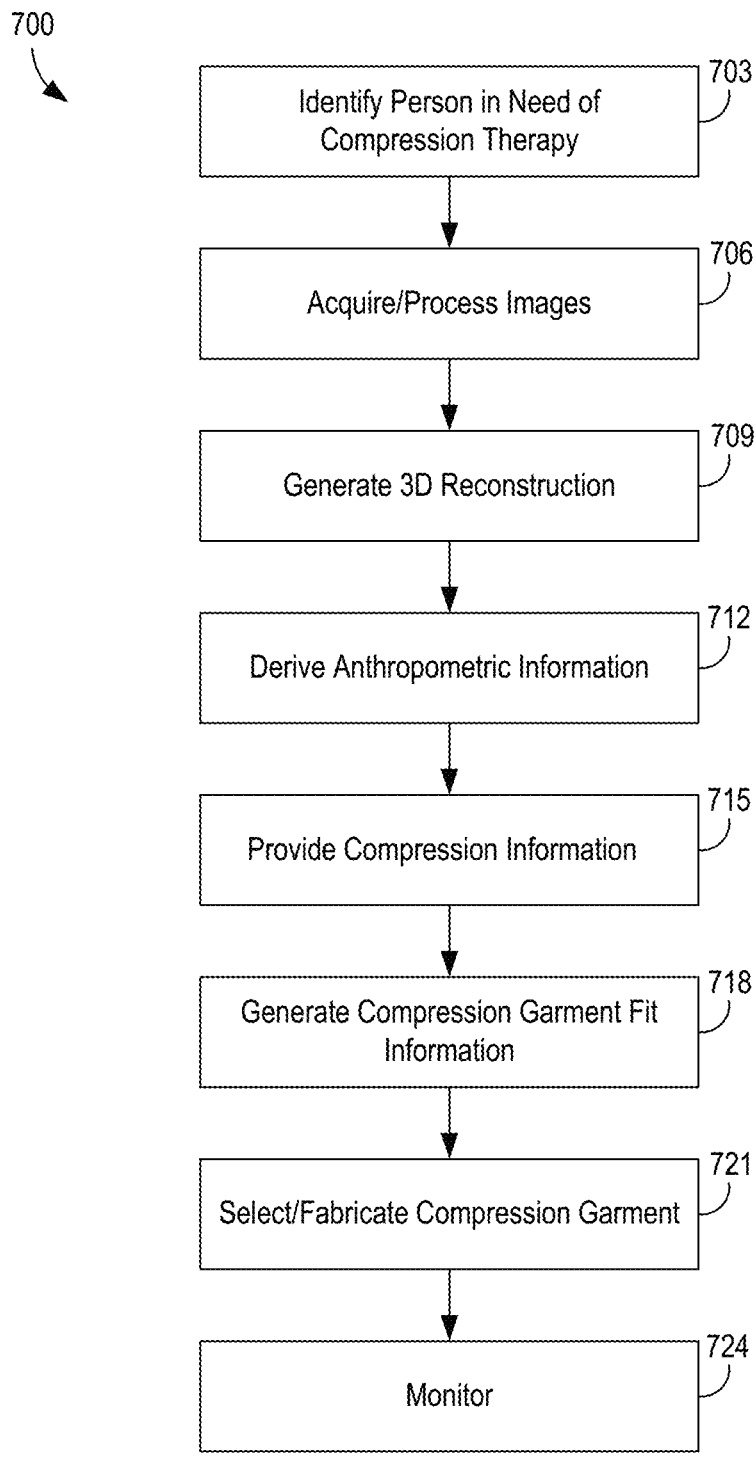
FIGS. 7A-7D illustrate an example of the derivation of anthropometric information for fitting compression garments, in accordance with various embodiments of the present disclosure.
Figure 7B:
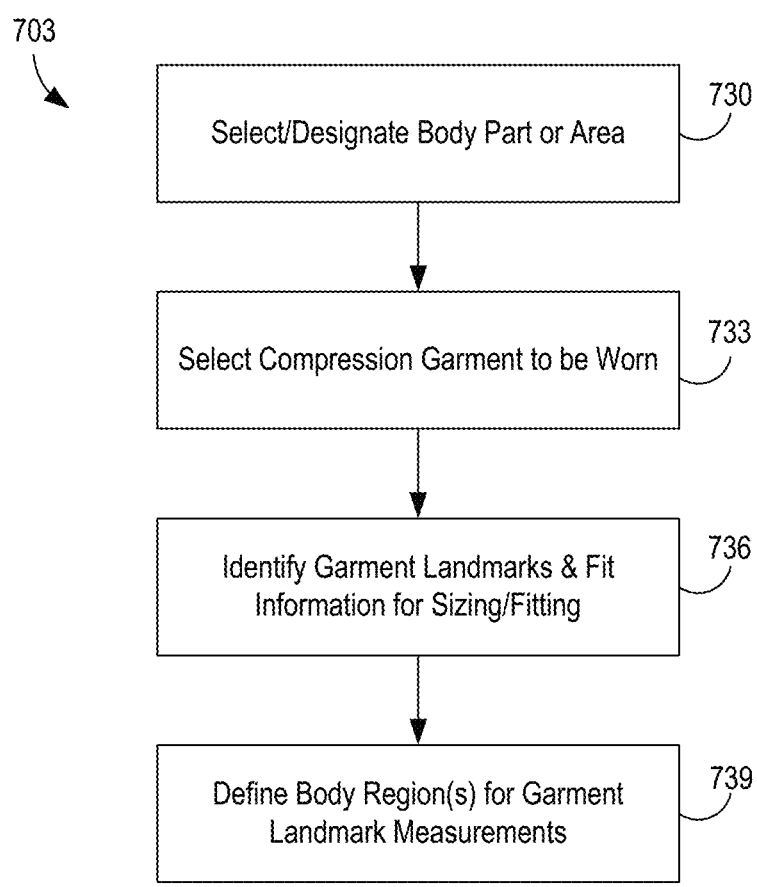

Referring to FIGS. 7A-7D, an example of a process for the derivation of anthropometric information for fitting compression garments is illustrated. Beginning at 703 in FIG. 7A, a person in need of a prescribed or intended amount of compression therapy for a selected body part or body area can be identified. FIG. 7B illustrates an example of the identification methodology at 703. For example, a body part or body area for the identified person can be selected or designated for the compression therapy at 730 and a compression garment to be worn can be selected or specified at 733. Garment landmarks and fit information used for sizing and fitting the specified garment can then be identified at 736 and body region(s) to be measured to provide identified garment landmarks for specified garment can be defined at 739. Images of the person, including the body par or body area, are acquired and processed at 706 of FIG. 7A. The images can be processed along with a library of compression garment fit information, which can incorporate, e.g., a collection of compression garment fit instructions provided by one or more compression garment manufacturers; information associated with prior compression garment fit events for the person or for one or more other individuals potentially or actually in need of compression therapy; and/or information associated with a health condition for the person or for one or more other individuals potentially or actually in need of compression therapy.

Figure 7C:
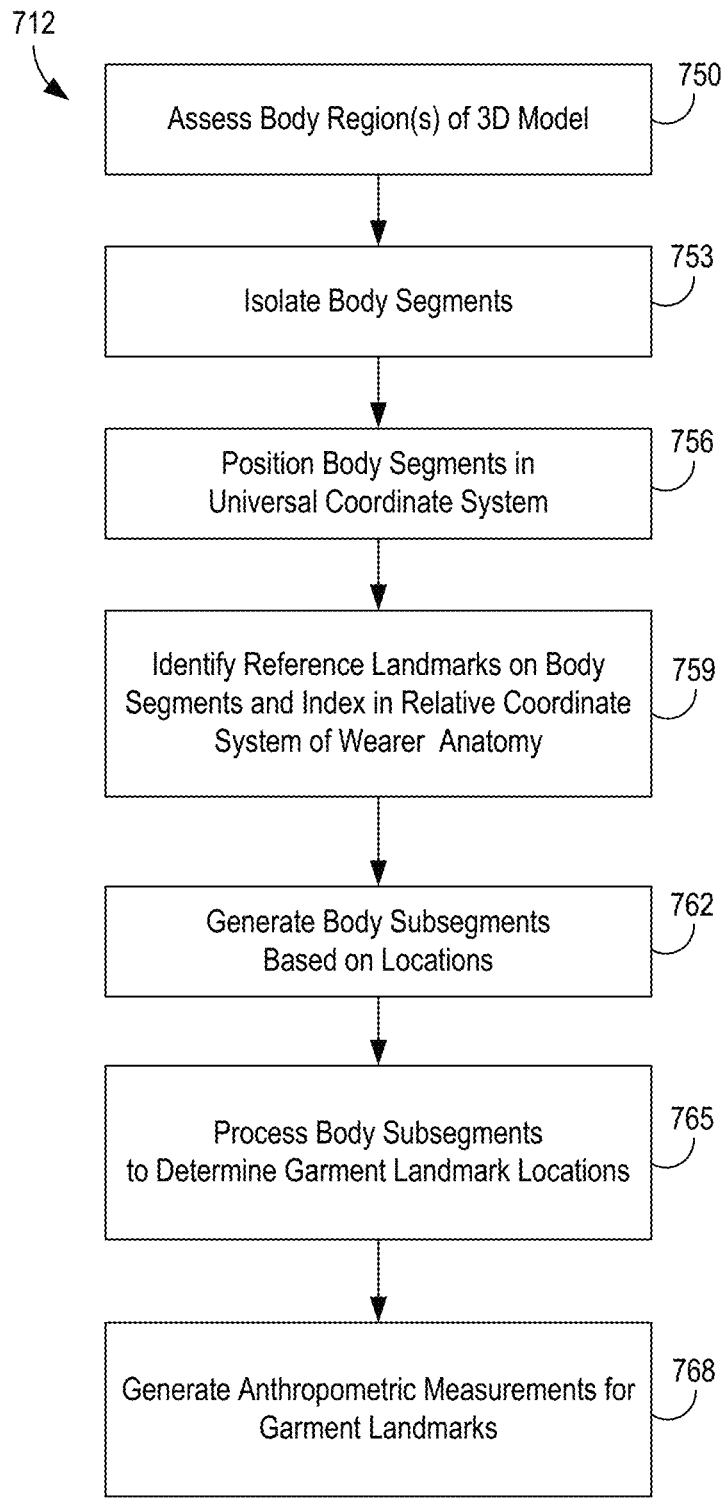
Figure 7D:
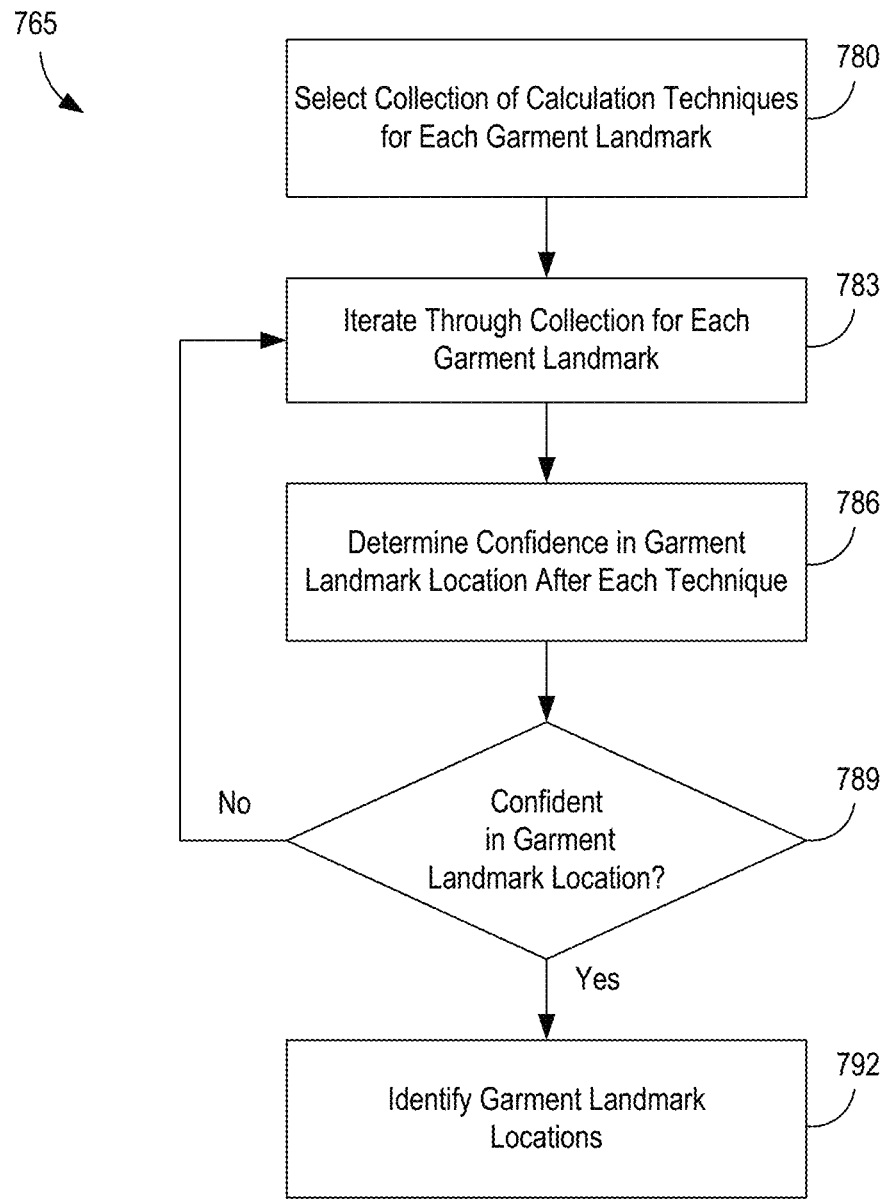

At 709, a three-dimensional (3D) reconstruction (or model) of the selected body part or body area is generated, which provides mathematically accurate information of the relevant body region(s). Anthropometric information for the selected body part or body area can be derived from the 3D reconstruction at 712. The anthropometric information can comprise, e.g., a first anatomic landmark location corresponding to a distal compression garment fit location; a second anatomic landmark location corresponding to a proximal compression garment fit location; a plurality of circumferences corresponding to at least the distal and proximal compression garment fit locations; and/or length information. FIG. 7C illustrates an example of the derivation of the anthropometric information. Beginning with 750, the body region(s) of the of the 3D reconstruction (or model) can be assessed to generate garment landmarks and anthropometric measurements. Body segments can be isolated at 753 and the isolated body segments positioned in universal coordinate system at 756 for consistent repeatable analysis. Reference landmarks are identified on the body segments and indexed in a relative coordinate system unique to wearer's anatomy at 759. Body subsegments can then be generated at 762 based on locations in the universal coordinate system. At 765, the body subsegments are processed to determine the garment landmark locations. A hierarchical iterative process of calculations can be performed for each body subsegment to determine location of the garment landmarks as illustrated in FIG. 7D. For example, a collection of calculation techniques can be selected from a repository of techniques for each garment landmark used to fit the compression garment at 780. The collection for each garment landmark can be iterated through at 783 and a confidence for the garment landmark location can determined at 786 after each technique. If the confidence in the garment landmark location is not satisfactory (e.g., below a threshold level) at 789, then the flow can return to 783 where the iteration through the collection of techniques can be repeated and a new confidence determined at 786. Ig the confidence is satisfied (e.g., at or above the threshold level) at 789, then the garment landmark locations are identified at 792. With the garment landmark locations identified, anthropometric measurements associated with the garment landmarks can be generated at 768 in FIG. 7C.

Returning to FIG. 7A, at least one compression value corresponding to a prescribed or intended amount of compression therapy applied to the selected body part or body area when the at least one compression value is incorporated into a compression garment and that compression garment is worn on the selected body part or body area is provided at 715. Compression garment fit information can then be generated from the garment landmarks and anthropometric measurements at 718. The compression garment fit information can be used at 721 to select a prefabricated compression garment for the person or fabricate a custom compression garment for the person. Periodic monitoring of the person can be carried out at 724 after the person has worn the compression garment. The monitoring can incorporate additional image acquisition, etc., for the previously selected and imaged body part or body area. If the compression garment is worn in 721, the monitoring at 724 can occur to assess whether wearing such compression garment results in an improvement or a change in the shape of the body part.

As would be appreciated, and in some implementations, accurate measurements of hands can be useful. The inventors herein have developed methodology by which accurate 3D representations of a hand can be derived from a plurality of images taken of that hand. Such 3D representations can be used to derive anthropometric information of the hand. Measurements useful for fitting of gloves or glove-like garments on the hand are accurate. As used herein, "accurate" means that 3D hand and any measurements generated therefrom are substantially equal to the real-life measurements of the person/individual from whom the 3D representation and associated hand measurements are derived. Yet further, the derived hand measurements are within about 5% or within about 3% or within about 1% of the actual measurements of the person from whom the measurements are derived from a plurality of images generated according to the methodology herein.

The hand measurements generated according to the methodology herein can be incorporated into the selection of prefabricated compression garments from a collection of prefabricated compression garments from one or more compression garment manufacturers. In other implementations, the hand measurements can be used in the fabrication of a custom garment configured for that person. One or more prescribed or indicated compression levels can be incorporated into such garments, as discussed elsewhere in this disclosure.

Such compression garments including glove or glove-like features can be useful for the treatment of lymphedema or edema-like conditions. Yet further, such compression garments can be useful for treatment of multiple indications, including but not limited to, joint stiffness, muscle aches, carpal tunnel syndrome, arthritis, diabetes, as well as in conjunction with treatment of arm fractures. Sports compression treatment can also be relevant to compression garments including glove or glove-like features.

Various levels of compression can be incorporated in compression garments having glove or glove-like features. Mild compression provides pressure of from about 8-15 mmHg and most often used for aching joints and soreness and occasionally to treat lymphedema. Medium compression provides pressure of from about 15-20 mmHg for more severe aches and pains in joints or muscles and is occasionally used for lymphedema. Firm compression (Class 1) provides pressure of from about 20-30 mmHg and usually serves as the starting point for increasing the circulation of lymphatic fluids and blood to prevent or treat lymphedema. Extra-firm (Class 2) provides pressure of from about 30-40 mmHg for more severe symptoms of lymphedema and to increase circulation and relieve hypertension. Medical compression (Classes 3 and 4) provides pressure of from about 40-50 mmHg (class 3) or to about 50-60 mmHg (class 4) for custom prescriptions.

The generated hand measurements can also be used in the selection of glove or glove-like garments where accurate fitting thereof is relevant where compression therapy may not be indicated for a wearer thereof. For example, custom gloves, such as those where a good fit is desirable, can be fabricated from the generated hand measurements. The accurate hand measurements can also be used in the selection of prefabricated gloves from a collection of gloves from one or more manufacturers. Examples of gloves where improved fit for a person can be relevant include sports gloves, work gloves, driving gloves, or the like.

A further use case for accurate hand measurements as generated herein can include the emerging area of augmented reality and virtual reality clothing products, namely gloves having functionality where improved fit can enhance natural seeming interactions between a user and virtual environments or robotic devices. Such gloves are disclosed, for example, in U.S. Pat. Nos. 10,809,804 and 10,613,626, the disclosures of which are incorporated herein in their entireties by this reference.

A realization of the inventors herein is that existing instructions associated with the generation of glove measurements can be used to provide guidance relevant to the processing of 3D image information acquired from hand imaging events. When combined with the improved hand imaging methodology and a robust library of historical information as discussed herein, such hand measurement instructions have been found to direct locations on a 3D representation of a hand derived from imaging according to the methodology herein.

Referring now to the method of generating accurate hand measurements, a plurality of 3D images can be acquired of a person's hand. The plurality of images can be acquired by an operator (e.g., a clinician) present at the same location where the person being imaged is located. The images can also be generated remotely where the operator is present at a different location than the person being imaged, where the operator can guide a user in the operation of an imaging device at a location where the person whose hand is being imaged is located. Yet further, the image acquisition by a user or an operator can be guided by a computer or via an app associated with the imaging device. One or both hands of a person can be scanned in a single image acquisition event. Image acquisition can also be facilitated by implementation of a workflow that assists the operator (or the person when the operator is not present at the imaging location) in the hand placement prior to image acquisition.

Figure 9:
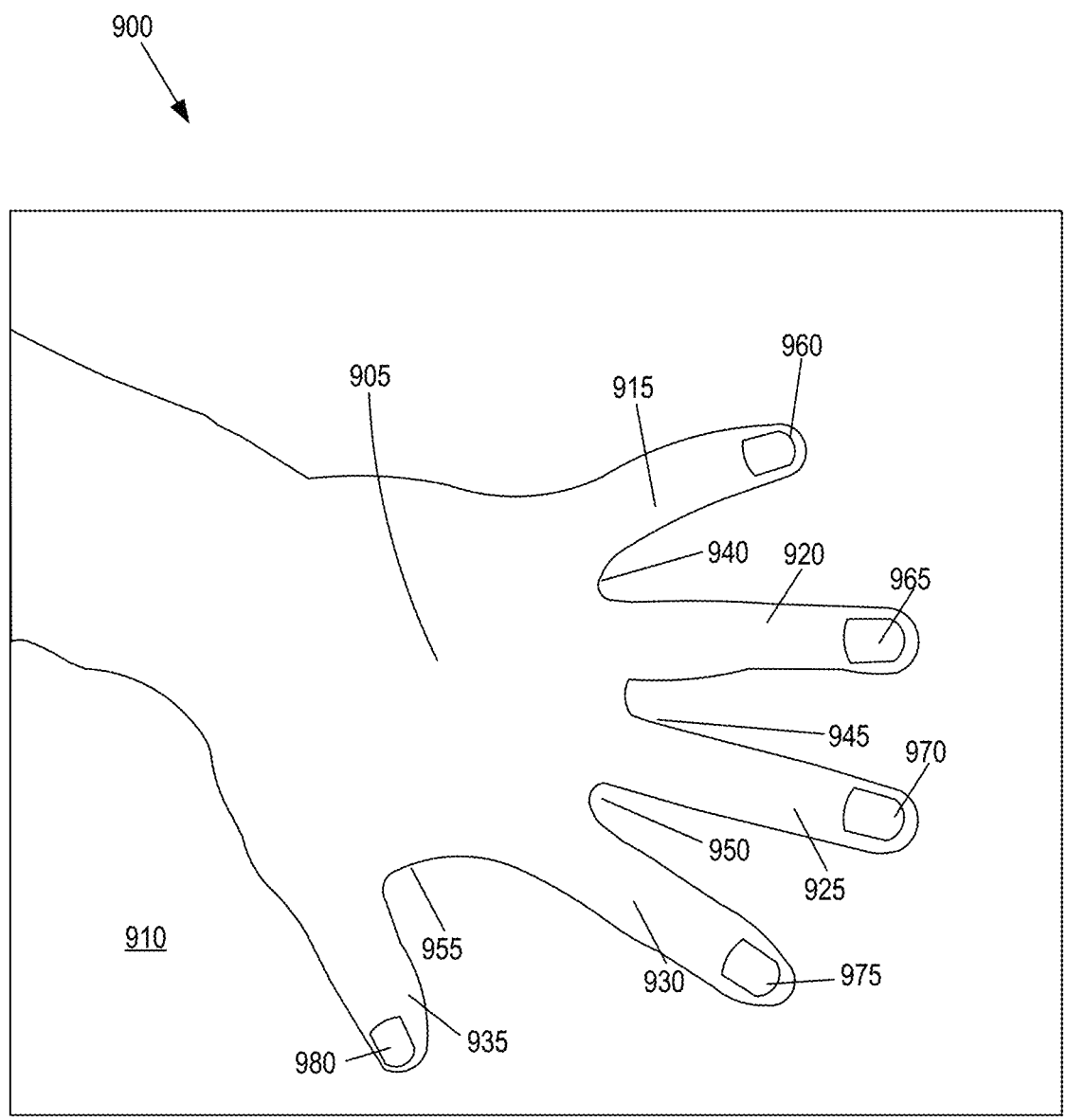
FIG. 9 illustrates a hand splayed on a surface, in accordance with various embodiments of the present disclosure.

A notable aspect of the hand imaging process of the present disclosure is the placement of a hand flat on a surface, such as a table, whereby accurate measurements of an entirety of the hand can be generated without imaging of a lower portion of the hand (e.g., the palm and associated palm-facing finger areas). As would be appreciated, the visibility of one or more hand parts (e.g., finger/thumb web portions) can vary according to the shape and size of the subject hand, especially in regard to persons who might have swelling due to lymphedema and/or obesity, for example. However, the inventors have determined that by splaying the hand on a surface, as shown by FIG. 9 hereinafter, suitable hand images can be generated, including the web portions.

In contrast to the assumptions made in prior art 3D hand imaging methodologies from which hand measurements are intended to be derived, the inventors herein have surprisingly determined that it is possible to obtain accurate measurements of an entirety of a hand from which gloves can be fit for an individual even though such images do not include the underside—that is, palm facing—side of the hand. This realization, which is a result of extensive clinical work, provides significant improvements over prior art hand measurement methods—both standard tape measurements and those derived from imaging.

As for tape measurement methods, and as should be appreciated, measurement errors are common. The multiple locations required for measurement means that there are more opportunities for measurement errors to occur in the first order. Moreover, given the smaller circumferences being measured on the fingers versus those on an arm or a leg, even small measurement errors can generate relatively large overall errors.

With regard to prior art hand measurements derived from imaging, the disclosed methodology provides heretofore unrealized accuracy of the generated measurements. This is at least because a person whose hand is being imaged for measurement generation does not need to maintain her hand substantially motionless in a raised position during image acquisition, as in prior art methods. This can be highly beneficial for persons with conditions that might make it difficult—or even impossible—to maintain their hands substantially motionless for the period required to obtain a suitable number of images from which accurate hand measurements are derivable therefrom. For example, a woman who might be imaged for the actual or potential indication of lymphedema will be likely to have undergone medical treatments that frequently cause loss of strength (e.g., surgery, chemotherapy, weight loss, etc.). An imaging method that requires her to hold her hand substantially motionless while raised unsupported in the air may be difficult or impossible for her to undertake. It follows that those persons who may be most in need of hand imaging for the purpose of generating glove measurements may be the people who are least likely to be suitably imaged by such prior art methods. Even for those persons who might appear to be able to hold a hand substantially motionless in the air during imaging— for example, healthy individuals who might be imaged for non-medical glove fitting—the inventors have surprisingly determined that accurate measurements may not suitably be derived from images acquired therefrom in many cases. Even healthy and strong individuals who are able to hold their hands elevated during hand imaging nonetheless exhibit slight hand movements—which can be termed as "micro-shakes." Such slight hand movements can introduce unacceptable variability in acquired hand image information, which will, in turn, reduce the accuracy of hand measurements generated therefrom below acceptable thresholds, especially given the small magnitudes of hand measurements. That is, although micro-shakes are subtle, the loss of measurement accuracy resulting from micro-shakes can be high relative to magnitude of hand measurements.

The inventors have found that by allowing the person to maintain her hand on a surface, such as a table, during an imaging process, the hand being imaged can be kept substantially motionless during the imaging process, even by those persons who might otherwise not be able to keep their hands raised in a substantially motionless position during image acquisition. When combined with suitable image processing methodology, such as that described herein, accurate hand measurements can be derived for a person in need thereof, and such accurate hand measurements can have utility in the selection or fabrication of gloves for a person associated with those hand measurements as discussed herein.

In fitting of compression garments, the ability to generate accurate measurements of an entire hand even though a palm-facing portion of the hand is not imaged can be facilitated by use of a library of hand measurement information derived from a plurality of hand imaging events for a plurality of persons, where at least some of these persons can be actually or potentially symptomatic of lymphedema. In this regard, the inventors herein have determined from extensive clinical research, which includes the generation of tape measurements of numerous patient hands using conventional techniques, the circumferences derived from processing of the acquired images can be made more accurate by use of a historical database of hand measurement information for a plurality of persons. The processing of the acquired images can incorporate information derived from a library of information comprising one or more of: a collection of compression garment fit instructions provided by one or more compression garment manufacturers, information associated with prior compression garment fit events, or information associated with a health condition for the person or for one or more other persons potentially or actually in need of compression therapy. When the library of hand information includes information derived from a plurality of prior hand imaging events, at least some of such a priori hand information can be validated by a human to ensure that such information is accurate in the first order. In some implementations, human validation can comprise at least some hand measurement information derived from tape measurement of a hand by one or more trained clinicians.

With regard to the use of existing measurement instructions, a recognition of the inventors herein is that processing of a plurality of hand images can be guided or facilitated by use of instructions associated with existing compression glove measurement processes as provided by compression garment manufacturers. That is, while each compression garment manufacturer may provide its own version of measurement instructions for its garment selections and/or custom garment fabrication processes, hand measurement locations are currently substantially standardized among one or more manufacturers at least because of the medical nature of compression garments. Thus, one of ordinary skill in the art would be able to use conventional compression garment measurement instructions to guide the processing of image information generated from a hand measurement process. Similarly, other glove types are also associated with an associated manufacturer's measurement instructions. Such instructions can guide the identification of relevant hand landmarks/locations to be derived from the hand imaging processes herein.

Such a priori hand information has been found by the inventors herein to provide useful information relevant to those parts of an imaged hand that are not visible in a plurality of images acquired of a hand that is laying on a surface during imaging. Such library of historical information can also be associated with health information etc. as set out elsewhere herein. From this information, it has been determined that measurement information obtained from processing of 3D hand information can also be more accurate by addition of a correction factor derivable from the library of information associated with prior hand measurement events. Such a correction factor can be unique to each individual measurement, can be modulated by additional elements of the library of information including health condition of the subject and manufacturer measurement protocol, and can vary as a function of the scope and content of the historical data library associated with a specific operator, in some implementations. To this end, the exemplary processing methodology described herein may reference a specific correction value when relevant for a particular processing step; however, it is to be understood that other processing methodologies may incorporate different correction values, if any.

The processing steps discussed herein illustrate an exemplary processing methodology for hand information derived from the acquired images from which compression garments with glove or glove-like features can be generated. To this end, it should be appreciated that the specific processing methodology as set out herein represents a particular set of steps from which relevant locations on a hand that are useful for the generation of hand measurements can be identified, where such relevant locations can be associated with instructions for fitting one or more collections of compression garments having glove or glove-like features. It is expected that other methods can be used to derive the hand landmarks/locations relevant to generating measurements suitable for fitting compression gloves, as well as other glove types, especially when a library of accurate hand measurement data becomes further populated. Moreover, it should be understood that other instructions associated with fitting of gloves can also be used to fit such garments.

Measurement information derived from the processing of acquired hand image data can be incorporated in the library of historical information library for use in subsequent hand processing for the same or for different persons. The generated hand information can also be used in diagnosis and treatment information as discussed herein. For example, increases or decreases in hand size can be a useful tool by which to determine improvement or lack thereof in a person's medical treatment. To this end, changes in swelling levels can often more readily identified in smaller circumferences associated with fingers and the hand versus arm and leg data. The generated hand information can also be tracked over time to monitor changes in disease status or treatment protocol including the ongoing need and effectiveness of therapeutic compression garments.

Figure 8A:
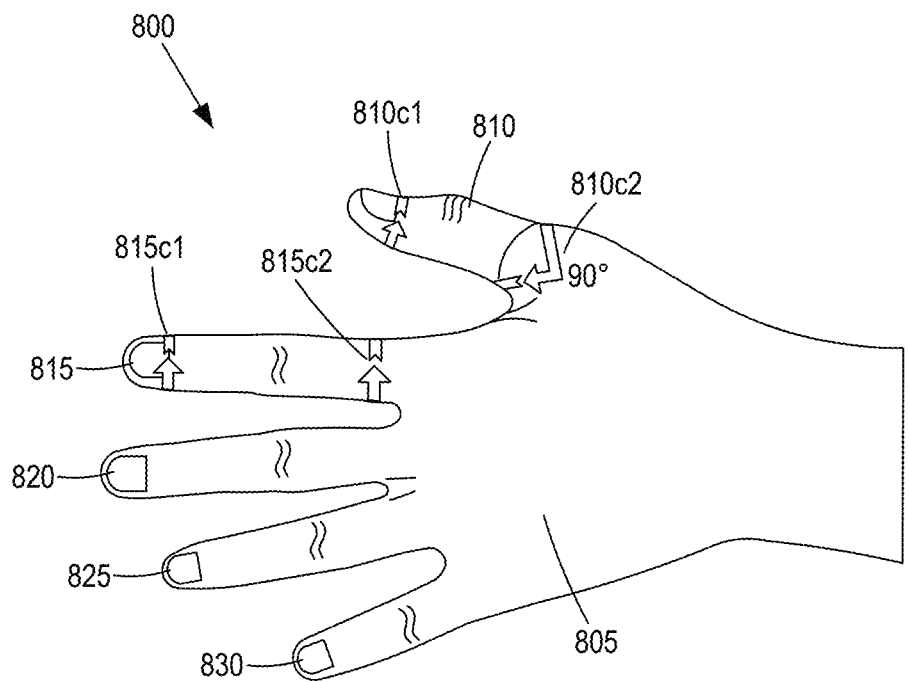
FIGS. 8A-8D illustrate examples of compression garment fitting instructions for various locations on a hand, in accordance with various embodiments of the present disclosure.
Figure 8B:
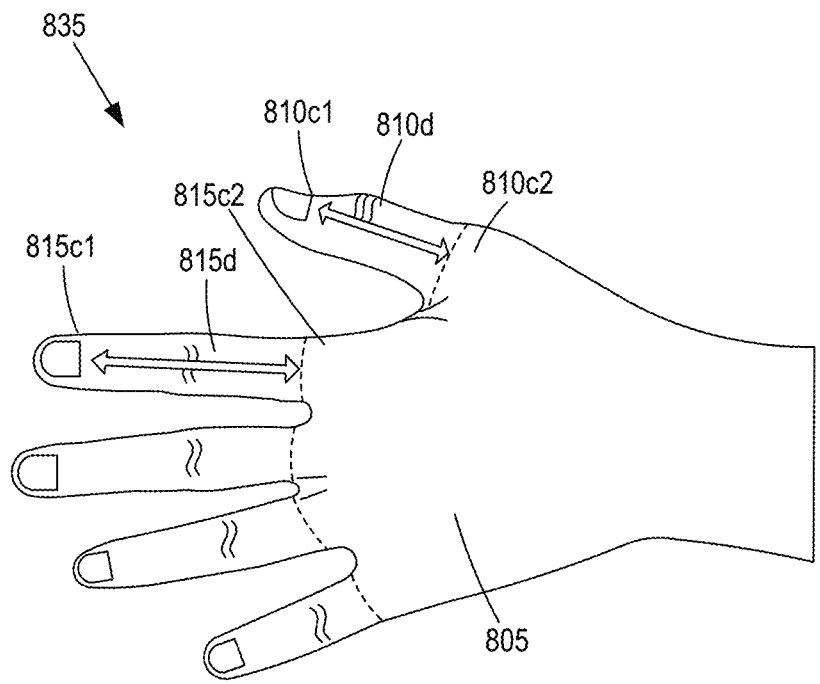

FIGS. 8A-8D illustrate prior art compression garment fitting instructions for various locations on a hand that can be useful in identifying landmarks relevant to the fitting of compression garments having glove or glove-like features using a tape measure. In FIG. 8A, instructions 800 show hand 805 with thumb 810, index finger 815, middle finger 820, ring finger 825 and pinky finger 830. Two circumferences for thumb 810 can be generated at base of nail bed location 810c1 and at web location 810c2. Circumference of index finger 815 can be generated at base of nail bed location 815c1 and at web location 815c2. Although not shown, two circumferences for each of 820, 825, and 830 would also be generated according to the instructions. In FIG. 8B, instructions 835 show measurement of thumb 810 and index finger 815 lengths 810d and 815d, respectively. Other finger length measurements can similarly be generated. Each of the measurements generated in FIGS. 8A and 8B are of hand 805 in a palm-down position as shown.

Figure 8C:
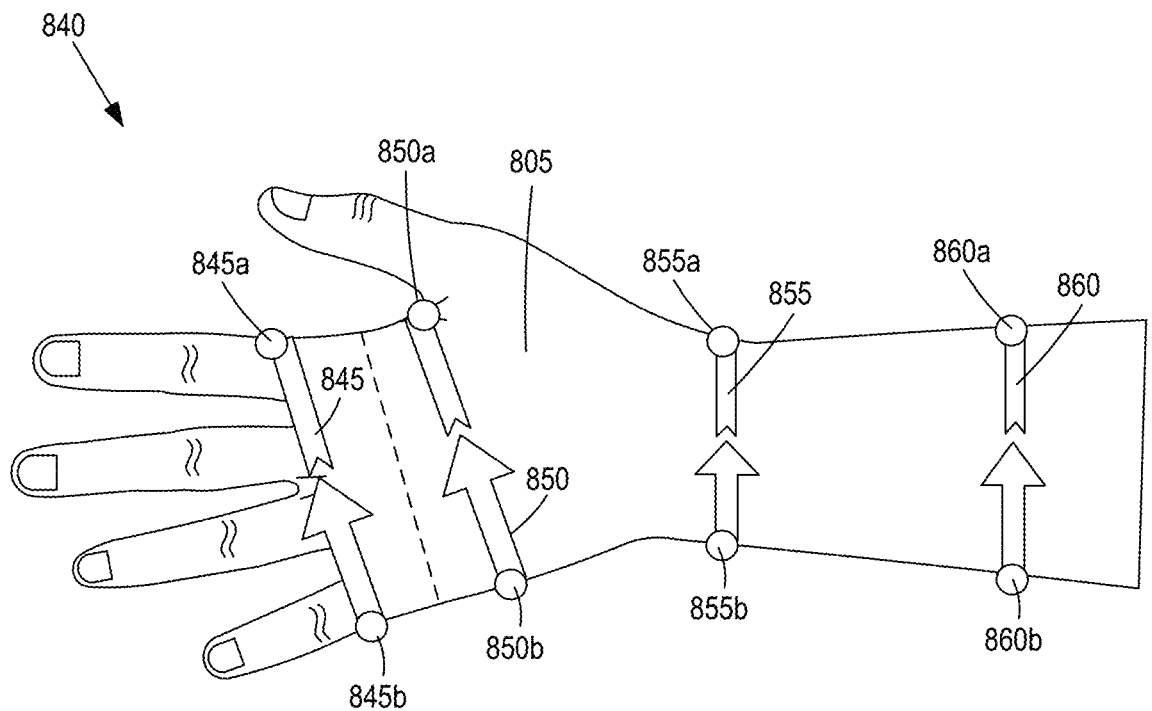

FIG. 8C further illustrates prior art instructions 840 for the generation of circumferences associated with compression garment measurements for hand 805. As contemplated by these instructions, a tape measure is used to generate lower finger boundary circumference 845 at index finger base 845a and pinky finger base 845b. Palm circumference 850 is generated at thumb web 850a and outer location 850b. Wrist circumference 855 is generated at 855a and 855b. Glove end or forearm area circumference 860 is generated at 860a and 860b. As shown, each of circumferences 845, 850, 855 and 860 are generated by a clinician's manipulation of a tape measurement with the palm of hand 805 facing down. Such palm-facing direction can facilitate a trained clinician's visual identification of the landmarks relevant to generating these circumferences.

Figure 8D:
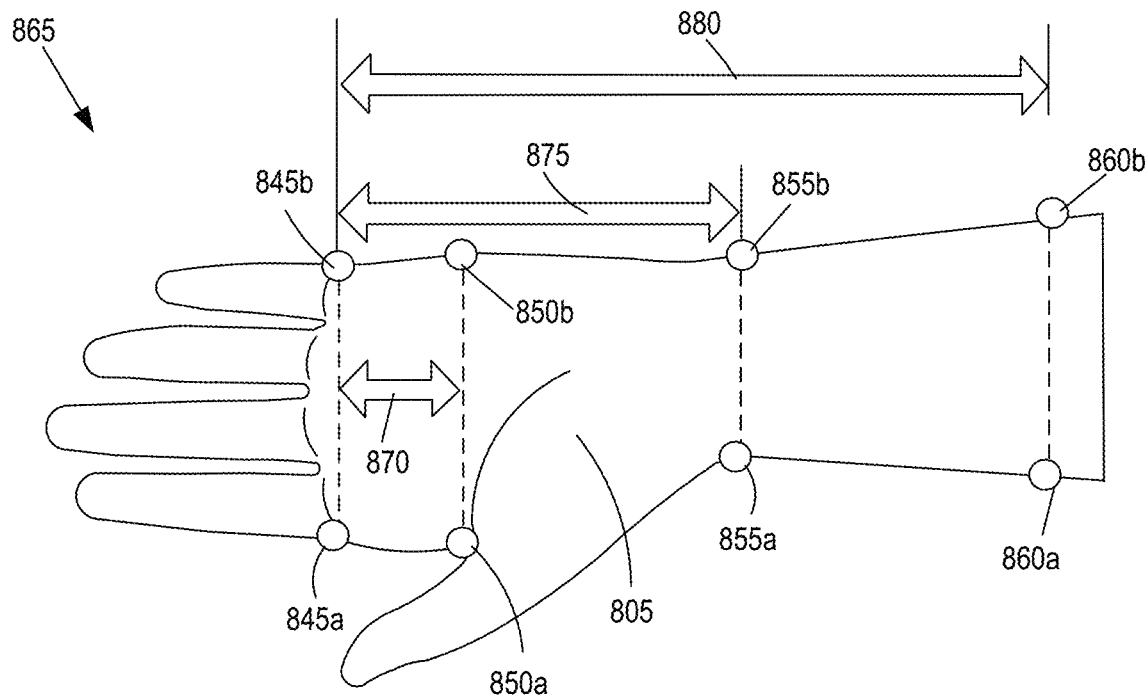

FIG. 8D illustrates prior art instructions 865 for the measurement of distances on hand 805 that are relevant to the fitting of compression garments using the tape measurement method. Length 870 is defined by a distance between 845b and 850b. Length 875 is defined by a distance between 845b and 855b. Length 880 is defined by a distance between 845b and 860b. Each of the distances shown in FIG. 8D is each associated with specific measurement locations used in the fitting of compression garments at least because the garments can be configured to apply compression to one or more areas on a hand when the garment including such compression levels is worn by a person in need of compression therapy. That is, these specific locations shown on FIG. 8D can be associated with physiological functionality associated with compression garments, namely, the application of compression to a person's lymph system. As such, the measurements illustrated in FIG. 8D can have utility in the fitting of compression garments having glove or glove-like features using the methodology herein. It can nonetheless be understood that these locations may not have utility, or may have lesser utility, in the fitting of gloves or glove-like garments that are not intended for application of therapeutic compression to the person who is wearing the garment as prescribed or indicated. Other garments may benefit from generation of measurements at other locations than the ones shown in any of FIGS. 8A-8D. Put another way, the locations relevant for generation of specific measurements from the hand imaging methodology herein can vary according to the form and function intended from a specific glove or glove-like garment. Manufacturer's instructions for fitting such gloves or glove-like garments can be used to define the locations on 3D hand information derived from imaging according to the methodology herein. Processing of such 3D hand information can therefore be informed and directed by such manufacturers' instructions. The specific 3D hand information processing described hereinafter is directed toward the generation of measurements having utility for the fitting of compression garments to the subject hand. However, it is to be appreciated that other processing steps can have utility in identifying the landmarks and measurements relevant to the fitting of other types of gloves or glove-like garments, where such processing steps are directed or guided by instructions associated with the generation of measurements.

An exemplary hand placement for imaging is shown in FIG. 9 as hand placement 900 with hand 905 shown in a splayed or open position on surface 910. As can be seen in 900, each of pinky finger 915, ring finger 920, middle finger 925, index finger 930, and thumb 935 are splayed to allow web portions 940, 945, 950, and 955 to be visible for imaging. Fingertips 960, 965, 970, and 975 are also visible in the positioning shown in 900, as is thumb tip 980. In generating hand/surface placement 900, a person in need of hand imaging places hand 905 on surface 910 (e.g., a table) by splaying pinky finger 915, ring finger 920, middle finger 925, index finger 930 and thumb 935 as shown. The methodology herein allows accurate hand measurement information to be derived from images acquired of a hand when it is imaged while placed on the surface, where such measurements can include one or more circumferences of each of the fingers and thumb, one or more circumferences of the hand, and at least one circumference of each of the wrist and forearm area. Lengths of the fingers, thumbs, hand and forearm areas can also be derived. As would be appreciated, hand/surface placement shows hand 905 present on surface 910 without reference marks. In an implementation, markers are not applied or associated with hand 905 for the imaging step. Generated hand information can thus be derived from the image information alone, that is, by processing of the images to generate the hand landmark/location information, as well as to derive measurements therefrom.

In some implementations, the imaging step can incorporate a template upon which a hand is placed flat on a surface including the template. A template can facilitate placement of the hand and/or to generate reference points for processing of the images from which to derive hand locations/landmarks relevant to processing of the acquired images, and the measurements derivable therefrom. In further implementations, markers can be placed on the hand prior to imaging to facilitate location/landmark identification. Irrespective of the presence or absence of a template and/or markers on a hand during image acquisition, the methodology herein provides a previously unrealized ability to generate accurate hand measurements including circumferences of the hand and each of the fingers and thumb even though at least some portions of the hand—namely, the palm-facing portions—are substantially not imaged during an image acquisition step. In other words, at least some portion of the hand being imaged, namely the palm-facing portions, are not included in images acquired of the subject hand.

During a hand imaging process, a plurality of images of hand 905 placed on surface 910 in a finger-splayed position are acquired using a suitable handheld imaging device, such as a Structure I/O device. Other imaging devices can be used as set out elsewhere herein. A user who is present at a location with the person having hand 905 being imaged can instruct the person to place her hand in a splayed position as shown in FIG. 9. The user can then operate the imaging device (not shown) by moving it around hand 905 freely during the image acquisition process with 6 degrees of freedom unconstrained by a mounting or support assembly.

Referring specifically to the handheld imaging method, during image acquisition, the user can be provided with guidance via instructions associated with whether a collection of acquired images can be processed to generate accurate hand measurements as discussed herein. For example, a display showing whether there are any unimaged (e.g., holes in a generated 3D mesh) or inadequately imaged (e.g., lack of suitable image overlap to generate suitable 3D definition, etc.) can be in communication with the imaging device, and the user can be directed to acquire additional images as necessary. In this regard, the image acquisition aspects of the system can be configured for at least some real time image processing to allow a user to know whether the acquired images can be processed to suitably provide accurate hand measurements from which compression gloves and other glove types can be appropriately fitted.

In some implementations, an imaging device can be moved around the subject hand during image acquisition, where the imaging device is mounted on a support, as long as the method of mounting allows the subject hand to be suitably imaged to generate accurate hand measurements. When the imaging device is not handheld—that is, when the imaging device is mounted on a support such as rod—the imaging device can be operated substantially automatically by a computer via a set of instructions.

Upon acquisition of a plurality of images of hand 905, the images can be processed to generate a 3D representation of the hand using known methodology. The processing can be conducted on a portable computing device associated with or in communications engagement with the imaging device and/or the information can be transferred to another device for processing, such as a cloud computing network. As discussed in more detail herein, measurement accuracy can be facilitated by one or more of: a collection of fit instructions provided by one or more compression garment manufacturers, information associated with prior compression garment fit events, or information associated with a health condition for the person or for one or more other persons potentially or actually in need of compression therapy.

Figure 10:
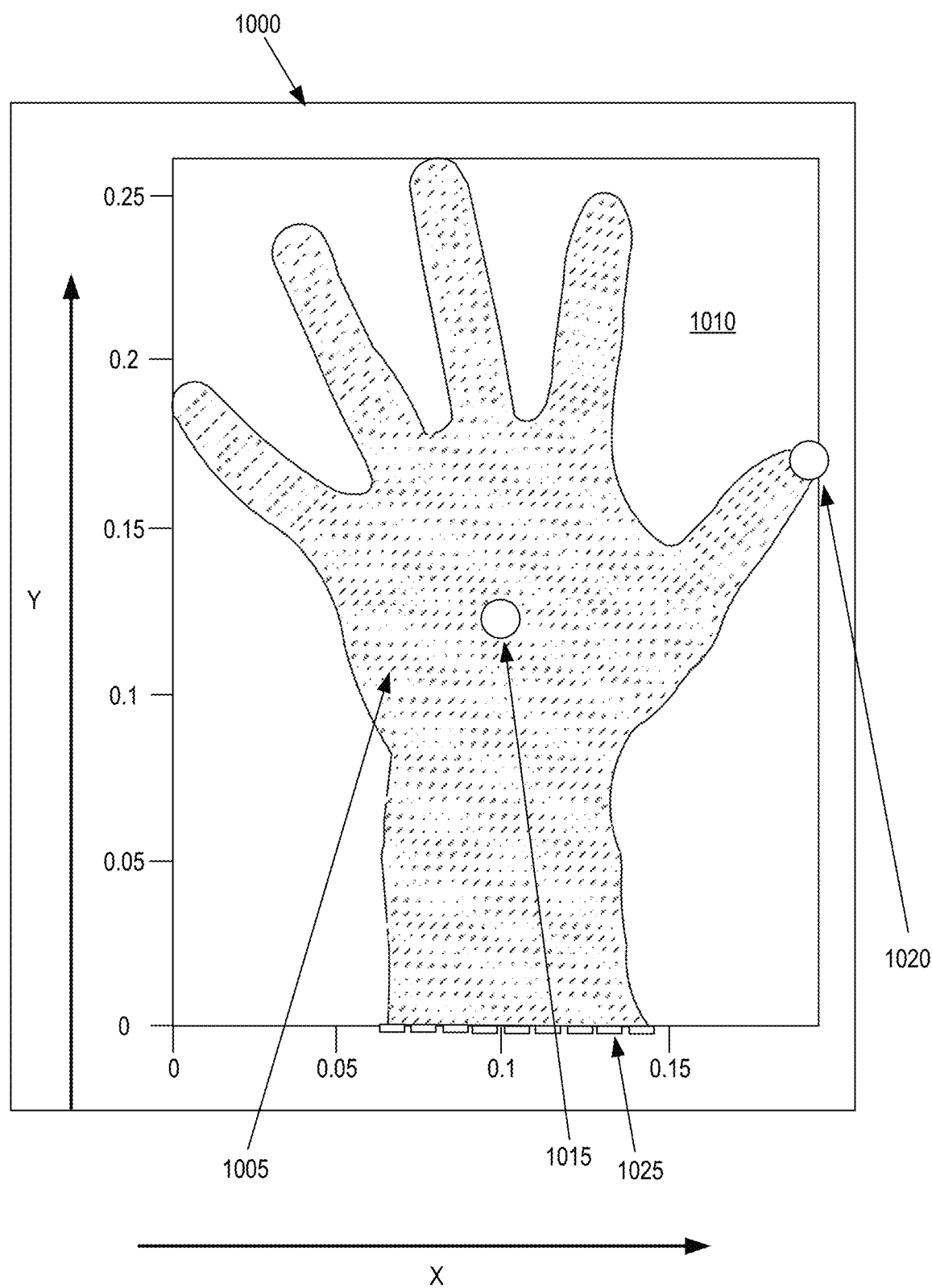
FIG. 10 illustrates an example of hand/surface representation generated from a hand imaging event, in accordance with various embodiments of the present disclosure.

As shown in FIG. 10, image information can be derived as hand/surface representation 1000 generated from a hand imaging event according to the described imaging method, where 1000 comprises each of hand information 1005 and surface information 1010 configured in Cartesian coordinates. Using positioning on the X, Y axis, hand center point 1015 can be derived, as can be thumb endpoint 1020. Hand end/forearm area 1025 is aligned with 0 on the X axis in this example to make processing easier, however, other hand placements can be contemplated.

Figure 11A:
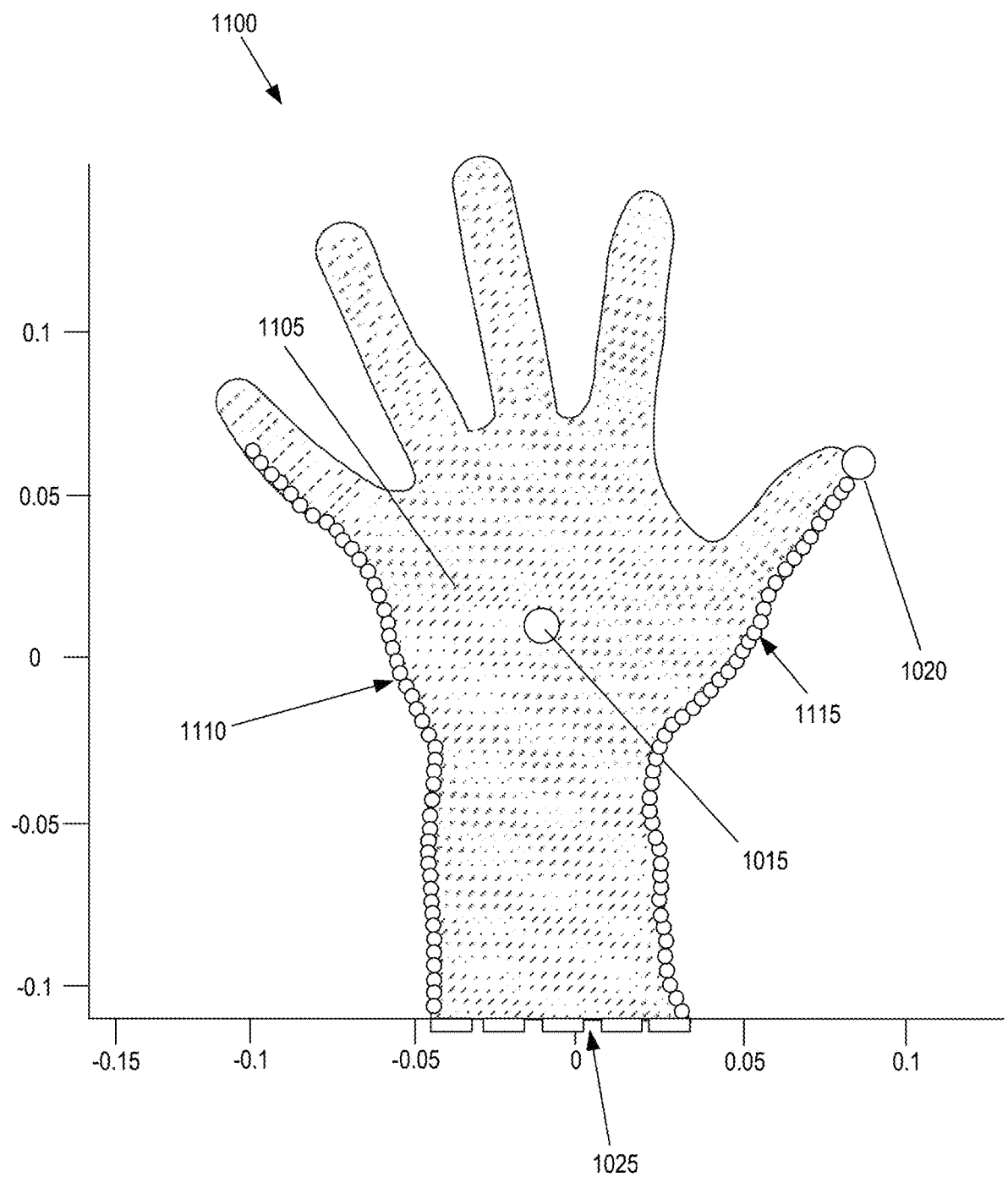
FIGS. 11A and 11B illustrate examples of hand information arranged in Cartesian coordinates, in accordance with various embodiments of the present disclosure.

In FIG. 11A, hand information 1100 comprises isolated hand information 1105 arranged in Cartesian coordinates. As would be appreciated, 3D hand information 1100 comprises an output of a processing step wherein surface information 1010 has been removed to provide isolated 3D hand information 1105. Hand end/forearm area 1025 is shown on the X axis. Thumb endpoint 1020, which can serve as a reference landmark, can be defined as the point of the isolated 3D hand information 1105 with the maximum X coordinate in Cartesian coordinates as shown, among other methods as suitable. FIG. 11A also illustrates processing output whereby each of an outer hand boundary 1110 and inner hand boundary 1115 are identified. Further processing shown in FIG. 11A provides hand center point 1015, which can be defined as the centroid of the hand in XY coordinates or as a relative position between the inner and outer hand boundaries, among other methods as appropriate.

Figure 11B:
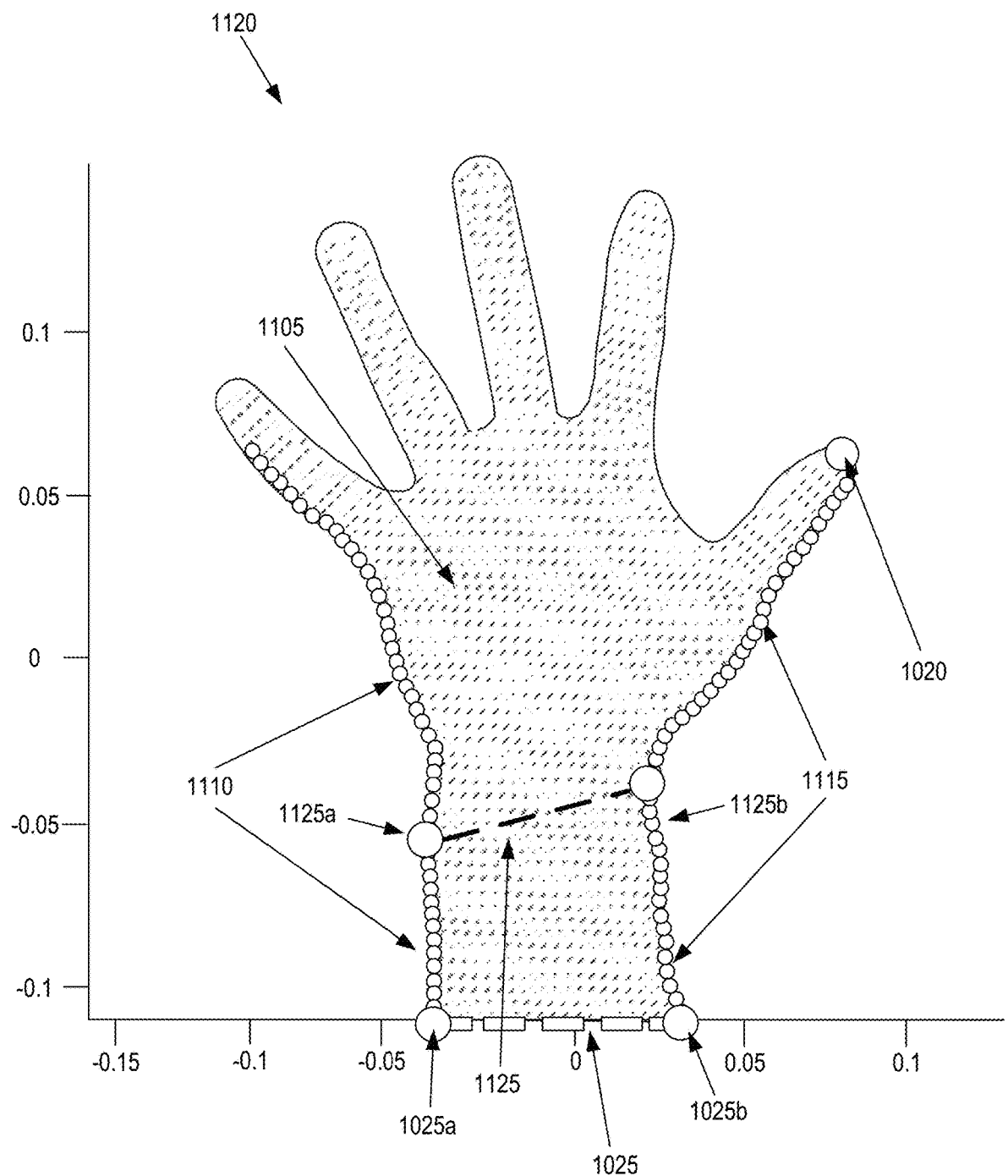

In FIG. 11B, which illustrates further processing of 3D hand information 1120, wrist location 1125 is a distance between locations 1125$a$ and 1125$b$, which can be defined as the location with the smallest distance between inner and outer hand boundaries 1110 and 1115 or as a fixed location relative to the hand center point 1015, among other methods as needed for the application. A length of 1025 at the hand end/forearm area can be defined by 1025$a$ and 1025$b$, as would be appreciated. The hand end/forearm area can be defined as a fixed distance from the wrist or other landmark or by particular anatomic characteristics as appropriate for the measurement protocol. Circumference measurements of the wrist and hand end/forearm area can be calculated by establishing cross-sectional slices at the location of 1125 and 1025, respectively. A circumference for each cross-sectional slice can be determined by identifying the points on the slice constituting the perimeter, which can be done via a boundary function, point sampling at defined angular intervals, or other method as appropriate. Circumferences can be calculated as the sum of the distances between the perimeter points, the distance of a spline function fit to the perimeter points, or other method as appropriate for the measurement protocol. Circumference measurements can include a derived correction factor to account for the palm side of the wrist and forearm that are not directly captured in the imaging event due to the hand being placed on a flat surface for imaging. Depending on the measurement tolerance appropriate for the selected measurement protocol, the correction factor can range from a simple straight-line closure of the perimeter at the level of the surface to a multi-dimensional curvature closure with an optional measurement offset correction factor as derived from the referenced library of historical information.

Figure 12A:
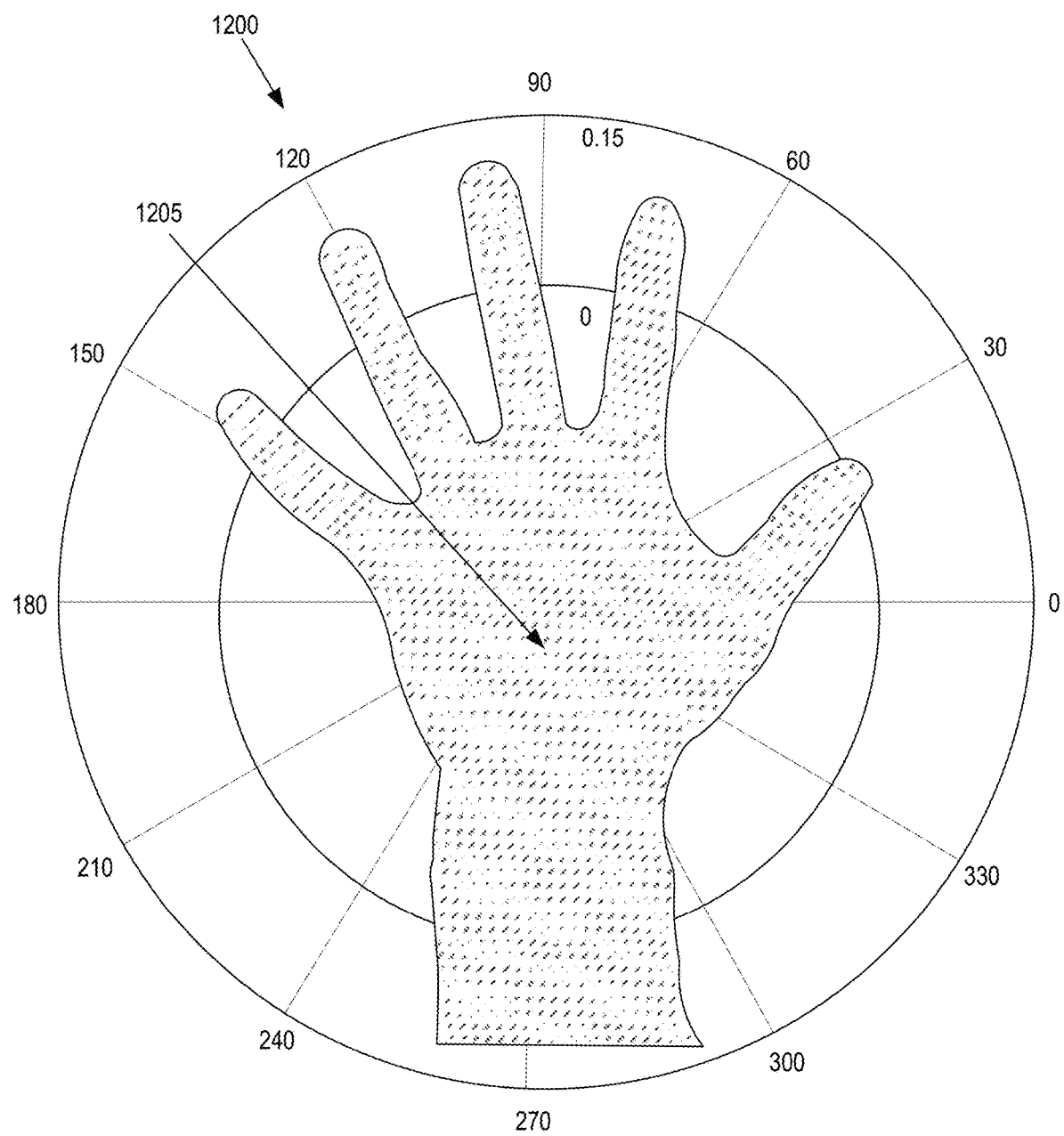
FIGS. 12A and 12B illustrates examples of 3D hand information arranged in polar coordinates, in accordance with various embodiments of the present disclosure.
Figure 12B:
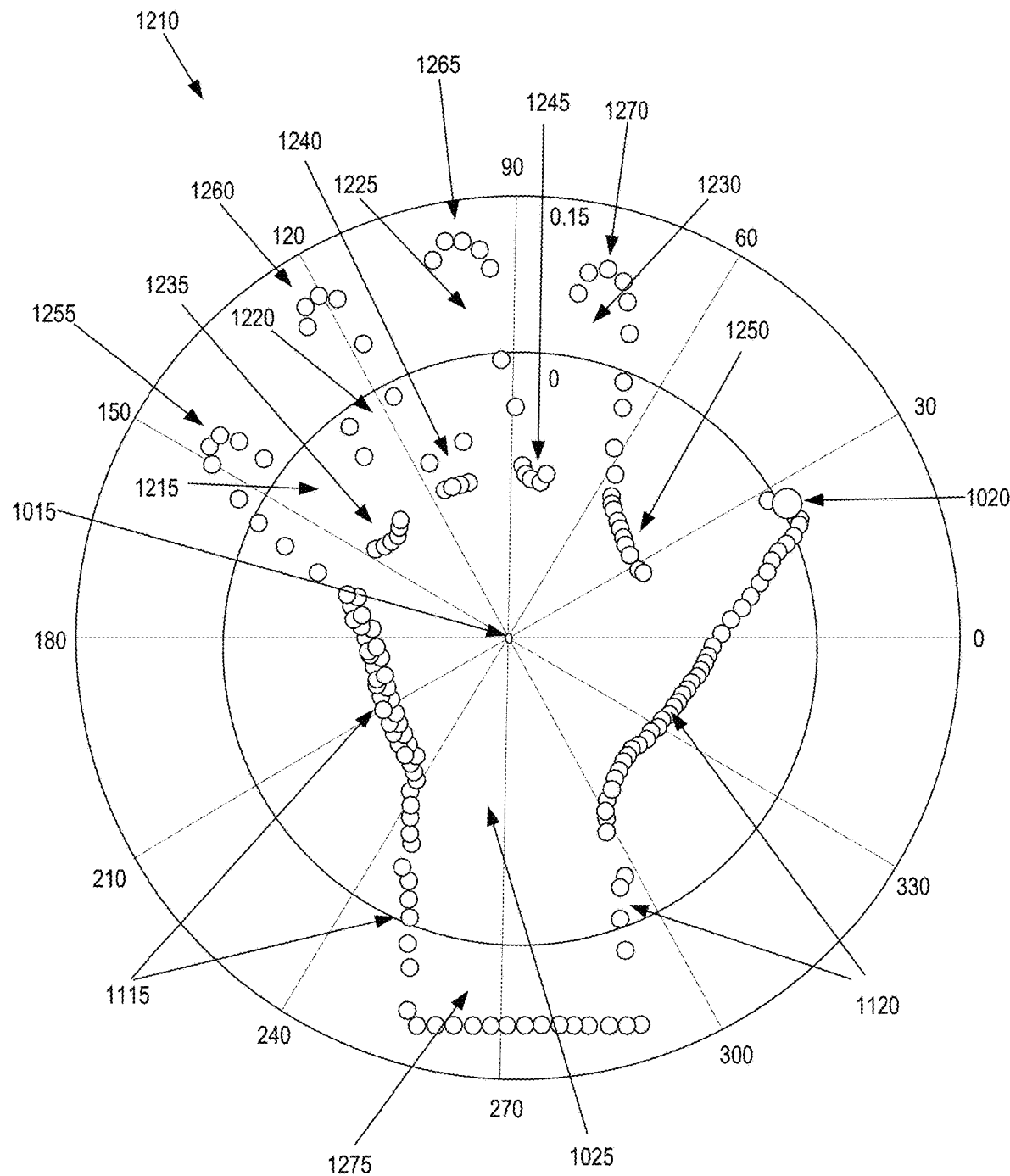

As shown in FIG. 12A, processing output from previous steps can be transferred/translated to a polar coordinate system representation 1200 as 3D hand information 1205 for further processing. Next, as shown in FIG. 12B as polar coordinate hand representation 1210, 3D hand information 1205 can be processed via a series of iterations and finger boundaries according to the expected shapes and approximate locations associated with a human hand as is available in a priori information associated with human hands generally and, in some cases, with the specific person whose hand is that in the images. Such a priori information can also be derivable from a library of hand information generated from a plurality of prior hand measurement events, where such hand measurements can be derived from either or both of tape measurements and/or imaging of a plurality of hands. A searching protocol can direct the identification of such preliminary boundaries on hand information 1205. As will be appreciated, the generation of rough or preliminary finger/hand outlines or boundaries from 3D hand information can be a first step to deriving measurements therefrom, at least because such information provides a basis for substantially automated processing of the acquired image data by defining a search space therefore. In exemplary processing steps, a temporary matrix of hand information 1205 can be generated in which theta for points in hand 1205 are rounded to a nearest degree, for example 1 degree, 2 degrees, or 5 degrees. Unique values of theta can be generated along with determination of a maximum r value for each unique theta value. In this regard, a selection of boundary points having the largest r values can be identified from processing of 1205. Any boundary points less than about 0 degrees and greater than 180 degrees can be discarded as not being associated with relevant hand data. Remaining boundary points in the collection can be sorted by increasing theta values to generate a finger array boundary (not shown). Boundary points associated with fingers 1215, 1220, 1225, and 1230, web portions 1235, 1240, 1245 and 1250, and fingertips 1255, 1260, 1265 and 1270 can be derived from such processing as shown in 1210.

Figure 13:
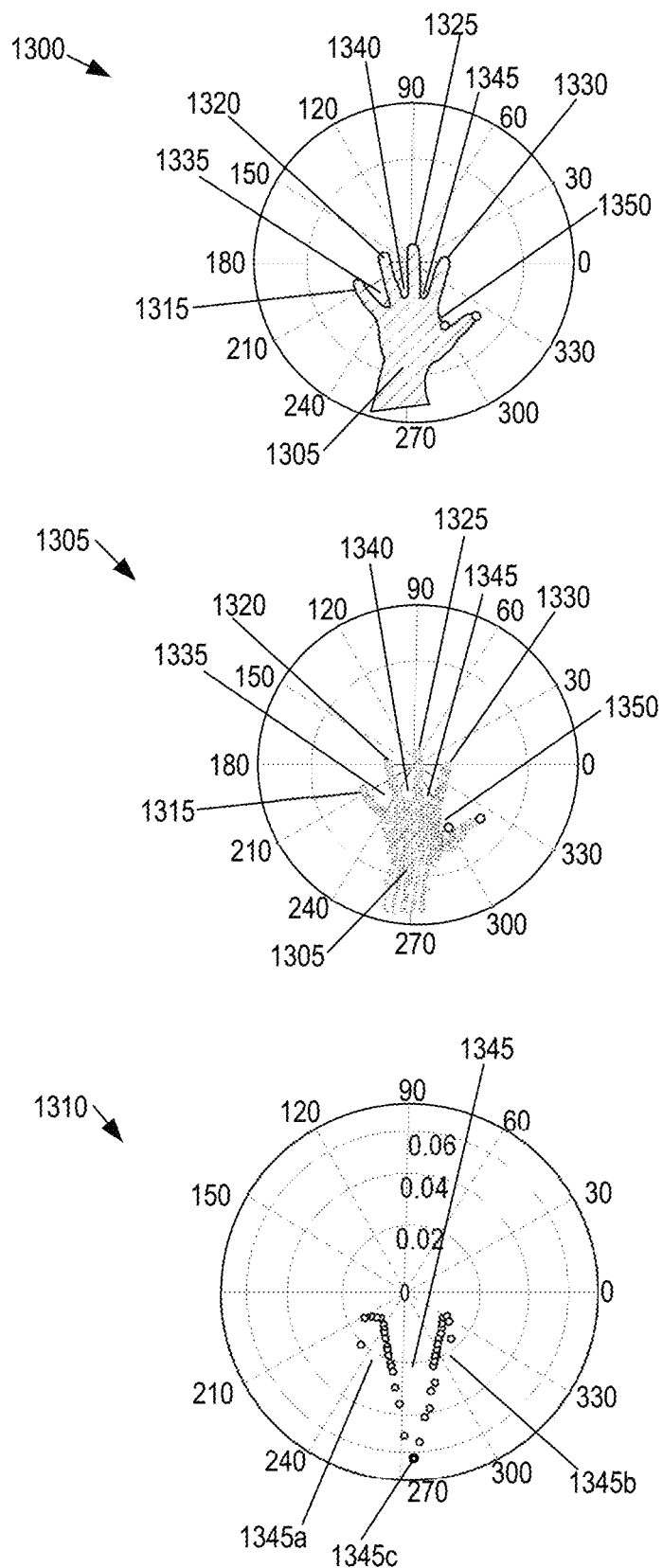
FIG. 13 illustrates examples of 3D hand information arranged in polar coordinates, in accordance with various embodiments of the present disclosure.

Turning to FIG. 13, processing of 3D hand information from FIG. 12B is further illustrated as polar coordinate representations 1300, 1305, and 1310, whereby in a plurality of processing steps each of finger web outlines 1315, 1320, 1325, and 1330 and web locations 1335, 1340, 1345, and 1350 are further resolved. In a processing step, a temporary matrix of 3D hand mesh 1305 can be created in which theta for every point is floored to a selected nearest degree, for example, 1 or 2 or 3 or 5 or other suitable values. A matrix of boundary points can be created by identifying the unique values of theta and identifying the maximum r value for each identified theta. The results of these processing steps can be seen in polar coordinate representations 1305 and 1310 and using index finger web outline 1345 as an example, the position of index finger web outline 1345 can be derived as being between middle finger 1325 and index finger 1330, and therefore being characterized as shown in 1310 as finger web portion 1345 having a first side 1345$a$ associated with middle finger 1325 and a second side 1345$b$ associated with index finger 1330. A location that is determined to be an intersection point 1345$c$ of a line defined by 1345$a$ and 1345$b$ can define the deepest portion between middle finger 1325 and index finger 1330, which can be characterized as a base position 1345$c$. The web locations 1335 and 1340 can be derived using similar processing steps. Information associated with web area 1345, as well as the other determined web locations, can be useful in subsequent processing steps, as described hereinafter. Further, as with other processing herein, the described processing steps are exemplary only. An output associated with the processing steps associated with FIG. 13 can be transformed in a reverse order to an orientation of the hand information 1305 as in 1300 for further processing.

Figure 14:
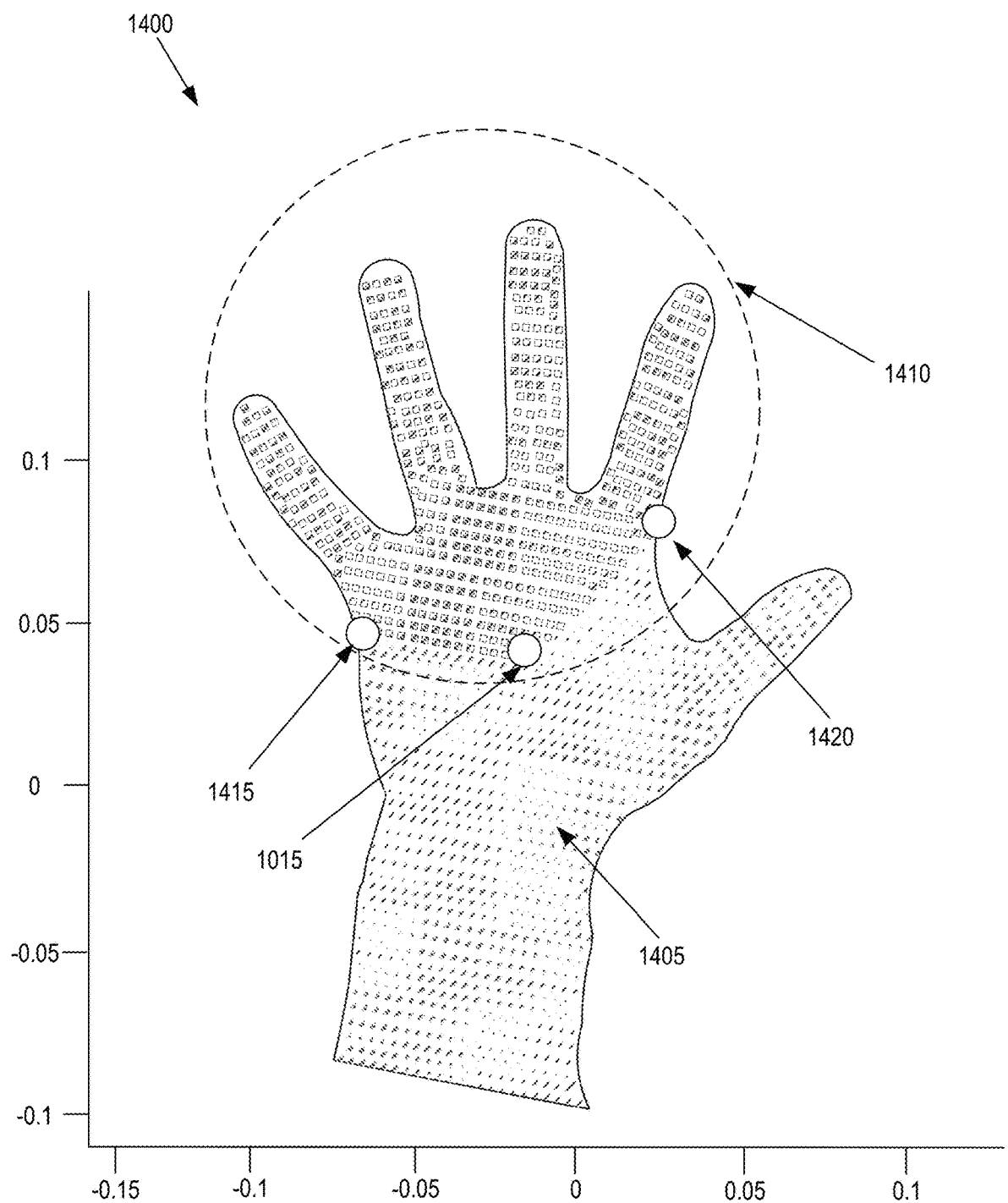
FIGS. 14 and 15 illustrate examples of 3D hand information arranged in Cartesian coordinates, in accordance with various embodiments of the present disclosure.

Referring to hand representation information 1400 in FIG. 14, 3D hand information 1405 comprises finger section 1410, which includes previously generated center location 1015 as shown in FIG. 10 and the accompanying text, and pinky finger boundary point 1415 and index finger boundary point 1420 are generated as detailed herein. To generate output associated with 1400, output from FIG. 13 can be processed to generate temporary index and pinky fingers (not shown) and finger boundaries from which finger measurements can be generated. A temporary index finger (not shown) can be generated as theta values between about 30-50 degrees and the theta coordinate of index web 1340 and r values greater than the r value of 1340. Temporary pinky finger boundary (not shown) can be defined as theta values between the theta coordinate of web area 1335 and about 150-180 degrees with r values greater than the r value of web area 1335. Each of the defined boundaries of pinky and index fingers 1315 and 1330 can then be generated. Pinky finger boundary 1415 can be defined as the point within the temporary pinky finger (not shown) that has the largest theta value. Index finger boundary 1420 can be defined as a point within a temporary index finger (not shown) that has the smallest theta value. Using the temporary index and pinky finger boundaries, finger section 1410 can be defined as all points in the hand between the theta values of pinky finger boundary 1415 and index finger boundary 1420, as further bounded by 1015.

Figure 15:
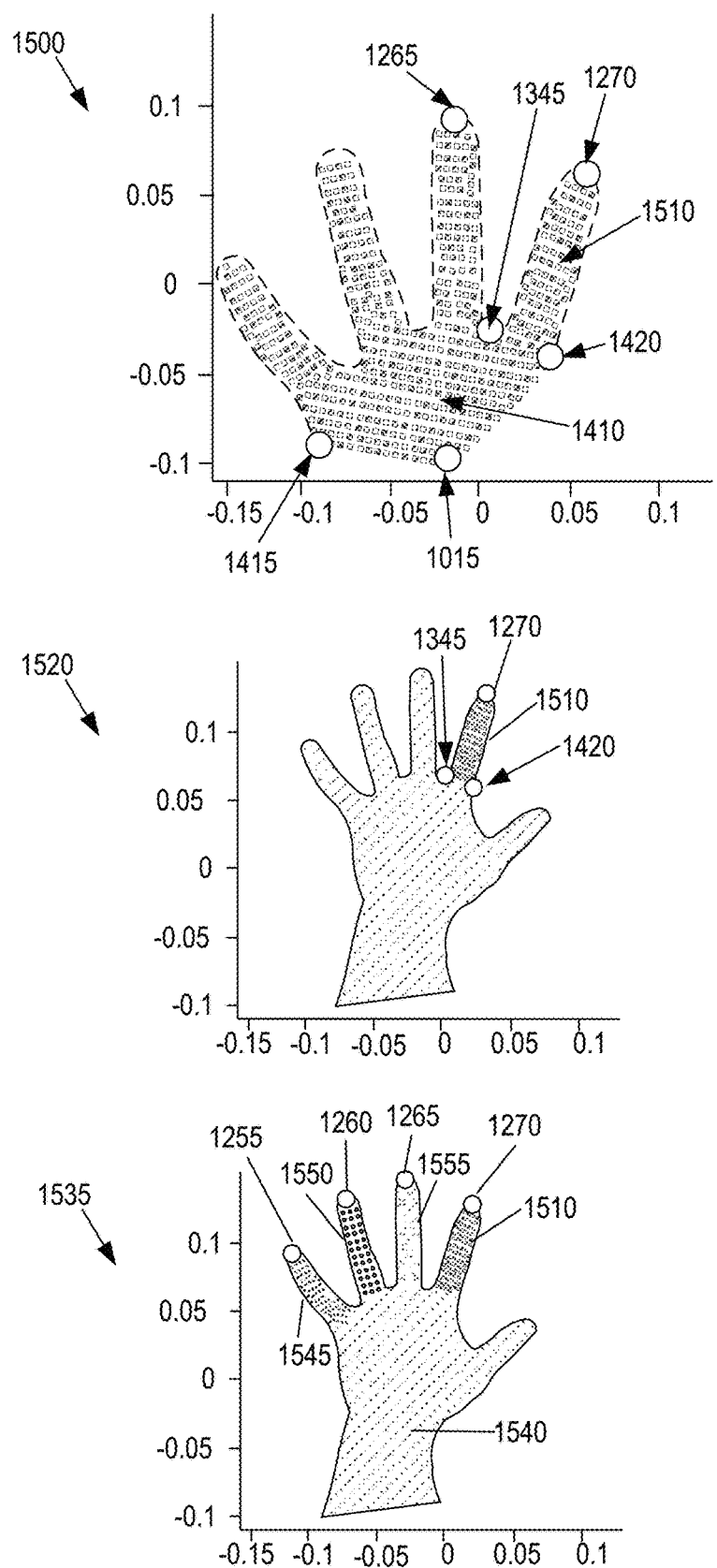

Referring to FIG. 15, and as shown as 3D hand information 1500, individual finger information can each be isolated from previously generated finger section 1410. In the specifically provided example index finger 1510 can be identified and isolated independently of the other fingers. As would be appreciated, isolation of each finger from the other fingers can enhance the ability to generate accurate 3D information therefrom which, in turn, can improve derived measurement quality. As shown in hand representation 1500, index finger 1510 can be isolated by beginning with finger section 1410 and identifying each of index fingertip 1270, middle fingertip 1265, and index web 1345. Next, as shown in hand representation 1520, index finger 1510 can be defined as all points in the hand bounded by index boundary point 1420, index web 1345, and index fingertip 1270.

As shown in hand representation 1535, each of the fingers can be processed in a similar manner as being bounded by a corresponding fingertip point and two adjacent web or boundary points to generate individual finger 3D information as each of 1510, 1545, 1550, and 1555, along with hand information and thumb information 1540, which were not processed as shown in this step. The order of finger processing can be varied. In this regard, separate processing of each finger has been found useful to allow good resolution thereof. While this specific finger processing method is described, it can be expected that other methods can be used generate individual finger 3D information; for example, a priori hand information present in a library of information can have such utility in this regard.

Figure 16:
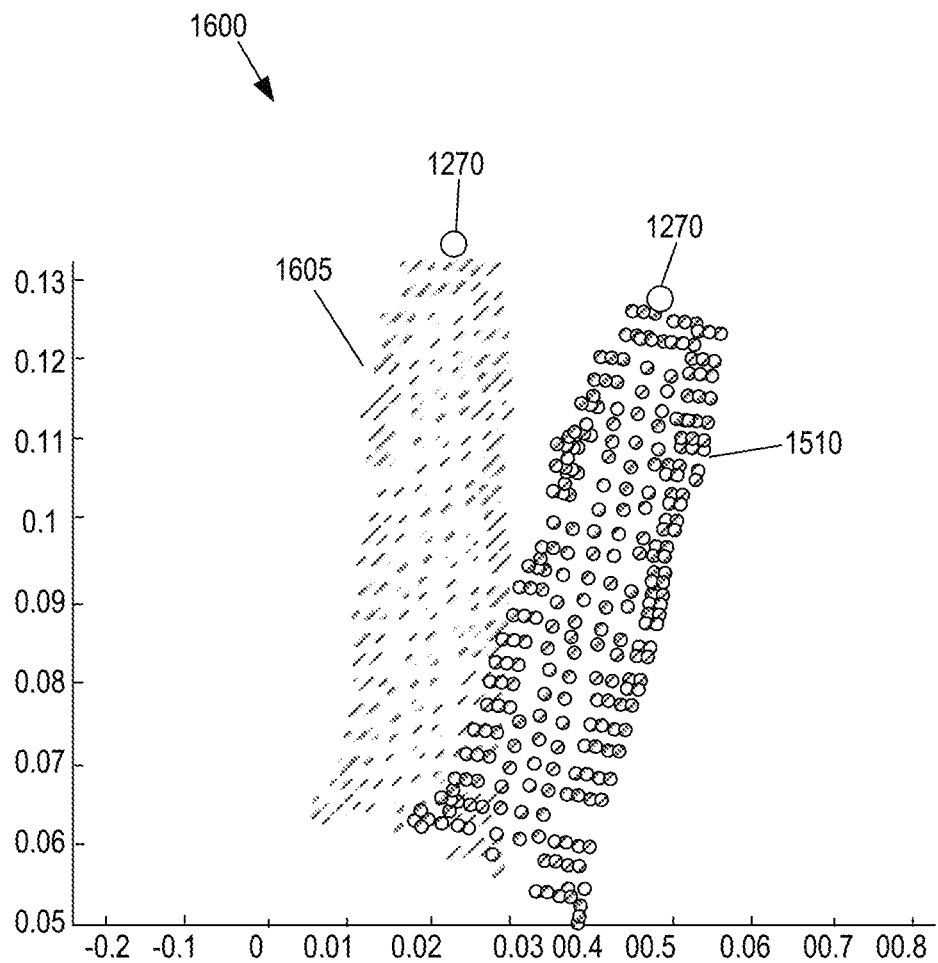
FIG. 16 illustrates an example of an index finger representation arranged in Cartesian coordinates, in accordance with various embodiments of the present disclosure.

Next, each 3D finger information 1510, 1545, 1550, and 1555 can be processed to generate measurements thereof, both lengthwise and along a plurality of circumferences. Turning to FIG. 16 in which index finger representation 1600, using index finger 3D information 1510 as an example, finger circumference information can be derived by establishing a plurality of cross-sectional slices perpendicular to the best fit line of index finger 1510 in increments of 1 inch, 1 centimeter, 1 millimeter or other increment based on the measurement resolution needed for the application, among other methods. Each finger can individually be rotated to be oriented toward vertical in the Cartesian coordinates by identifying a best fit line through the array of X coordinates of 3D index finger information 1510, followed by rotation thereof to a vertical position based on an angle of the generated best fit line to provide 3D index finger information 1605. Index finger 1510 length and circumference information can then be generated for incorporation in hand measurements as described herein. Alternatively, each finger can individually be rotated to be oriented according to a different axis as may be appropriate for various measurement protocols. Corresponding fingertip points (not shown) and the associated web point(s) (not shown) can also be rotated to serve as reference landmarks for subsequent measurements. A length of each finger can be measured as a distance between a fingertip and a corresponding web location, a distance between a fingertip and a corresponding average of two web locations, or between other anatomical landmarks such as the base of the fingernail bed as appropriate for the measurement protocol. Lengths can be measured as straight lengths between the two relevant points, centroid lengths along the path of calculated 3D centroids, or contour lengths defined along the surface of the 3D shape, among other length measurement protocols as may be appropriate. Optionally, a distance between any two locations can also be adjusted by a correction factor, where the correction factor can be derived from analysis of a historical information library according to the following:

Y coordinate of landmark 1-Y coordinate of landmark 2-correction factor.

To generate circumferences of each finger, each isolated 3D finger information collection can be cross-sectionally sliced horizontally, sliced perpendicularly to a calculated centroid line, or sliced according to a defined axis for the desired measurement, and the slices can be generated as individual slices or in increments of about 1 or 2 inches or about 1 or 2 centimeters or about 1 or 2 millimeters as appropriate for the desired measurements. The circumference of each cross-sectional slice can be determined by identifying the points on the slice constituting the perimeter, which can be done via a boundary function, point sampling at defined angular intervals, or other method as appropriate. Circumference can be calculated as the sum of the distances between the perimeter points, the distance of a spline function fit to the perimeter points, or other method as appropriate for the measurement protocol. Circumference measurements can include a derived correction factor to account for the palm side of the hand that is not directly captured in the imaging event due to the hand being placed on a flat surface for imaging. Depending on the measurement tolerance required for the selected measurement protocol, the correction factor can range from a simple straight-line closure of the perimeter at the level of the surface to a multi-dimensional curvature closure with an optional measurement offset correction factor as derived from the referenced library of historical information.

As would be appreciated, a number of circumferences relevant for each finger can be associated with an intended functionality of a glove or glove-like garment that might be fit from the subject finger measurements and various measurement protocols may be used for different measurement outputs. In an implementation, at least two circumferences can be generated for each finger—Proximal Finger Circumference and Distal Finger Circumference— according to the following example protocol:

Proximal Finger Circumference is an average of the circumferences 1 cm, 1.5 cm, and 2 cm distal to that finger web; and Distal Finger Circumference is the average of the circumferences 1 cm, 1.5 cm, and 2 cm proximal to that finger tip.

Finger circumferences can also be measured at defined anatomic landmarks as may be appropriate. For example, a proximal finger circumference may be measured at the point with the largest circumference at the proximal end of the finger, which often occurs at the proximal interphalangeal joint, and the distal circumference may be measured at the base of the nail bed or at the distal interphalangeal joint.

It is further noted that the smaller circumferences associated with fingers as compared to those of arms or legs can enhance the value of an available library of historical data for use in the generation of finger circumference measurements, at least because correct fitting of gloves will be in relation to smaller circumference measurements as are associated with fingers and thumbs. In other words, errors in glove fitting using measurements derived from or associated with 3D images are likely to be proportionally greater than with measurements for garments intended to fit on arms and/or legs. Such use of a library of historical information can assist in generating at least the finger circumference measurements to provide significant improvements over prior art hand measurement methodology where such measurements are derived from 3D imaging techniques.

Figure 17A:
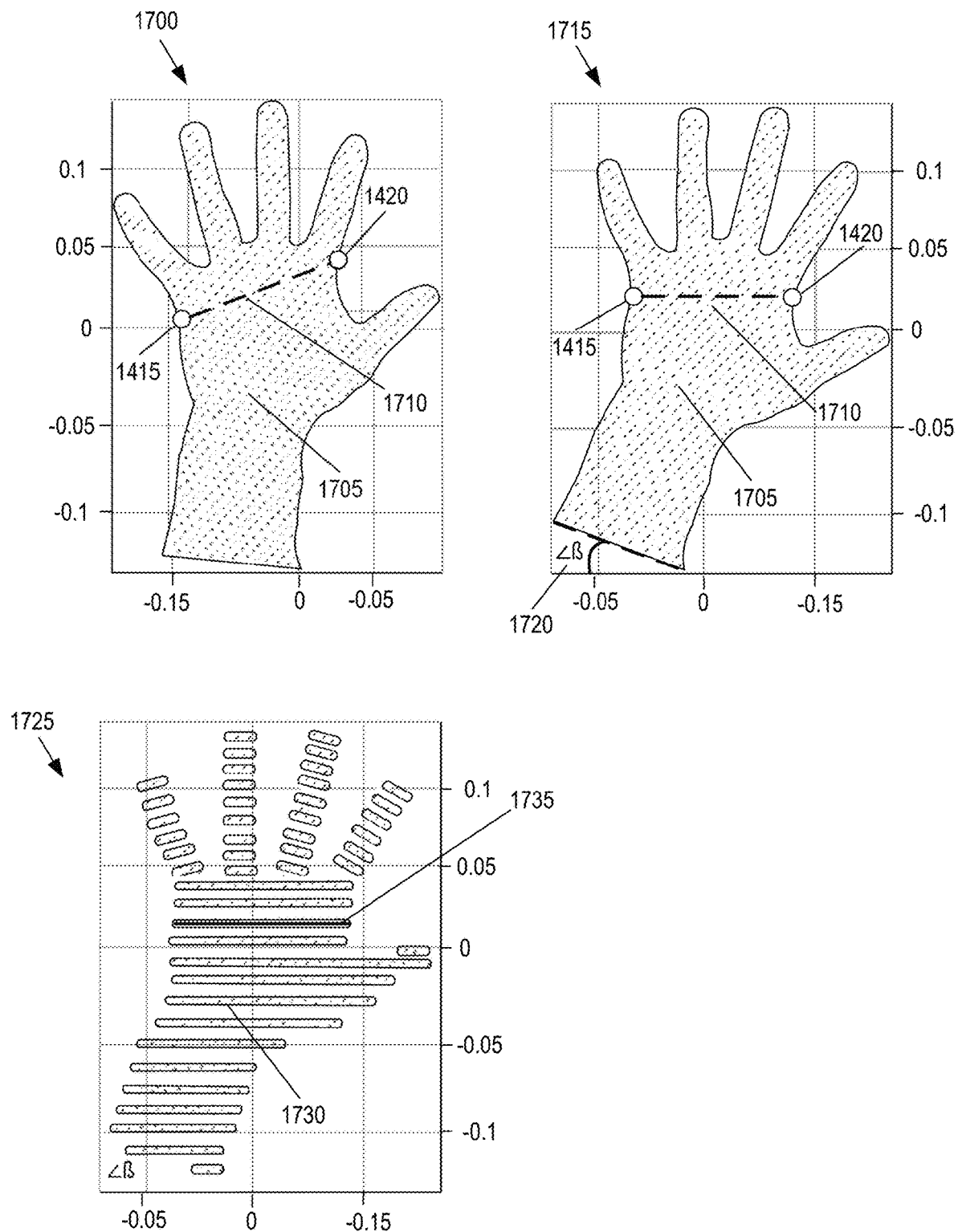
FIGS. 17A and 17B illustrate examples of 3D hand representations arranged in Cartesian coordinates, in accordance with various embodiments of the present disclosure.

Hand circumference can be determined according to the following steps, among others as needed for measurement specifications. To generate measurements of the palm, the 3D hand information collection can be sliced horizontally, sliced perpendicularly to a calculated centroid line, or sliced according to a defined axis for the desired measurement, and the slices can be generated as individual slices or in increments of about 1 or 2 inches or about 1 or 2 centimeters or about 1 or 2 millimeters as appropriate for the desired measurements. For example, referring to FIG. 17A, hand information 1700 shows temporary hand matrix 1705 with a line drawn between pinky boundary point 1415 and index finger boundary point 1420 and to generate distance 1710. As shown in 1715, temporary hand matrix 1705 can then be rotated about the Z-axis by an angle β 1720 such that pinky boundary point 1415 and index boundary point 1420 both lie on the x axis. Cross-sectional slices as shown in 1725 can be generated in increments of 1 or 2 inches or 1 or 2 centimeters or about 1 or 2 millimeters or other increments as appropriate for the desired measurement resolution as shown in sliced hand representation 1730. A circumference for each cross-sectional slice can be determined by identifying the points on the slice constituting the perimeter, which can be done via a boundary function, point sampling at defined angular intervals, or other method as appropriate, such as slice 1735. Circumferences can be calculated as the sum of the distances between the perimeter points, the distance of a spline function fit to the perimeter points, or other method as appropriate for the measurement protocol. Circumference measurements can include a derived correction factor to account for the palm side of the hand that is not directly captured in the imaging event due to the hand being placed on a flat surface for imaging. Depending on the measurement tolerance appropriate for the selected measurement protocol, the correction factor can range from a simple straight-line closure of the perimeter at the level of the surface to a multi-dimensional curvature closure with an optional measurement offset correction factor as derived from the referenced library of historical information. Other palm circumference measurements can be generated using the same axis of rotation as was used to generate hand circumference 1735, or alternative rotation axes can be used as needed.

Figure 17B:
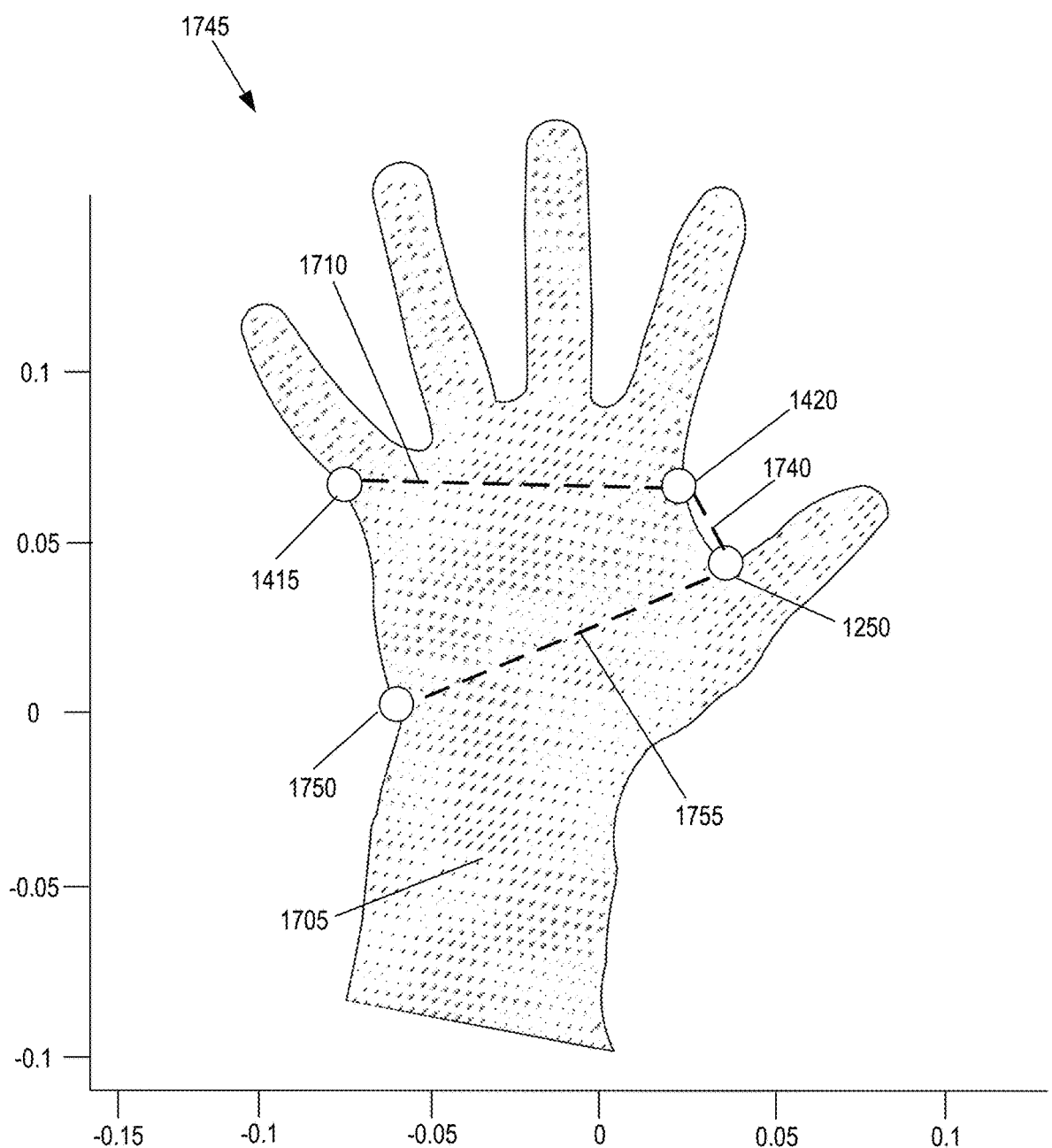

Palm lengths can be measured between anatomical landmarks as required for the desired measurement protocol, such as examples shown in FIG. 17B as 3D hand representation 1745 between pinky boundary 1415 and index boundary 1420 (length 1710), between index boundary 1420 and thumb web 1250 (length 1740), and between thumb web 1250 and the widest point on the palm 1750 (length 1755). Lengths can also be measured between finger landmarks and palm landmarks, between palm landmarks and wrist/arm landmarks, and between finger landmarks and arm/wrist landmarks as needed for the desired measurement protocol, among other lengths as may be appropriate. Lengths can be straight-line lengths, centroid lengths, or surface contour lengths as appropriate for the desired measurement protocol, among other length measurement methodologies.

Figure 18:
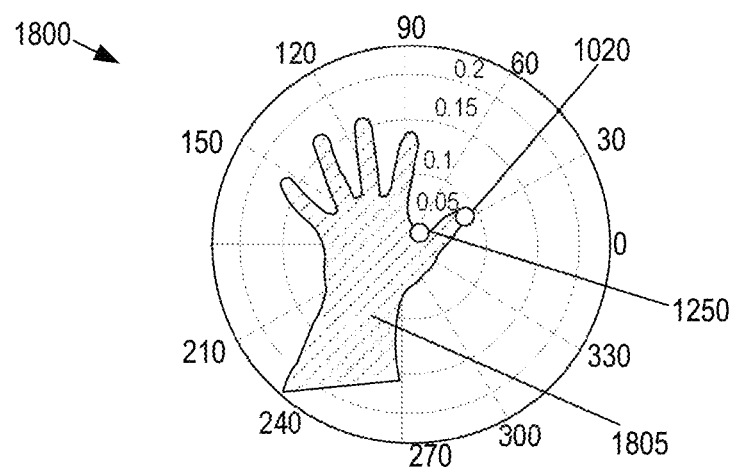
FIG. 18 illustrates examples of hand representations arranged in polar coordinates, in accordance with various embodiments of the present disclosure.
Figure 18:
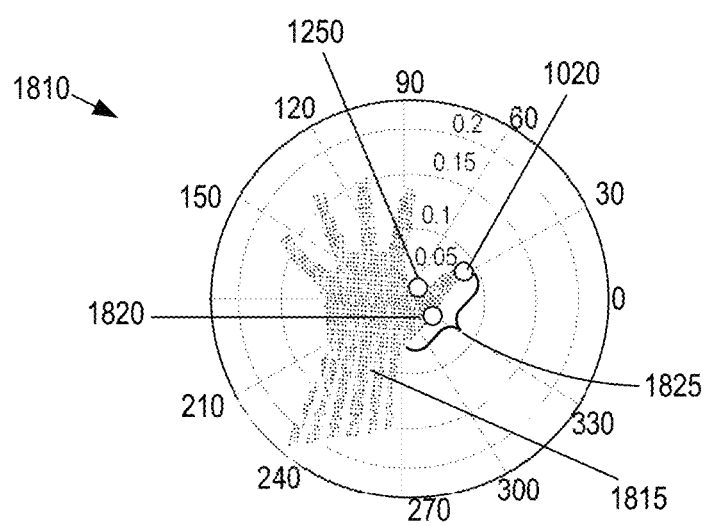
Figure 18:
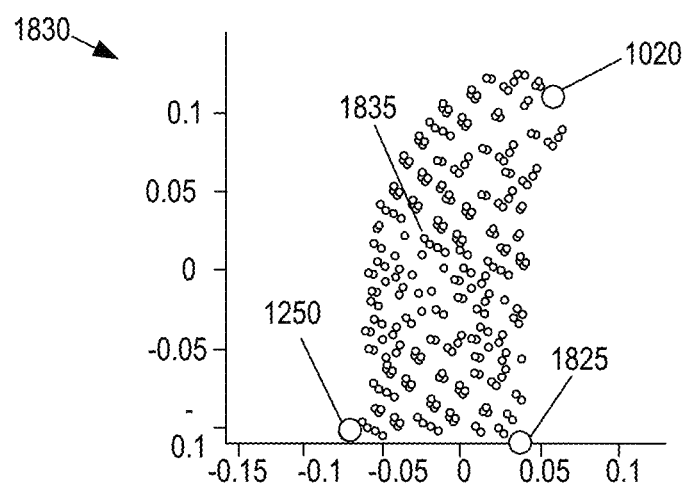

Next, thumb information can be generated. Referring to FIG. 18, hand representation 1800 shows temporary hand matrix 1805 translated to polar coordinates including thumb end 1020 with thumb web 1250 at the origin. Hand representation 1810 shows temporary hand matrix 1815 where the points were rounded to the nearest 10 degrees, as an example. A search window in an area associated with an outer thumb location can be identified in order to determine a thumb boundary point. That area can be searched and points with theta values between about 270 and about 360 degrees can be identified. Next, each unique theta value within the thumb web search window can be identified and a thumb boundary data array 1820 can be created by identifying a point with the smallest r value for each unique theta value. Thumb boundary point 1825 can be generated from iterations where temporary hand matrix 1815 is rotated a number of degrees in each iteration. For example, the degrees per rotation can be 1 degree per rotations to generate four iterations can be rotations of 0 degrees, 1 degree, 2 degrees, and 3 degrees. Thumb boundary point 1825 can be defined as the point with the maximum r value among the four values derived in each of the four iterations. The opposite of the transformations and rotations in this step can then be conducted to restore generated information to a form suitable for further processing. As is shown in 1830, 3D thumb information 1835 from which accurate measurements are derivable can be generated by transforming hand information 1805 into Cartesian coordinates and then isolating the thumb as bounded by thumb web point 1250, thumb boundary point 1825, and thumb end 1020.

Thumb circumference and length measurements can now be generated. Points in isolated thumb 1835 can be rounded to the nearest 1 inch or 1 centimeter or 1 millimeter to create cross-sectional slices as needed for the desired measurement resolution. Thumb circumference and length measurements can be generated using the protocols for finger circumference and length measurement discussed herein.

Figure 19:
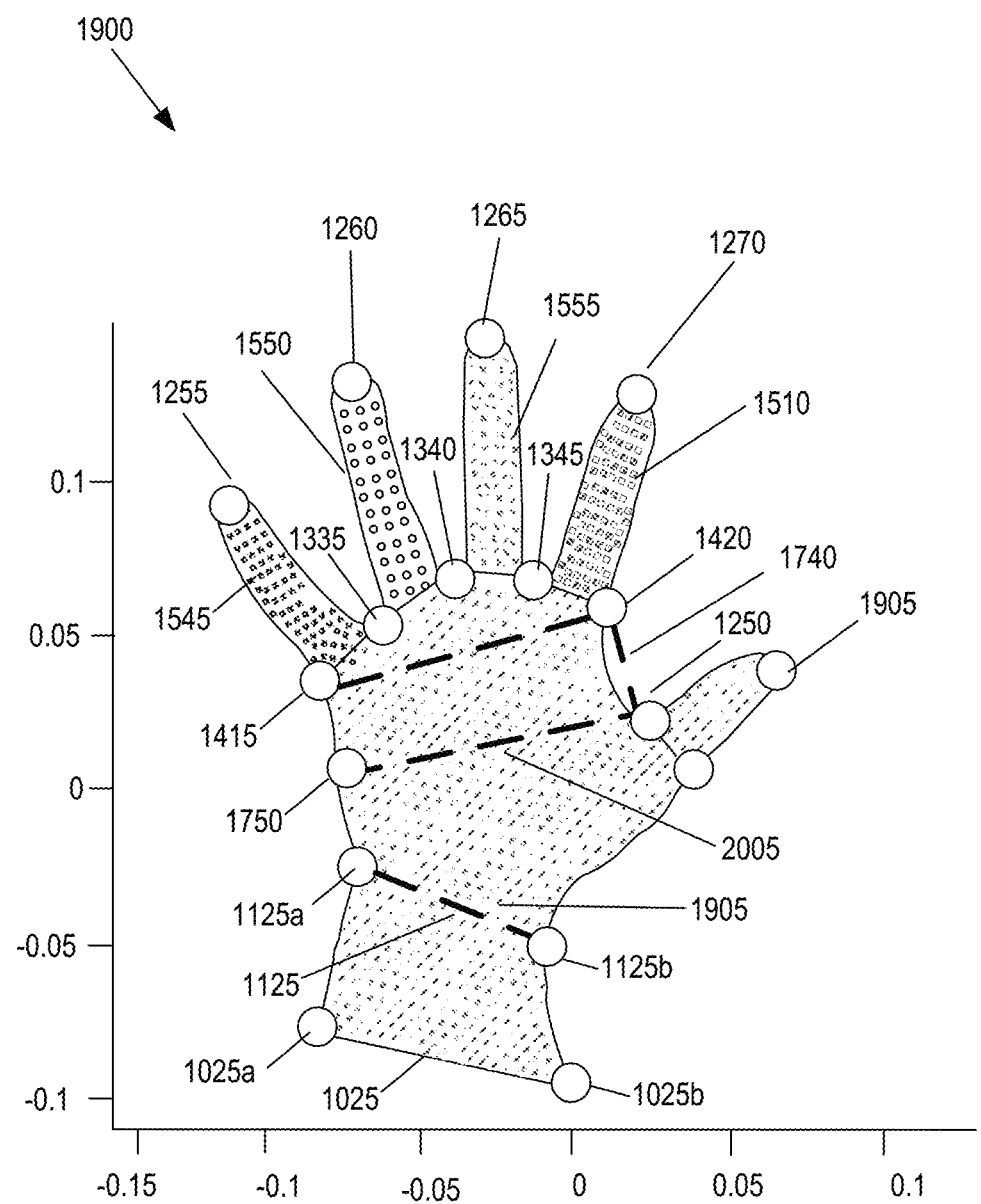
FIG. 19 illustrates an example of 3D hand representations arranged in Cartesian coordinates, in accordance with various embodiments of the present disclosure.
Figure 20C:
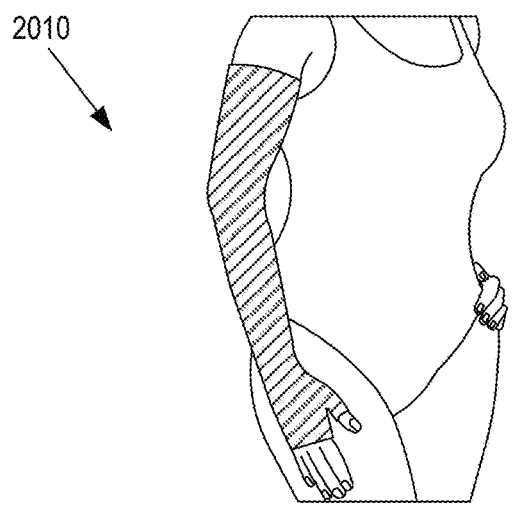

As shown in FIG. 19 as 3D hand information 1900 a collection of hand measurements are derivable from the previously described image processing steps where the measurements are derived from locations as shown. Such hand measurements can be useful in the fitting of compression garments that are gloves or that comprise glove-like components. Compression garments can be provided in the form of a hand gauntlet 2000 (FIG. 20A), glove 2005 (FIG. 20B) or arm sleeve gauntlet 2010 (FIG. 20C). As would be appreciated, such compression garments can be associated with one or more prescribed or indicated compression levels for application of compression to a person in need thereof. When included with a full or partial arm sleeve, measurement of the arm locations can be as set out elsewhere herein.

Figure 21:
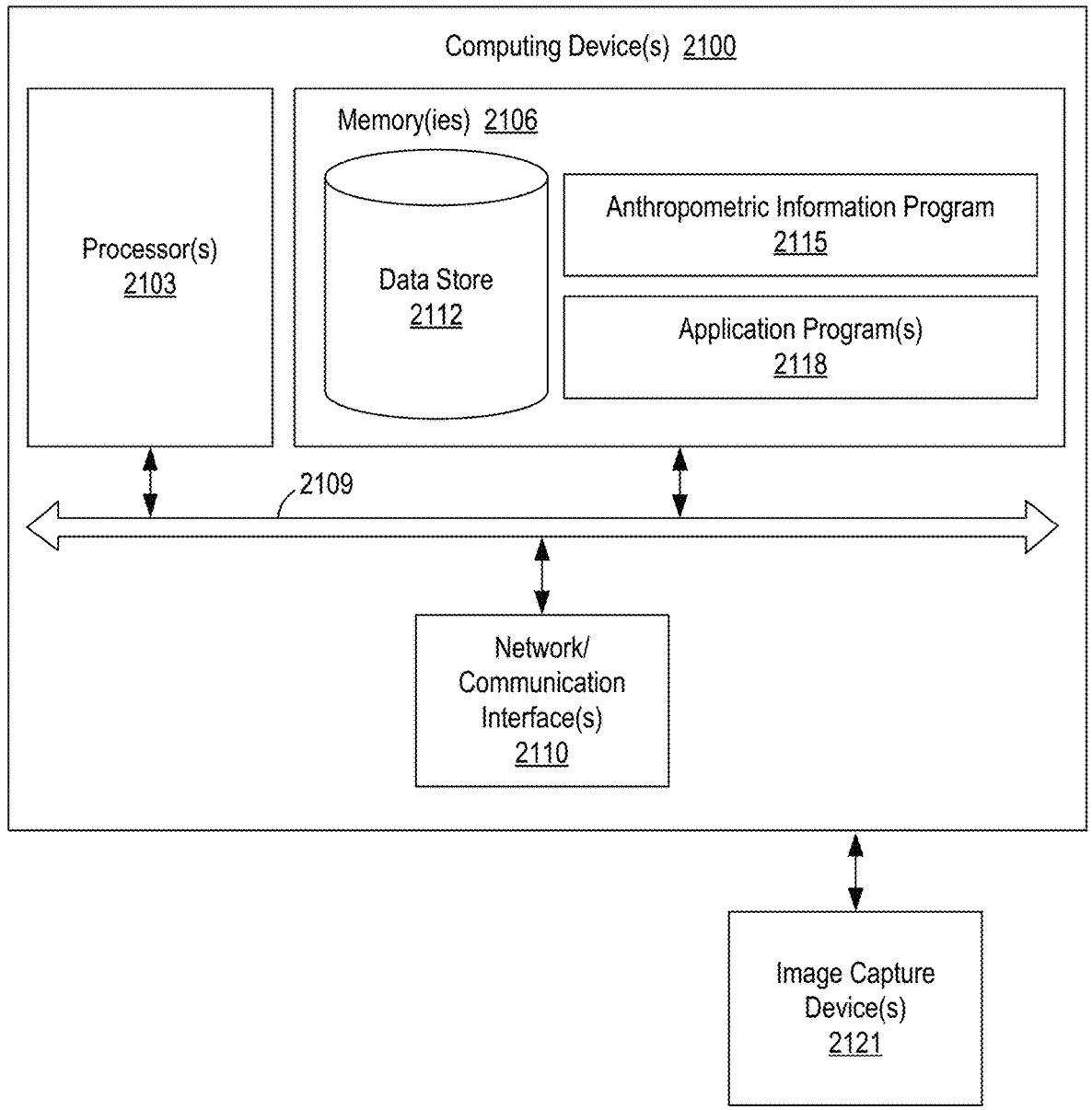
FIG. 21 is a schematic diagram illustrating an example of a computing system that can be used to derive anthropometric information for fitting compression garments, in accordance with various embodiments of the present disclosure.

With reference to FIG. 21, shown is a schematic block diagram of a computing device 800. In some embodiments, among others, the computing device 2100 may represent a mobile device (e.g., a smartphone, tablet, computer, etc.). Each computing device 2100 includes at least one processor circuit, for example, having a processor 2103 and a memory 2106, both of which are coupled to a local interface 2109. To this end, each computing device 2100 may comprise, for example, at least one server computer or like device, which can be utilized in a cloud-based environment. The local interface 2109 may comprise, for example, a data bus with an accompanying address/control bus or other bus structure as can be appreciated.

In some embodiments, the computing device 2100 can include one or more network/communication interfaces 2110. The network/communication interfaces 2110 may comprise, for example, a wireless transmitter, a wireless transceiver, and/or a wireless receiver. As discussed above, the network interface 2110 can communicate to a remote computing device using a Bluetooth, Wi-Fi, or other appropriate wireless protocol. As one skilled in the art can appreciate, other wireless protocols may be used in the various embodiments of the present disclosure. In addition, the computing device 2100 can be in communication with one or more image capture device(s) 2121. In some implementations, an image capture device 2121 can be incorporated in the computing device 2100 and can interface through the locate interface 2109.

Stored in the memory 2106 are both data and several components that are executable by the processor 2103. In particular, stored in the memory 2106 and executable by the processor 2103 can be an anthropometric information program 2115 and potentially other application program(s) 2118. Also stored in the memory 2106 may be a data store 2112 and other data. In addition, an operating system may be stored in the memory 2106 and executable by the processor 2103.

It is understood that there may be other applications that are stored in the memory 2106 and are executable by the processor 2103 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages.

A number of software components are stored in the memory 2106 and are executable by the processor 2103. In this respect, the term "executable" means a program file that is in a form that can ultimately be run by the processor 2103. Examples of executable programs may be, for example, a compiled program that can be translated into machine code in a format that can be loaded into a random access portion of the memory 2106 and run by the processor 2103, source code that may be expressed in proper format such as object code that is capable of being loaded into a random access portion of the memory 2106 and executed by the processor 2103, or source code that may be interpreted by another executable program to generate instructions in a random access portion of the memory 2106 to be executed by the processor 2103, etc. An executable program may be stored in any portion or component of the memory 2106 including, for example, random access memory (RAM), read-only memory (ROM), hard drive, solid-state drive, USB flash drive, memory card, optical disc such as compact disc (CD) or digital versatile disc (DVD), floppy disk, magnetic tape, holographic storage, or other memory components.

The memory 2106 is defined herein as including both volatile and nonvolatile memory and data storage components. Volatile components are those that do not retain data values upon loss of power. Nonvolatile components are those that retain data upon a loss of power. Thus, the memory 2106 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random-access memory (SRAM), dynamic random-access memory (DRAM), or magnetic random-access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 2103 may represent multiple processors 2103 and/or multiple processor cores, and the memory 2106 may represent multiple memories 2106 that operate in parallel processing circuits, respectively. In such a case, the local interface 2109 may be an appropriate network that facilitates communication between any two of the multiple processors 2103, between any processor 2103 and any of the memories 2106, or between any two of the memories 2106, etc. The local interface 2109 may comprise additional systems designed to coordinate this communication, including, for example, performing load balancing. The processor 2103 may be of electrical or of some other available construction.

Although the anthropometric information program 2115 and other application program(s) 2118 described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

Also, any logic or application described herein, including the anthropometric information program 2115 and the application program 2118, that comprises software or code can be embodied in any non-transitory computer-readable medium for use by or in connection with an instruction execution system such as, for example, a processor 2103 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random-access memory (RAM) including, for example, static random-access memory (SRAM) and dynamic random-access memory (DRAM), or magnetic random-access memory (M RAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including the anthropometric information program 2115 and the other application program(s) 2118, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 2100, or in multiple computing devices in the same computing environment 103. To this end, each computing device 2100 may comprise, for example, at least one server computer or like device, which can be utilized in a cloud-based environment. Additionally, it is understood that terms such as "application," "service," "system," "engine," "module," and so on may be interchangeable and are not intended to be limiting.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The term "substantially" is meant to permit deviations from the descriptive term that don't negatively impact the intended purpose. Descriptive terms are implicitly understood to be modified by the word substantially, even if the term is not explicitly modified by the word substantially.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about y".

The invention claimed is:

1. A method of generating information for the fitting of compression garments having glove or glove-like features, comprising:
  a) selecting, by a user or a computer, a hand of a person in need of fitting for a compression garment configured to provide a prescribed or intended amount of compression therapy to the hand when the compression garment is worn by the person;
  b) generating, from a handheld imaging device, a plurality of acquired images of the hand, wherein during image acquisition:
    i) the hand is positioned on a surface with a palm area facing the surface;
    ii) the hand comprises:
      (1) a thumb:
      (2) a plurality of fingers:
      (3) a hand area including the palm area that is substantially not visible;
      (4) a wrist area; and
      (5) a hand end or forearm area;
    iii) the thumb and the plurality of fingers are arranged in a splayed configuration; and
    iv) the handheld imaging device moves freely around the hand with 6 degrees of freedom unconstrained by a mount or support;
  c) processing, by the handheld imaging device or the computer, the plurality of acquired images to generate hand measurements associated with one or more locations relevant to the fitting of the compression garment on the hand of the person; and
  d) providing, by the imaging device or the computer, the hand measurements for use in generating compression garment fit instructions for the person, wherein the compression garment fit instructions are associated with:
    i) selection of a prefabricated compression garment from a collection of prefabricated compression garments; or
    ii) fabricated of a custom compression garment.

2. The method of claim 1, wherein the image processing incorporates a prion information comprising one or more of:
  a) a collection of compression garment fit instructions provided by one or more compression garment manufacturers;
  b) information associated with prior compression garment fit events for the person or for one or more other individuals potentially or actually in need of compression therapy; or
  c) information associated with a health condition for the person or for one or more other persons potentially or actually in need of compression therapy.

3. The method of claim 2, wherein the information associated with prior compression garment fit events is generated from either or both of tape measurements and imaging, and wherein at least some of the information associated with prior compression garment fit events is validated by a human prior to use of the information in processing of the plurality of acquired images.

4. The method of claim 1, wherein the hand measurements are associated with some or all of:
  i) one or more fingers;
  ii) the thumb;
  iii) the hand area including the palm area;
  iv) the wrist area; and
  v) the hand end or forearm area.

5. The method of claim 4, wherein the hand measurements include circumferences for some or all of:
  i) one or more fingers;
  ii) the thumb;

iii) one or more areas on the hand area including the palm area;
iv) the wrist area; and
v) the hand end or forearm area.

6. The method of claim 1, wherein the hand measurements include information derived from web areas located between one or more of:
a) a pinky finger and a ring finger;
b) the ring finger and a middle finger;
c) the middle finger and an index finger; and
d) the index finger and the thumb.

7. The method of claim 1, further comprising:
a) providing a compression garment associated with the generated compression garment fit instructions to the person;
b) collecting information associated with the person's wearing of the provided compression garment from a first time to a second time; and
c) incorporating the collected information into a library of compression garment fit information for use in:
   i) generating additional compression garment fit information for the person; or
   ii) generating compression garment fit information for one or more other persons in need of compression therapy.

8. The method of claim 1, wherein the selected prefabricated compression garment or fabricated custom compression garment:
a) is a glove;
b) incorporates a prescribed or indicated compression value of from 20 to 50 mm Hg; and
c) is configured to apply the prescribed or indicated compression value when the compression garment is worn by the person.

9. The method of claim 1, wherein the selected prefabricated compression garment or fabricated custom compression garment:
a) is a gauntlet;
b) incorporates a prescribed or indicated compression value of from 20 to 50 mm Hg; and
c) is configured to apply the prescribed or indicated compression value when the compression garment is worn by the person.

10. The method of claim 1, wherein the selected prefabricated compression garment or fabricated custom compression garment:
a) is an arm sleeve;
b) incorporates a prescribed or indicated compression value of from 20 to 50 mm Hg; and
c) is configured to apply the prescribed or indicated compression value when the compression garment is worn by the person.

11. The method of claim 1, wherein during image acquisition a user is provided with information associated with a need to acquire additional images in one or more locations of the hand.

12. A method of generating information associated with a difference in hand measurement information for a person at a first time and a second time comprising:
a) selecting, by a user or a computer, a hand of a person in need of fitting for a compression garment configured to provide a prescribed or intended amount of compression therapy to the hand when the compression garment is worn by the person;
b) generating, by a handheld imaging device, at a first time and at a second time a plurality of images of the hand, wherein during each image acquisition:
   i) the hand is positioned on a surface with a palm area facing the surface;
   ii) the hand comprises:
      (1) a thumb;
      (2) a plurality of fingers:
      (3) a hand area including the palm area that is substantially not visible:
      (4) a wrist; and
      (5) a hand end or forearm area;
   iii) the thumb and the plurality of fingers are arranged in a splayed configuration; and
   iv) the handheld imaging device moves freely around the hand with 6 degrees of freedom unconstrained by a mount or support;
c) processing, by the handheld imaging device or the computer, the plurality of images acquired at the first time and the second time to generate first and second hand measurements, wherein each of the first and second hand measurements are each, independently, associated with one or more locations relevant to the fitting of the compression garment on the hand; and
d) generating, by the handheld imaging device or the computer, first and second compression garment fit instructions for the person, wherein the first and second compression garment fit instructions are associated with:
   i) selection of a first or a second prefabricated compression garment from a collection of prefabricated compression garments; or
   ii) fabrication of a first or a second custom compression garment.

13. The method of claim 12, further comprising:
a) comparing, by the handheld imaging device or the computer, the first and second hand measurements; and
b) generating, by the handheld imaging device or the computer, information about a presence or absence of a change between the first and second hand measurements.

14. The method of claim 13, wherein when there is a change between the first and second hand measurements, generating information associated with a health condition for the person.

15. The method of claim 12, wherein the image processing incorporates a priori information comprising one or more of:
a) a collection of compression garment fit instructions provided by one or more compression garment manufacturers;
b) information associated with prior compression garment fit events for the person or for one or more other individuals potentially or actually in need of compression therapy, wherein:
   i) the information is generated from either or both of tape measurements and imaging; and
   ii) at least some of the information is validated by a human prior to use of the information in processing of the acquired images; and
c) information associated with a health condition for the person or for one or more other persons potentially or actually in need of compression therapy.

16. The method of claim 12, wherein each of the first and second hand measurements are associated with some or all of:
i) one or more fingers;
ii) the thumb;
iii) the hand area including the palm area;
iv) the wrist area; and
v) the hand end or forearm area.

17. The method of claim 16, wherein some of the first and second hand measurements are derived from information generated from web areas located between one or more of:
   a) a pinky finger and a ring finger;
   b) the ring finger and a middle finger;
   c) the middle finger and an index finger; and
   d) the index finger and the thumb.

18. The method of claim 16, wherein the first and second hand measurements include circumferences for some or all of:
   i) one or more fingers;
   ii) the thumb;
   iii) one or more areas on the hand area including the palm area;
   iv) the wrist area; and
   v) the hand end or forearm area.

19. The method of claim 12, wherein the first or second selected prefabricated compression garment or first or second fabricated custom compression garment:
   a) is configured as a glove, gauntlet, or an arm sleeve;
   b) incorporates a prescribed or indicated compression value of from 20 to 50 mm Hg; and
   c) is configured to apply the prescribed or indicated compression value when the compression garment is worn by the person.

20. The method of claim 12, wherein during image acquisition a user is provided with information associated with a need to acquire additional images in one or more locations of the hand.

\* \* \* \* \*